(12) United States Patent
Miller et al.

(10) Patent No.: US 11,845,965 B2
(45) Date of Patent: *Dec. 19, 2023

(54) REGULATION OF GENE EXPRESSION USING ENGINEERED NUCLEASES

(71) Applicant: Sangamo Therapeutics, Inc., Richmond, CA (US)

(72) Inventors: Jeffrey C. Miller, Richmond, CA (US); Edward J. Rebar, Richmond, CA (US)

(73) Assignee: Sangamo Therapeutics, Inc., Brisbane, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/738,766

(22) Filed: Jan. 9, 2020

(65) Prior Publication Data

US 2020/0131490 A1 Apr. 30, 2020

Related U.S. Application Data

(63) Continuation of application No. 16/281,751, filed on Feb. 21, 2019, now Pat. No. 10,563,184, which is a continuation of application No. PCT/US2017/048397, filed on Aug. 24, 2017.

(60) Provisional application No. 62/378,978, filed on Aug. 24, 2016, provisional application No. 62/443,981, filed on Jan. 9, 2017, provisional application No. 62/545,778, filed on Aug. 15, 2017.

(51) Int. Cl.
| | |
|---|---|
| *A61K 35/28* | (2015.01) |
| *A61K 38/00* | (2006.01) |
| *A61P 7/00* | (2006.01) |
| *A61P 7/06* | (2006.01) |
| *C12N 9/22* | (2006.01) |
| *C12N 15/87* | (2006.01) |
| *C12N 15/85* | (2006.01) |
| *C12N 15/90* | (2006.01) |
| *A61K 35/12* | (2015.01) |

(52) U.S. Cl.
CPC ............... *C12N 9/22* (2013.01); *A61K 35/28* (2013.01); *A61P 7/06* (2018.01); *C12N 15/85* (2013.01); *C12N 15/87* (2013.01); *C12N 15/90* (2013.01); *C12N 15/907* (2013.01); *A61K 38/00* (2013.01); *A61K 2035/124* (2013.01); *C07K 2319/09* (2013.01); *C07K 2319/81* (2013.01)

(58) Field of Classification Search
CPC .. A61K 35/27; A61K 38/00; A61K 2035/124; A61P 7/00; A61P 7/06; C07K 2319/09; C07K 2319/81; C12N 9/22; C12N 15/85; C12N 15/87
See application file for complete search history.

(56) References Cited

U.S. PATENT DOCUMENTS

| | | |
|---|---|---|
| 5,356,802 A | 10/1994 | Chandrasegaran |
| 5,436,150 A | 7/1995 | Chandrasegaran |
| 5,487,994 A | 1/1996 | Chandrasegaran |
| 5,789,538 A | 8/1998 | Rebar et al. |
| 5,925,523 A | 7/1999 | Dove et al. |
| 6,007,988 A | 12/1999 | Choo et al. |
| 6,013,453 A | 1/2000 | Choo et al. |
| 6,140,081 A | 10/2000 | Barbas |
| 6,140,466 A | 10/2000 | Barbas, III et al. |
| 6,200,759 B1 | 3/2001 | Dove et al. |
| 6,242,568 B1 | 6/2001 | Barbas, III et al. |
| 6,410,248 B1 | 6/2002 | Greisman et al. |
| 6,453,242 B1 | 9/2002 | Eisenberg et al. |
| 6,479,626 B1 | 11/2002 | Kim et al. |
| 6,503,717 B2 | 1/2003 | Case et al. |
| 6,534,261 B1 | 3/2003 | Cox, III et al. |
| 6,599,692 B1 | 7/2003 | Case et al. |
| 6,607,882 B1 | 8/2003 | Cox, III et al. |
| 6,689,558 B2 | 2/2004 | Case |
| 6,723,551 B2 | 4/2004 | Kotin et al. |
| 6,794,136 B1 | 9/2004 | Eisenberg et al. |
| 6,824,978 B1 | 11/2004 | Cox, III et al. |
| 6,903,185 B2 | 6/2005 | Kim et al. |
| 6,933,113 B2 | 8/2005 | Case et al. |
| 6,979,539 B2 | 12/2005 | Cox, III et al. |
| 6,989,264 B2 | 1/2006 | Atkinson et al. |
| 7,013,219 B2 | 3/2006 | Case et al. |
| 7,030,215 B2 | 4/2006 | Liu et al. |
| 7,067,317 B2 | 6/2006 | Rebar et al. |
| 7,070,934 B2 | 7/2006 | Cox, III et al. |
| 7,074,596 B2 | 7/2006 | Darzynkiewicz et al. |
| 7,153,949 B2 | 12/2006 | Kim et al. |
| 7,163,824 B2 | 1/2007 | Cox, III et al. |
| 7,253,273 B2 | 8/2007 | Collingwood |
| 7,262,054 B2 | 8/2007 | Jamieson et al. |
| 7,271,002 B2 | 9/2007 | Kotin et al. |
| 7,361,635 B2 | 4/2008 | Miller et al. |

(Continued)

FOREIGN PATENT DOCUMENTS

| | | |
|---|---|---|
| CA | 2660485 A1 | 2/2008 |
| CA | 2796464 A1 | 10/2011 |

(Continued)

OTHER PUBLICATIONS

Bauer et al, Science 342: 253-257, 2013.*

(Continued)

*Primary Examiner* — Kevin K Hill
(74) *Attorney, Agent, or Firm* — Snell & Wilmer, L.L.P.; April Wurster

(57) ABSTRACT

The present disclosure is in the field of genome engineering, particularly targeted modification of the genome of a hematopoietic cell.

11 Claims, 21 Drawing Sheets

Specification includes a Sequence Listing.

(56) References Cited

U.S. PATENT DOCUMENTS

| | | |
|---|---|---|
| 7,419,817 B2 | 9/2008 | Chiorini et al. |
| 7,888,121 B2 | 2/2011 | Urnov et al. |
| 7,914,796 B2 | 3/2011 | Miller et al. |
| 7,951,925 B2 | 5/2011 | Ando et al. |
| 7,972,854 B2 | 7/2011 | Miller et al. |
| 8,034,598 B2 | 10/2011 | Miller |
| 8,110,379 B2 | 2/2012 | DeKelver et al. |
| 8,153,773 B2 | 4/2012 | Jemielity et al. |
| 8,409,861 B2 | 4/2013 | Guschin et al. |
| 8,585,526 B2 | 11/2013 | Gregory et al. |
| 8,623,618 B2 | 1/2014 | Doyon et al. |
| 8,703,489 B2 | 4/2014 | Wang |
| 8,772,453 B2 | 7/2014 | Paschon et al. |
| 8,956,828 B2 | 2/2015 | Bonini et al. |
| 8,962,281 B2 | 2/2015 | Doyon et al. |
| 9,005,973 B2 | 4/2015 | Cost et al. |
| 9,045,763 B2 | 6/2015 | DeKelver et al. |
| 9,150,847 B2 | 10/2015 | Rebar |
| 9,200,266 B2 | 12/2015 | Wang |
| 9,234,187 B2 | 1/2016 | Rebar et al. |
| 9,255,250 B2 | 2/2016 | Gregory et al. |
| 9,394,531 B2 | 7/2016 | Miller |
| 9,567,609 B2 | 2/2017 | Paschon et al. |
| 10,563,184 B2* | 2/2020 | Miller ................... A61P 7/06 |
| 10,808,020 B2* | 10/2020 | Reik ................... C07K 14/705 |
| 2003/0232410 A1 | 12/2003 | Liljedahl et al. |
| 2005/0026157 A1 | 2/2005 | Baltimore et al. |
| 2005/0064474 A1 | 3/2005 | Urnov et al. |
| 2005/0208489 A1 | 9/2005 | Carroll et al. |
| 2005/0267061 A1 | 12/2005 | Martin |
| 2006/0063231 A1 | 3/2006 | Li et al. |
| 2006/0188987 A1 | 8/2006 | Guschin et al. |
| 2007/0218528 A1 | 9/2007 | Miller |
| 2008/0131962 A1 | 6/2008 | Miller |
| 2008/0159996 A1 | 7/2008 | Ando et al. |
| 2008/0299580 A1 | 12/2008 | DeKelver et al. |
| 2009/0068164 A1 | 3/2009 | Segal et al. |
| 2009/0305419 A1 | 12/2009 | Miller |
| 2010/0047805 A1 | 2/2010 | Wang |
| 2010/0218264 A1 | 8/2010 | Cui et al. |
| 2011/0182867 A1 | 7/2011 | Orkin et al. |
| 2011/0201055 A1 | 8/2011 | Doyon et al. |
| 2011/0207221 A1 | 8/2011 | Cost et al. |
| 2011/0265198 A1 | 10/2011 | Gregory et al. |
| 2011/0301073 A1 | 12/2011 | Gregory et al. |
| 2012/0017290 A1 | 1/2012 | Cui et al. |
| 2012/0195936 A1 | 8/2012 | Rudolph et al. |
| 2013/0122591 A1 | 5/2013 | Cost et al. |
| 2013/0130350 A1 | 5/2013 | Chandrasegaran et al. |
| 2013/0137104 A1 | 5/2013 | Cost et al. |
| 2013/0177983 A1 | 7/2013 | Rebar |
| 2013/0196373 A1 | 8/2013 | Gregory et al. |
| 2013/0209426 A1 | 8/2013 | Bradley et al. |
| 2013/0315884 A1 | 11/2013 | Galetto et al. |
| 2013/0326645 A1 | 12/2013 | Cost et al. |
| 2015/0056705 A1 | 2/2015 | Conway et al. |
| 2015/0064789 A1 | 3/2015 | Paschon et al. |
| 2015/0132269 A1* | 5/2015 | Orkin ................... C07K 14/4702 424/93.21 |
| 2015/0166615 A1 | 6/2015 | Xia et al. |
| 2015/0322131 A1 | 11/2015 | Fornaro et al. |
| 2015/0335708 A1 | 11/2015 | Froelich et al. |
| 2016/0090607 A1 | 3/2016 | Conway et al. |
| 2016/0369262 A1 | 12/2016 | Reik et al. |
| 2018/0087072 A1 | 3/2018 | Miller et al. |
| 2018/0185516 A1 | 7/2018 | Ansell et al. |
| 2018/0340189 A1 | 11/2018 | Joung et al. |
| 2019/0048060 A1 | 2/2019 | Conway et al. |
| 2020/0131490 A1 | 4/2020 | Miller et al. |

FOREIGN PATENT DOCUMENTS

| | | |
|---|---|---|
| CN | 102358902 A | 2/2012 |
| CN | 102762726 A | 10/2012 |
| CN | 102939377 A | 2/2013 |
| CN | 103025344 A | 4/2013 |
| CN | 103361328 A | 10/2013 |
| CN | 105874071 A | 8/2016 |
| CN | 107405411 A | 11/2017 |
| CN | 108024544 A | 5/2018 |
| GB | 2338237 A | 12/1999 |
| WO | WO 95/19431 A1 | 7/1995 |
| WO | WO 96/06166 A1 | 2/1996 |
| WO | WO 98/37186 A1 | 8/1998 |
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | WO 98/54311 A1 | 12/1998 |
| WO | WO 00/27878 A1 | 5/2000 |
| WO | WO 01/60970 A2 | 8/2001 |
| WO | WO 01/88197 A2 | 11/2001 |
| WO | WO 02/016536 A1 | 2/2002 |
| WO | WO-02/057294 A2 | 7/2002 |
| WO | WO 02/077227 A2 | 10/2002 |
| WO | WO 02/099084 A2 | 12/2002 |
| WO | WO 03/016496 A2 | 2/2003 |
| WO | WO 2009/042163 A2 | 4/2009 |
| WO | WO-2011/064751 A1 | 6/2011 |
| WO | WO 2011/094198 A1 | 8/2011 |
| WO | WO-2011/097036 A1 | 8/2011 |
| WO | WO-2011/139335 A1 | 11/2011 |
| WO | WO-2011/146121 A1 | 11/2011 |
| WO | WO-2012/015938 A2 | 2/2012 |
| WO | 2014036219 A2 | 3/2014 |
| WO | WO-2014/186585 A2 | 11/2014 |
| WO | WO-2015/089077 A2 | 6/2015 |
| WO | WO 2015/168547 A2 | 11/2015 |
| WO | WO-2016/014794 A1 | 1/2016 |
| WO | WO 2016/128408 A1 | 8/2016 |
| WO | WO 2016/183298 A2 | 11/2016 |
| WO | WO-2017/011519 A1 | 1/2017 |
| WO | WO 2018/039448 A1 | 3/2018 |
| WO | WO 2018/107026 A1 | 6/2018 |

OTHER PUBLICATIONS

Miller, et al., "Enhancing Gene Editing Specificity By Attenuating DNA Cleavage Kinetics," Nature Biotechnology, vol. 37, pp. 945-952 (2019).

Psatha, et al., "Disruption of the BCL11A Erythroid Enhancer Reactivates Fetal Hemoglobin in Erythroid Cells of Patients With β-Thalassemia Major," Molecular Therapy Methods & Clinical Development, vol. 10, pp. 313-326 (2018).

Vierstra, et al., "Functional Footprinting of Regulatory DNA," Nature Methods, vol. 12, No. 10, pp. 927-932 (2015).

Bjurstrom, et al., "Reactivating Fetal Hemoglobin Expression in Human Adult Erythroblasts Through BCL11A Knockdown Using Targeted Endonucleases," Molecular Therapy-Nucleic Acids, vol. 5, p. e351 (2016).

Canver, et al., "Customizing the Genome as Therapy for the β-Hemoglobinopathies," Blood, vol. 127, No. 21, pp. 2536-2545 (2016).

Rebar, et al., "New Zinc Finger Nuclease Architectures for Highly Efficient Genome Engineering in Primary Cells At Large Scale With No Detectable Off-Target Effects," Molecular Therapy, vol. 25, No. 5, Suppl. 1, pp. 11-12 (2017).

Reik, et al., "Targeted Gene Modification in Hematopoietic Stem Cells: A Potential Treatment for Thalassemia and Sickle Cell Anemia," Blood, American Society of Hematology, vol. 122, No. 21, p. 434 (2013).

Tasan, et al., "Use of Genome-Editing Tools To Treat Sickle Cell Disease," Human Genetics, vol. 135, No. 9, pp. 1011-1028 (2016).

Bauer, et al., "Reawakening Fetal Hemoglobin: Prospects for New Therapies for the B-Globin Disorders," *Blood* 118(15):2945-53 (2012).

Bauer, et al., "An Erythroid Enhancer of BCL11A Subject To Genetic Variation Determines Fetal Hemoglobin Level," *Science* 342:253-257 (2013).

(56) References Cited

OTHER PUBLICATIONS

Beerli, et al., "Engineering Polydactyl Zinc-Finger Transcription Factors," *Nature Biotechnology* 20:135-141 (2002).
Brandow, et al., "Monitoring Toxicity, Impact, and Adherence of Hydroxyurea in Children With Sickle Cell Disease," *Am J Hematol* 86(9):804-806 (2011).
Chang, et al., "Modification of DNA Ends Can Decrease End Joining Relative To Homologous Recombination in Mammalian Cells," *Proc. Natl. Acad. Sci. USA* 84(14):4959-4963 (1987).
Chang, et al., "Long-Term Engraftment and Fetal Globin Induction Upon BCL11A Gene Editing in Bone-Marrow-Derived CD34+ Hematopoietic Stem and Progenitor Cells," *Mol Ther Methods Clin Dev* 4:137-148 (2017).
Choo, et al., "Advances in Zinc Finger Engineering," *Current Opinion in Structural Biology* 10:411-416 (2000).
Constantoulakis, et al., "Alpha-Amino-N-Butyric Acid Stimulates Fetal Hemoglobin in the Adult," *Blood* 72(6):1961-1967 (1988).
DeSimone, "5-Azacytidine Stimulates Fetal Hemoglobin Synthesis in Anemic Baboons," *Proc Nat'l Acad Sci USA* 79(14):4428-4431 (1982).
Elguero, et al., "Malaria Continues To Select for Sickle Cell Trait in Central Africa," *PNAS USA* 112(22):7051-7054 (2015).
Elrod-Erickson, et al., "ZIF268 Protein-DNA Complex Refined At 1.6 A: A Model System for Understanding Zinc Finger-DNA Interactions," *Structure* 4(10):1171-1180 (1996).
Funnell, et al., "2p15-p16.1 Microdeletions Encompassing and Proximal To BCL11A Are Associated With Elevated HbF In Addition To Neurologic Impairment," *Blood* 126(1):89-93 (2015).
Gabriel, et al., "An Unbiased Genome-Wide Analysis of Zinc-Finger Nuclease Specificity," *Nat Biotech* 29(9):816-823 (2011).
Guilinger, et al., "Broad Specificity Profiling of Talens Results in Engineered Nucleases With Improved DNA Cleavage Specificity," *Nat Methods.* 11(4):429-35 (2014).
Guillinger, et al., "Fusion of Catalytically Inactive CAS9 To FokI Nuclease Improves the Specificity of Genome Modification," *Nature Biotech.* 32(6):577-582 (2014).
Guo, et al., "Directed Evolution of an Enhanced and Highly Efficient FOKI Cleavage Domain for Zinc Finger Nucleases," *J. Mol. Biol.* 400(1):96-107 (2010).
Hoban, et al., "A Genome Editing Primer for the Hematologist," *Blood* 127(21):2525-2535 (2016).
Isalan, et al., "A Rapid, Generally Applicable Method To Engineer Zinc Fingers Illustrated By Targeting the HIV-1 Promoter," *Nat Biotechnol.* 19(7):656-660 (2001).
Karikó, et al., "Incorporation of Pseudouridine Into MRNA Yields Superior Nonimmunogenic Vector With Increased Translational Capacity and Biological Stability," *Molecular Therapy* 16(11):1833-1844 (2012).
Kim, et al., "Chimeric Restriction Endonuclease," *Proc. Natl. Acad. Sci. USA* 91:883-887 (1994).
Kim, et al., "Insertion and Deletion Mutants of FOKI Restriction Endonuclease," *J. Biol. Chem.* 269(50):31978-31981 (1994).
Kleinstiver, et al., "High-Fidelity CRISPR-CAS9 Variants With Undetectable Gnome-Wide Off-Targets," *Nature* 529(7587):490-495 (2016).
Kormann, et al., "Expression of Therapeutic Proteins After Delivery of Chemically Modified MRNA in Mice," *Nature Biotechnology* 29(2):154-157 (2011).
Ley, et al., "5-Azacytidine Selectively Increases γ-Globin Synthesis in a Patient With β+ Thalassemia," *N. Engl. J. Medicine* 307(24):1469-1475 (1982).
Ley, et al., "5-Azacytidine Increases γ-Globin Synthesis and Reduces the Proportion of Dense Cells in Patients With Sickle Cell Anemia," *Blood* 62(2):370-380 (1983).
Li, et al., "Functional Domains in FOK I Restriction Endonuclease," *Proc. Natl. Acad. Sci USA* 89:4275-4279 (1992).
Li, et al., "Alteration of the Cleavage Distance of FOK I Restriction Endonuclease By Insertion Mutagenesis," *Proc. Natl. Acad. Sci USA* 90:2764-2768 (1993).

Matson, et al., "Transcriptional Regulatory Elements in the Human Genome," *Ann Rev Genome Hum Genet* 7:29-59 (2006).
McCaffery, et al., "CRISPR-CAS9 D10A Nickase Target-Specific Fluorescent Labeling of Double Strand DNA for Whole Genome Mapping and Structural Variation Analysis," *Nucleic Acids Res.* 44(2):e11.doi:10.1093/nar/gkv878. (2016).
Miller, et al., "An Improved Zinc-Finger nuclease Architecture for Highly Specific Genome Editing," *Nat. Biotechnol.* 25(7):778-785 (2007).
Nehls, et al., "Two Genetically Separable Steps in the Differentiation of Thymic Epithelium," *Science* 272:886-889 (1996).
Orlando, et al., "Zinc-Finger nuclease-Driven Targeted Integration Into Mammalian Genomes Using Donors With Limited Chromosomal Homology," *Nucleic Acids Res.* 38(15):e152 (2010).
Pabo, et al., "Design and Selection of Novel CYS2-HIS2 Zinc Finger Proteins," Ann. Rev. Biochem. 70:313-340 (2001).
Pavletich, et al., "Zinc Finger-DNA Recognition: Crystal Structure of a ZIF268-DNA Complex At 2.1 Å," *Science* 252(5007):809-817 (1991).
Platt, et al., "Mortality in Sickle Cell Disease, Life Expectancy and Risk Factors for Early Death," *N Engl J Med* 330(23):1639-1644 (1994).
Potoka, et al., "Vasculopathy and Pulmonary Hypertension in Sickle Cell Disease," *Am J Physiol Lung Cell Mol Physiol.* 308(4):L314-L324 (2015).
Roberts, et al., Rebase: Restriction Enzymes and Methyltransferases, *Nucleic Acids Res.* 31:418-420 (2003).
Robbez-Masson, et al., "Functional Analysis of a Breast Cancer-Associated FGFR2 Single Nucleotide Polymorphism Using Zinc Finger Mediated Genome Editing," *Plos One* 8(11):e78839 (2013).
Roseff, "Sickle Cell Disease: A Review," *Immunohematology* 25(2):67-74 (2009).
Sadelain, et al., "Strategy for a Multicenter Phase I Clinical Trial To Evaluate Globin Gene Transfer in β-Thalassemia," *Ann. N.Y. Acad. Sci.* 1202(1):52-58 (2010).
Sankaran, et al., "Human Fetal Hemoglobin Expression is Regulated By the Developmental Stage-Specific Repressor BCL11A," *Science* 322:1839-1842 (2008).
Schaefer, et al., "Unexpected Mutations After CRISPR-CAS9 Editing In Vivo," *Nat Methods.* 14(6):547-548 (2017).
Segal, et al., "Custom DNA-Binding Proteins Come of Age: Polydactyl Zinc-Finger Proteins," *Current Opinion Biotechnology* 12:632-637 (2001).
Sharei, et al., "Ex Vivo Cytosolic Delivery of Functional Macromolecules To Immune Cells," *Plos One* doi:10.1371/journal.pone.0118803 (2015).
Sheng, et al., "Structure-Based Cleavage Mechanism of Thermus Thermophilus Argonaute DNA Guide Strand-Mediated DNA Target Cleavage," *Proc. Natl. Aca. Sci. U.S.A.* 111(2):652-657 (2014).
Slaymaker, et al., "Rationally Engineered CAS9 Nucleases With Improved Specificity," *Science* 351(6268):84-88 (2016).
Sternberg, et al., "Conformational Control of DNA Target Cleavage By CRISPR-CAS9," *Nature* 527(7576):110-113 (2015).
Swarts, et al., "DNA-Guided DNA Interference By a Prokaryotic Argonaute." *Nature* 507(7491):258-261 doi:10.1038/nature12971 (2014).
Tebas, et al., "Gene Editing of CCR5 in Autologous CD4 T Cells of Persons Infected With HIV," *The New England Journal of Medicine* 370(10):901 (2014).
Tsai, et al., "Guide-SEQ Enables Genome-Wide Profiling of Off-Target Cleavage By CRISPR-CAS Nucleases," *Nat Biotechnol* 33(2):187-197 (2015).
Wah, et al., "Structure of the Multimodular Endonuclease FOKI Bound To DNA," *Nature* 388:97-100 (1997).
Yannaki, et al., "Hematopoietic Stem Cell Mobilization for Gene Therapy of Adult Patients With Severe B-Thalassemia: Results of Clinical Trials Using G-CSF or Plerixafor in Splenectomized and Nonsplenectomized Subjects," *Mol Ther* 20(1):230-238 (2012).
Urnov et al., "Clinical-Scale Genome Editing of the Human BCL11A Erythroid Enhancer for Treatment of the Hemoglobinopathies", Blood, 2015, 126(23): 204.
AU Office Action on AU Appl. Ser. No. 2017315406 dated Nov. 20, 2020 (3 pages).

(56) References Cited

OTHER PUBLICATIONS

AU Office Action on AU Appl. Ser. No. 2021204432 dated Nov. 12, 2021 (2 pages).
Bjurstrom, et al., "Reactivating Fetal Hemoglobin Expression in Human Adult Erythroblasts Through BCL11A Knockdown Using Targeted Endonucleases," Molecular Therapy-Nucleic Acids, vol. 5 (2016), p. e351, (12 pages).
CO Office Action on CO Appl. Ser. No. NC2019/0002324 dated Sep. 29, 2020, no translation (5 pages).
EP Office Action on EP Appl. Ser No. 17 844 404.8 dated Aug. 25, 2020 (4 pages).
EP Search Report on EP Appl. Ser. No. 21198842.3 dated Apr. 8, 2022 (8 pages).
EP Supplementary European Search report and Opinion on EP Appl. Ser. No. 17 84 4404 dated Dec. 12, 2019 (8 pages).
GenBank Accession No. CDC04928.1 (May 31, 2013) (4 pages).
GenBank Accession No. KE199890.1 (Jun. 24, 2014) (5 pages).
GenBank Accession No. WP_049180434.1 (Jul. 20, 2015) (3 pages).
Hu, et al., "Chemical Biology Approaches to Genome Editing: Understanding, Controlling, and Delivering Programmable Nucleases", Cell Chemical Biology, vol. 23 (2016), pp. 57-73.
ID Office Action on ID Appl. Ser. No. PID201901566 dated Mar. 1, 2021 (4 pages).
IL Office Action on IL Appl. Ser. No. 264639 dated Jun. 20, 2022 (5 pages).
International Preliminary Report on Patentability on PCT Appl. Ser. No. PCT/US2017/048397 dated Mar. 7, 2019 (8 pages).
International Search Report and Written Opinion on PCT Appl. Ser. No. on PCT/US17/48397 dated Jan. 18, 2018 (12 pages).
JP Office Action on JP Appl. Ser. No. 2019-510787 dated Aug. 3, 2021 (7 pages).
JP Office Action on JP Appl. Ser. No. 2019-510787 dated May 24, 2022, with translation (8 pages).
Khalil et al., "A Synthetic Biology Framework for Programming Eukaryotic Transcription Functions," Cell, 150:647-658 (Aug. 3, 2012).
Kisselev, "Polypeptide Release Factors in Prokaryotes and Eukaryotes: Same Function, Different Structure," Structure, Jan. 2002, vol. 10 (pp. 8-9).
KR Notice of Preliminary Rejection on KR Appl. Ser. No. 10-2019-7005015 dated Nov. 30, 2021, with English Translation (7 pages).
MY Office Action on MY Appl. Ser. No. PI2019000673 dated Feb. 3, 2022 (3 pages).
Ogawa et al., "A novel insertional mutation at the third zinc finger coding region of the WT1 gene in Denys-Drash syndrome," Human Molecular Genetics, Feb. 1993, vol. 2 (pp. 203-204).
Provasi et al., "Editing T cell specificity towards leukemia by zinc finger nucleases and lentiviral gene transfer," Nature Medicine, May 2012, vol. 18, No. 5 (pp. 807-815).
Rebar, et al., "New Zinc Finger Nuclease Architectures for Highly Efficient Genome Engineering in Primary Cells at Large Scale with No Detectable Off-Target Effects," Molecular Therapy, vol. 25 (2017) pp. 11-12.
SG Office Action on SG Appl. Ser. No. 11201901531T dated Dec. 30, 2020 (6 pages).
Takasu et al., "Efficient TALEN Construction for Bombyx mori Gene Targeting," PloS One, Sep. 18, 2013, vol. 8, No. 9 (pp. 1-11).
Tasan et al., "Use of genome-editing tools to treat sickle cell disease," Human Genetics, Springer, (2016) vol. 135, No. 9 (pp. 1011-1028).
TW Notice of Allowance on TW Appl. Ser. No. 106129809 dated Nov. 17, 2021, with English Translation (3 pages).
TW Search Report on TW Appl. Ser. No. 106129809 dated Nov. 11, 2021, no translation (1 page).
UniProt Accession No. A0A0F2J3F6, Type II restriction endonuclease, created Jun. 24, 2015. https://www.uniprot.org/uniproUAOAOF2J3F6.txt, Oct. 20, 2019, (1 page).
UniProt Accession No. A0A0F2J3F6, Type II restriction endonuclease, created Jun. 24, 2015 (2 pages).
Urnov et al., "Genome Editing with Engineered Zinc Finger Nucleases," Nature Reviews Genetics, Sep. 2010, vol. 11, No. 9 (pp. 636-646).
US Final Office Action on U.S. Appl. No. 16/281,751 dated Sep. 6, 2019 (21 pages).
US Non-Final Office Action on U.S. Appl. No. 16/281,751 dated May 15, 2019 (20 pages).
US Notice of Allowance on U.S. Appl. No. 16/281,751 dated Oct. 8, 2019 (9 pages).
VN Office Action on VN Appl. Ser. No. 1201900949 dated Nov. 29, 2021, with English Translation (4 pages).
Wah et al., "Structure of FokI has implications for DNA cleavage," Proceedings of the National Academy of Sciences USA, Sep. 1998, vol. 95, No. 18 (pp. 10564-10569).
Waugh et al., "A novel class of FokI restriction endonuclease mutants that cleave hemi-methylated substrates," Journal of Biological Chemistry (1994) vol. 269 No. 16 (pp. 12298-12303).
Whisstock et al., "Prediction of protein function from protein sequence and structure," Quarterly Reviews of Biophysics (2003) vol. 36 No. 3 (pp. 307-340).
Witowski, et al., "Conversion of b-ketoacyl synthase to a Malonyl Decarboxylase by replacement of the active cysteine with glutamine," Biochemistry (1999) vol. 38 (pp. 11643-11650).
Zhang, et al., "C-terminal in Sp1-like artificial zinc-finger proteins plays crucial roles in determining their DNA binding affinity", BMC Biotechnology (2013) vol. 11, Issue 106 (pp. 1-8).
Bu Yuling, et al., "Artificial Zinc Finger Nuclease Mediates Cellular Level TMEM18 Knockdown and its Functional Analysis", China Master's These Full-text Database (Electronic journal): Medicine and Health Section, No. 6, Jun. 15, 2017, pp. E065-82.
Gao Yang, "CRISPR/Cas9-mediated of BCL11A gene editing in CD34+ hematopoietic stem cells increases Hbf expression", China Doctoral Dissertation Full Text Database (Electronic Journal) Medicine and Health Science and Technology Series, No. 11, Nov. 15, 2017, E062-120.
Kugler, S. et al., "CatD_ZFN1 [synthetic Construct]", GenBank Database, Jun. 19, 2017, Accession No. 1: AS A39894.1.
Liang Hao, et al., "Progress in Gene Therapy of Sickle Cell Disease Based on hemoglobin F", Journal of Experimental Hematology, vol. 29, No. 2, May 13, 2021, pp. 643-647.
Miller, et al., "An improved zinc-finger nuclease architecture for highly specific genome editing," Nature Biotechnology, Jul. 2007, vol. 25, No. 7 (pp. 778-785).
Wang Ling, et al., "Application of Zinc Finger Nucleases in Genome Targeting Modification", Chinese Journal of Biochemistry and Molecular Biology, vol. 25, No. 7, Jul. 20, 2009, pp. 585-589.
Zahur, et al., "Long-term Assessment of AAV-Mediated Zinc Finger Nuclease Expression in the Mouse Brain", Frontiers in Molecular Neuroscience, May 2017, vol. 10, Article 142, pp. 1-13.
Elrod-Erickson and Pabo, "Binding Studies with Mutants of Zif268," The Journal of Biological Chemistry, Jul. 2, 1999, vol. 274 No., 27 (pp. 19281-19285).

* cited by examiner

FIG. 2

| CHROMOSOME | BASE # | INTEGRANT COUNT |
|---|---|---|
| 2 | 60495266 | 1064 |
| 8 | 119856442 | 939 |
| 2 | 62164814 | 156 |
| 10 | 132654828 | 105 |
| 14 | 67422056 | 102 |
| 4 | 7829724 | 93 |
| 2 | 237702832 | 88 |
| 14 | 73740920 | 85 |
| 1 | 291826166 | 82 |
| 10 | 69571176 | 75 |
| 16 | 151141540 | 68 |
| 8 | 94988042 | 66 |
| 16 | 2122340 | 66 |
| 16 | 45406680 | 64 |
| 19 | 67184172 | 59 |
| 16 | 46394744 | 58 |
| 13 | 75549350 | 57 |
| 16 | 34593646 | 57 |
| 16 | 46390726 | 54 |
| 1 | 54506814 | 53 |
| 19 | 55115766 | 53 |
| 6 | 538805956 | 52 |
| 17 | 29624234 | 52 |
| 1 | 26938300 | 48 |
| 5 | 145864942 | 40 |
| 20 | 37707466 | 39 |
| 21 | 33308800 | 36 |
| 1 | 204975770 | 35 |
| 5 | 132776212 | 35 |
| 11 | 33894468 | 34 |
| 10 | 101133378 | 33 |
| 17 | 28854518 | 33 |
| X | 302880458 | 31 |
| 2 | 844459580 | 30 |
| 7 | 1315033656 | 30 |
| 2 | 112583534 | 27 |
| 3 | 49724756 | 27 |
| 12 | 55928112 | 27 |

BCL11A →

| CHROMOSOME | BASE # | INTEGRANT COUNT |
|---|---|---|
| 22 | 20508058 | 15 |
| 1 | 167637598 | 14 |
| 9 | 211655462 | 14 |
| 16 | 129611194 | 14 |
| 19 | 46399310 | 14 |
| 14 | 38665086 | 14 |
| 14 | 50504 | 14 |
| 2 | 96873178 | 13 |
| 2 | 107763998 | 13 |
| 2 | 127820122 | 13 |
| 6 | 1596312 | 13 |
| 6 | 354680034 | 13 |
| 6 | 144064118 | 13 |
| 8 | 107386748 | 13 |
| 10 | 98910092 | 13 |
| 12 | 104048816 | 13 |
| 14 | 89466992 | 13 |
| 1 | 21635648 | 12 |
| 2 | 135453242 | 12 |
| 6 | 7899998 | 12 |
| 8 | 131105966 | 12 |
| 9 | 128604032 | 12 |
| 11 | 2992880 | 12 |
| 13 | 91576712 | 12 |
| 14 | 18295748 | 12 |
| 16 | 34587146 | 12 |
| 21 | 25607680 | 12 |
| 22 | 15226546 | 12 |
| 1 | 70765014 | 11 |
| 1 | 120942294 | 11 |
| 3 | 200702950 | 11 |
| 5 | 199422238 | 11 |
| 6 | 2057482 | 11 |
| 9 | 3196958 | 11 |
| 11 | 98755462 | 11 |
| 1 | 30406776 | 11 |
| 1 | 177943758 | 10 |

| CHROMOSOME | BASE # | INTEGRANT COUNT |
|---|---|---|
| 17 | 33940450 | 9 |
| 18 | 20578334 | 9 |
| 19 | 850496 | 9 |
| 20 | 29445862 | 8 |
| 1 | 51299472 | 8 |
| 1 | 201507258 | 8 |
| 2 | 16715068 | 8 |
| 2 | 20996616 | 8 |
| 2 | 36785314 | 8 |
| 2 | 226916064 | 8 |
| 2 | 237467876 | 8 |
| 6 | 49519624 | 8 |
| 6 | 160955686 | 8 |
| 10 | 26734304 | 8 |
| 10 | 79114636 | 8 |
| 12 | 50505884 | 8 |
| 14 | 73746866 | 8 |
| 17 | 43805774 | 8 |
| 17 | 82718744 | 8 |
| 18 | 20575274 | 8 |
| 20 | 5788510 | 8 |
| 21 | 25629778 | 8 |
| 22 | 19983370 | 8 |
| X | 47067946 | 7 |
| 1 | 19916860 | 7 |
| 1 | 143187676 | 7 |
| 1 | 148402426 | 7 |
| 2 | 223224616 | 7 |
| 3 | 119198990 | 7 |
| 4 | 45419400 | 7 |
| 4 | 39364694 | 7 |
| 5 | 99547294 | 7 |
| 6 | 38056212 | 7 |
| 6 | 6715482 | 7 |
| 6 | 150090744 | 7 |
| 6 | 899830096 | 7 |
| 7 | 89888012 | 7 |
| | 113383212 | 7 |

| CHROMOSOME | BASE # | INTEGRANT COUNT |
|---|---|---|
| 8 | 66165666 | 26 |
| 11 | 119316888 | 26 |
| X | 134914730 | 26 |
| 8 | 95226212 | 25 |
| 12 | 124995298 | 25 |
| 16 | 10992070 | 25 |
| 3 | 47439806 | 24 |
| 11 | 70518294 | 23 |
| 16 | 10839466 | 22 |
| X | 66004390 | 22 |
| 1 | 9267210 | 21 |
| 9 | 91430052 | 21 |
| 16 | 30692064 | 21 |
| 2 | 155276858 | 20 |
| 16 | 173018750 | 20 |
| 2 | 88559110 | 20 |
| 8 | 149709484 | 19 |
| 13 | 124924782 | 19 |
| 20 | 112237576 | 19 |
| 7 | 44683654 | 19 |
| 7 | 228965770 | 19 |
| 11 | 13991304 | 18 |
| 12 | 1011110944 | 18 |
| 1 | 108224408 | 18 |
| 1 | 89874464 | 18 |
| 5 | 208159440 | 17 |
| 12 | 150115792 | 16 |
| 15 | 7096136 | 16 |
| 19 | 28018428 | 16 |
| 20 | 1279936 | 16 |
| 1 | 48636010 | 15 |
| 3 | 165379386 | 15 |
| 5 | 711103574 | 15 |
| 7 | 1039618570 | 15 |
| 7 | 128077200 | 15 |
| 8 | 294955584 | 15 |
| 16 | 46399748 | 15 |
| 16 | 57534378 | 15 |

| CHROMOSOME | BASE # | INTEGRANT COUNT |
|---|---|---|
| 2 | 218419648 | 10 |
| 6 | 136793200 | 10 |
| 8 | 259969948 | 10 |
| 10 | 46426956 | 10 |
| 10 | 47957704 | 10 |
| 10 | 52321784 | 10 |
| 10 | 52321864 | 10 |
| 11 | 102685874 | 10 |
| 12 | 54411358 | 10 |
| 12 | 76936636 | 10 |
| 15 | 19782342 | 10 |
| 16 | 152220070 | 10 |
| 16 | 152220090 | 10 |
| 16 | 18131696 | 10 |
| 16 | 18131716 | 10 |
| 18 | 54477734 | 10 |
| 19 | 43779827 | 10 |
| 19 | 51327816 | 10 |
| 21 | 331999996 | 10 |
| 1 | 26569750 | 9 |
| 1 | 577346560 | 9 |
| 3 | 115988958 | 9 |
| 3 | 149636460 | 9 |
| 4 | 519420922 | 9 |
| 4 | 149936952 | 9 |
| 6 | 844258448 | 9 |
| 9 | 138895946 | 9 |
| 9 | 3737388 | 9 |
| 10 | 164378486 | 9 |
| 13 | 93000398 | 9 |
| 15 | 104239026 | 9 |
| 15 | 67764450 | 9 |
| 15 | 69789200 | 9 |
| 10 | 98822320 | 9 |
| 15 | 31382604 | 9 |
| 15 | 34422898 | 9 |
| 15 | 34569124 | 9 |
| 15 | 78243618 | 9 |

| CHROMOSOME | BASE # | INTEGRANT COUNT |
|---|---|---|
| 8 | 37700430 | 7 |
| 8 | 88289848 | 7 |
| 9 | 101660500 | 7 |
| 10 | 112857552 | 7 |
| 10 | 42097318 | 7 |
| 10 | 91591618 | 7 |
| 11 | 120431936 | 7 |
| 12 | 5225468 | 7 |
| 12 | 155086 | 7 |
| 15 | 519951306 | 7 |
| 15 | 64356576 | 7 |
| 16 | 651185434 | 7 |
| 16 | 345730528 | 7 |
| 16 | 464015928 | 7 |
| 17 | 817380622 | 7 |
| 17 | 836804 | 7 |
| 19 | 758145688 | 7 |
| 19 | 17579762 | 7 |
| 19 | 38478442 | 7 |
| 20 | 40578628 | 7 |
| 22 | 41165952 | 7 |
| 22 | 58585134 | 7 |
| 1 | 36368580 | 6 |
| 1 | 36423722 | 6 |
| 1 | 2914438 | 6 |
| 1 | 91089046 | 6 |
| 2 | 1153285550 | 6 |
| 3 | 1251698466 | 6 |
| 3 | 1251698552 | 6 |
| 3 | 1556106146 | 6 |
| 1 | 1557461944 | 6 |
| 2 | 201664794 | 6 |
| 3 | 131443890 | 6 |
| 3 | 4323698 | 6 |
| 3 | 584148622 | 6 |
| 3 | 661298744 | 6 |
| 3 | 87800708 | 6 |

FIG. 2 (cont.)

| CHROMOSOME | BASE # | INTEGRANT COUNT |
|---|---|---|
| 3 | 141228736 | 6 |
| 4 | 151031930 | 6 |
| 5 | 178121148 | 6 |
| 5 | 289311180 | 6 |
| 6 | 108893514 | 6 |
| 6 | 136088656 | 6 |
| 6 | 163725808 | 6 |
| 7 | 162658 | 6 |
| 7 | 35016604 | 6 |
| 8 | 30408876 | 6 |
| 8 | 91876290 | 6 |
| 8 | 119945566 | 6 |
| 9 | 4090722 | 6 |
| 10 | 104968230 | 6 |
| 11 | 72293352 | 6 |
| 11 | 79866034 | 6 |
| 11 | 118997014 | 6 |
| 12 | 121069264 | 6 |
| 12 | 3073480 | 6 |
| 13 | 26186106 | 6 |
| 13 | 43878548 | 6 |
| 15 | 41284346 | 6 |
| 15 | 58555840 | 6 |
| 16 | 60478340 | 6 |
| 16 | 3106742 | 6 |
| 16 | 4518046 | 6 |
| 16 | 29292606 | 6 |
| 16 | 77989246 | 6 |
| 16 | 88266652 | 6 |
| 16 | 88732066 | 6 |
| 17 | 36938710 | 6 |
| 17 | 267174 | 6 |
| 19 | 39690408 | 6 |
| 22 | 40259106 | 6 |
| X | 40835932 | 6 |
| X | 1724636 | 5 |
| 1 | 6161778 | 5 |
| 1 | 17419988 | 5 |
| 13 | 79775976 | 5 |
| 15 | 40114388 | 5 |
| 15 | 68307028 | 5 |
| 15 | 82539916 | 5 |
| 15 | 86572492 | 5 |
| 16 | 21645824 | 5 |
| 16 | 53042972 | 5 |
| 16 | 58873960 | 5 |
| 16 | 67841642 | 5 |
| 16 | 78808108 | 5 |
| 17 | 17025784 | 5 |
| 17 | 26884866 | 5 |
| 17 | 72902448 | 5 |
| 18 | 11456592 | 5 |
| 18 | 33538826 | 5 |
| 19 | 7159860 | 5 |
| 19 | 11922082 | 5 |
| 19 | 18462114 | 5 |
| 19 | 45686048 | 5 |
| 20 | 29881056 | 5 |
| 20 | 43558622 | 5 |
| 20 | 47575112 | 5 |
| 22 | 19545504 | 5 |
| 22 | 23284226 | 5 |
| 14 | 33684 | 4 |
| 1 | 6359676 | 4 |
| 1 | 185566502 | 4 |
| 1 | 248625744 | 4 |
| 1 | 254442520 | 4 |
| 1 | 30801948 | 4 |
| 1 | 51631166 | 4 |
| 1 | 72774624 | 4 |
| 1 | 109213944 | 4 |
| 1 | 153609522 | 4 |
| 1 | 175878760 | 4 |
| 1 | 201154009 | 4 |
| 1 | 224687886 | 4 |
| 2 | 137774808 | 4 |
| 9 | 92277906 | 4 |
| 9 | 97934932 | 4 |
| 9 | 121566378 | 4 |
| 9 | 124392210 | 4 |
| 9 | 126591182 | 4 |
| 9 | 138212048 | 4 |
| 10 | 25357460 | 4 |
| 10 | 41847448 | 4 |
| 10 | 41847504 | 4 |
| 10 | 42103514 | 4 |
| 10 | 64508254 | 4 |
| 10 | 76825618 | 4 |
| 10 | 109893420 | 4 |
| 11 | 35944902 | 4 |
| 11 | 72431102 | 4 |
| 12 | 6232920 | 4 |
| 12 | 7242432 | 4 |
| 12 | 49404046 | 4 |
| 12 | 75511410 | 4 |
| 12 | 88031364 | 4 |
| 12 | 95073610 | 4 |
| 13 | 113153372 | 4 |
| 13 | 18964478 | 4 |
| 13 | 34779902 | 4 |
| 13 | 113600728 | 4 |
| 14 | 92616966 | 4 |
| 15 | 33229354 | 4 |
| 15 | 64142544 | 4 |
| 15 | 67498752 | 4 |
| 15 | 753356538 | 4 |
| 15 | 76355710 | 4 |
| 15 | 684294 | 4 |
| 15 | 14285910 | 4 |
| 15 | 85317250 | 4 |
| 17 | 9710280 | 4 |
| 17 | 21372082 | 4 |
| 17 | 21906776 | 4 |
| 17 | 26603948 | 4 |

FIG. 2 (cont.)

| CHROMOSOME | BASE # | INTEGRANT COUNT |
|---|---|---|
| 1 | 36401004 | 5 |
| 1 | 143208542 | 5 |
| 1 | 150528982 | 5 |
| 1 | 154750274 | 5 |
| 2 | 86563402 | 5 |
| 2 | 105038552 | 5 |
| 2 | 117954094 | 5 |
| 2 | 130230372 | 5 |
| 2 | 176188548 | 5 |
| 3 | 2041446 | 5 |
| 3 | 16078092 | 5 |
| 3 | 75669968 | 5 |
| 3 | 178998880 | 5 |
| 3 | 184689238 | 5 |
| 4 | 49119414 | 5 |
| 4 | 73573948 | 5 |
| 4 | 78700116 | 5 |
| 5 | 7057496 | 5 |
| 5 | 11767140 | 5 |
| 5 | 56314802 | 5 |
| 5 | 132314286 | 5 |
| 6 | 58116958 | 5 |
| 6 | 60870558 | 5 |
| 7 | 128792974 | 5 |
| 7 | 133081754 | 5 |
| 9 | 92835866 | 5 |
| 9 | 131373156 | 5 |
| 10 | 50701042 | 5 |
| 11 | 87382350 | 5 |
| 11 | 49652236 | 5 |
| 11 | 61612468 | 5 |
| 11 | 62795536 | 5 |
| 11 | 67277754 | 5 |
| 11 | 82032970 | 5 |
| 11 | 88966978 | 5 |
| 12 | 6326346 | 5 |
| 12 | 104138422 | 5 |
| 12 | 121500124 | 5 |

| CHROMOSOME | BASE # | INTEGRANT COUNT |
|---|---|---|
| 2 | 166910124 | 4 |
| 2 | 234668446 | 4 |
| 3 | 49802584 | 4 |
| 3 | 195856500 | 4 |
| 3 | 198148214 | 4 |
| 4 | 1686620 | 4 |
| 4 | 3480800 | 4 |
| 4 | 99869180 | 4 |
| 4 | 138090616 | 4 |
| 4 | 158876704 | 4 |
| 5 | 107727038 | 4 |
| 5 | 36318878 | 4 |
| 5 | 36322678 | 4 |
| 5 | 65562414 | 4 |
| 5 | 100709408 | 4 |
| 5 | 142193948 | 4 |
| 5 | 149564992 | 4 |
| 6 | 164896712 | 4 |
| 6 | 176740968 | 4 |
| 6 | 26443624 | 4 |
| 6 | 27782516 | 4 |
| 6 | 45156450 | 4 |
| 6 | 146750040 | 4 |
| 7 | 169090710 | 4 |
| 7 | 1214740 | 4 |
| 7 | 373573450 | 4 |
| 7 | 373574520 | 4 |
| 7 | 62355868 | 4 |
| 8 | 71679460 | 4 |
| 8 | 106778616 | 4 |
| 8 | 133077880 | 4 |
| 8 | 5753270 | 4 |
| 8 | 5753290 | 4 |
| 8 | 82445554 | 4 |
| 8 | 8371950 | 4 |
| 8 | 101955394 | 4 |
| 8 | 119000446 | 4 |
| 9 | 38068006 | 4 |

| CHROMOSOME | BASE # | INTEGRANT COUNT |
|---|---|---|
| 17 | 26603992 | 4 |
| 17 | 40557500 | 4 |
| 17 | 43796376 | 4 |
| 17 | 49883740 | 4 |
| 18 | 132272880 | 4 |
| 18 | 30136646 | 4 |
| 18 | 30845084 | 4 |
| 18 | 74019902 | 4 |
| 19 | 40266218 | 4 |
| 19 | 42741976 | 4 |
| 19 | 42767202 | 4 |
| 19 | 42881190 | 4 |
| 19 | 49683046 | 4 |
| 20 | 4673782 | 4 |
| 20 | 24683868 | 4 |
| 20 | 44911634 | 4 |
| 20 | 48621130 | 4 |
| 20 | 49279476 | 4 |
| 20 | 49699412 | 4 |
| 20 | 56914278 | 4 |
| 20 | 62819166 | 4 |
| 21 | 10442640 | 4 |
| 22 | 22533154 | 4 |
| 22 | 22648222 | 4 |
| 22 | 22956152 | 4 |
| 22 | 23111094 | 4 |
| 22 | 23162790 | 4 |
| 22 | 246629320 | 4 |
| 22 | 321360744 | 4 |
| 22 | 452165266 | 4 |
| X | 61346666 | 4 |
| X | 396888532 | 4 |
| X | 529347300 | 4 |
| X | 712831922 | 4 |
| X | 903236788 | 4 |
| X | 1068632788 | 4 |
| Y | 3900438 | 4 |

FIG. 2 (cont.)

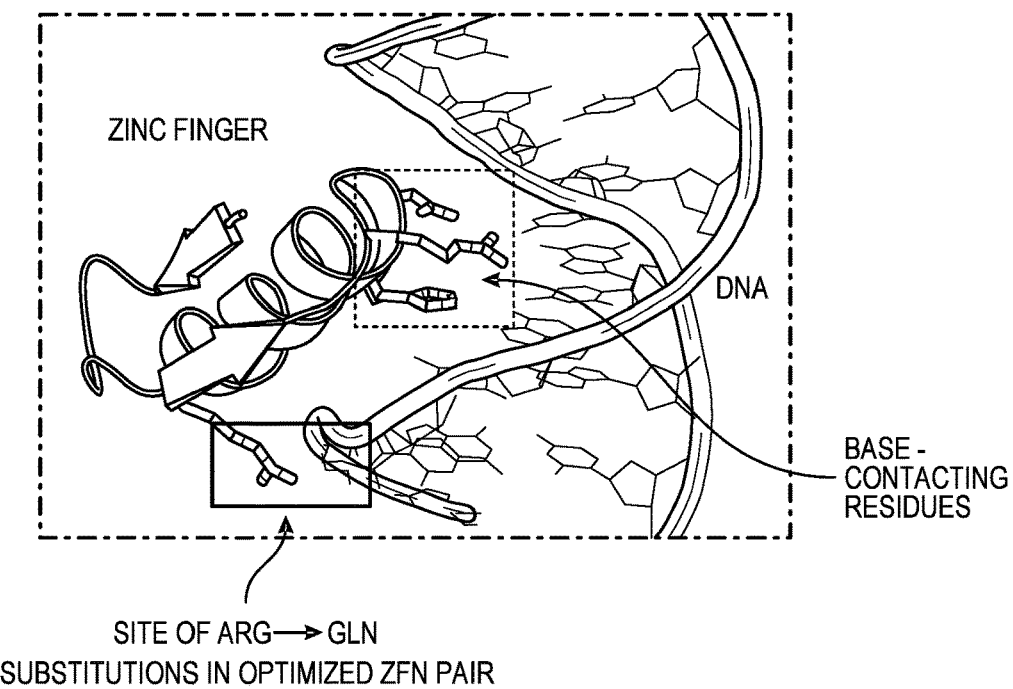

SITE OF ARG → GLN
SUBSTITUTIONS IN OPTIMIZED ZFN PAIR

FIG. 3A

| | | | SITE OF ARG SUBSTITUTIONS IN OPTIMIZED ZFN PAIR | GLN | | BASE-CONTACTING RESIDUES | |
|---|---|---|---|---|---|---|---|
| LEFT ZFP | F1 | VPAAMAERP | FQCRICMRNF | S | DQSN L RA HIRTH | |
| | F2 | TGEKP | FACDICGRKF | A | RNFS L TM HTKIH | |
| | F3 | TGSQKP | FQCRICMRNF | S | STGN L TN HIRTH | |
| | F4 | TGEKP | FACDICGRKF | A | TSGS L TR HTKIH | |
| | F5 | THPRAPIPKP | FQCRICMRNF | S | DQSN L RA HIRTH | |
| | F6 | TGEKP | FACDICGRKF | A | AQCC L FH HTKIH | LRGS |
| RIGHT ZFP | F1 | VPAAMAERP | FQCRICMRNF | A | RNDH R TH HTKIH | |
| | F2 | TGEKP | FQCRICMRNF | S | QKAH L IR HIRTH | |
| | F3 | TGEKP | FACDICGRKF | A | QKGT L GE HTKIH | |
| | F4 | TGSQKP | FQCRICMRNF | S | RGRD L SR HIRTH | |
| | F5 | TGEKP | FACDICGRKF | A | RRDN L HS HTKIH | LRGS |

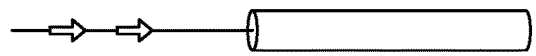

FIG. 3B

REGULATION OF GENE EXPRESSION USING ENGINEERED NUCLEASES

CROSS-REFERENCE TO RELATED APPLICATIONS

This application is a continuation of U.S. patent application Ser. No. 16/281,751, filed Feb. 21, 2019, which is a continuation of PCT/US2017/048397, filed Aug. 24, 2017, which claims the benefit of U.S. Provisional Application No. 62/378,978, filed Aug. 24, 2016; U.S. Provisional Application No. 62/443,981, filed Jan. 9, 2017; and U.S. Provisional Application No. 62/545,778, filed Aug. 15, 2017, the disclosures of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Jan. 6, 2019, is named 8328-0163-01_SL.txt and is 29,435 bytes in size.

TECHNICAL FIELD

The present disclosure is in the field of genome engineering, particularly targeted modification of the genome of a hematopoietic cell.

BACKGROUND

When one considers that genome sequencing efforts have revealed that the human genome contains between 20,000 and 25,000 genes, but fewer than 2000 transcriptional regulators, it becomes clear that a number of factors must interact to control gene expression in all its various temporal, developmental and tissue specific manifestations. Expression of genes is controlled by a highly complex mixture of general and specific transcriptional regulators that interact with DNA elements. These DNA elements comprise both local DNA elements such as the core promoter and its associated transcription factor binding sites as well as distal elements such as enhancers, silencers, insulators and locus control regions (LCRs) (see Matson et al. (2006) *Ann Rev Genome Hum Genet* 7: 29-59).

Enhancer elements were first identified in the SV40 viral genome, and then found in the human immunoglobulin heavy chain locus. Now known to play regulatory roles in the expression of many genes, enhancers appear to mainly influence temporal and spatial patterns of gene expression. It has also been found that enhancers can function to regulate expression at large distances from the core promoter of the targeted gene, and are not dependent on any specific sequence orientation with respect to the promoter. Enhancers can be located several hundred kilobases upstream or downstream of a core promoter region, where they can be located in an intron sequence, or even beyond the 3' end of a gene.

Various methods and compositions for targeted cleavage of genomic DNA have been described. Such targeted cleavage events can be used, for example, to induce targeted mutagenesis, induce targeted deletions of cellular DNA sequences, and facilitate targeted recombination at a predetermined chromosomal locus. See, e.g., U.S. Pat. Nos. 9,255,250; 9,200,266; 9,045,763; 9,005,973; 9,150,847; 8,956,828; 8,945,868; 8,703,489; 8,586,526; 6,534,261; 6,599,692; 6,503,717; 6,689,558; 7,067,317; 7,262,054; 7,888,121; 7,972,854; 7,914,796; 7,951,925; 8,110,379; 8,409,861; U.S. Patent Publication Nos. 2003/0232410; 2005/0208489; 2005/0026157; 2005/0064474; 2006/0063231; 2008/0159996; 2010/00218264; 2012/0017290; 2011/0265198; 2013/0137104; 2013/0122591; 2013/0177983; 2013/0196373; 2015/0056705 and 2015/0335708, the disclosures of which are incorporated by reference in their entireties.

These methods often involve the use of engineered cleavage systems to induce a double strand break (DSB) or a nick in a target DNA sequence such that repair of the break by an error born process such as non-homologous end joining (NHEJ), non-homology directed end capture of donors or repair using a repair template (homology directed repair or HDR) can result in the knock out of a gene or the insertion of a sequence of interest (targeted integration). See, e.g., U.S. Pat. Nos. 9,045,763; 9,200,266; 9,005,973; and 8,703,489. These techniques can also be used to introduce site specific changes in the genome sequence through use of a donor oligonucleotide, including the introduction of specific deletions of genomic regions, or of specific point mutations or localized alterations (also known as gene correction). Cleavage can occur through the use of specific nucleases such as engineered zinc finger nucleases (ZFN), transcription-activator like effector nucleases (TALENs), or using the CRISPR/Cas system with an engineered crRNA/tracr RNA ('single guide RNA') to guide specific cleavage. Further, targeted nucleases are being developed based on the Argonaute system (e.g., from *T. thermophilus*, known as 'TtAgo', see Swarts et al. (2014) *Nature* 507(7491): 258-261), which also may have the potential for uses in genome editing and gene therapy.

Red blood cells (RBCs), or erythrocytes, are the major cellular component of blood and account for one quarter of the cells in a human. Mature RBCs lack a nucleus and many other organelles and are full of hemoglobin, a metalloprotein that functions to carry oxygen from the lungs to the tissues as well as carry carbon dioxide out of the tissues and back to the lungs for removal. This protein makes up approximately 97% of the dry weight of RBCs and it increases the oxygen carrying ability of blood by about seventy-fold. Hemoglobin is a heterotetramer comprising two alpha (α)-like globin chains and two beta (β)-like globin chains and 4 heme groups. In adults, the α2β2 tetramer is referred to as Hemoglobin A (HbA) or adult hemoglobin. Typically, the alpha and beta globin chains are synthesized in an approximate 1:1 ratio and this ratio seems to be critical in terms of hemoglobin and RBC stabilization. In a developing fetus, a different form of hemoglobin, fetal hemoglobin (HbF), is produced which has a higher binding affinity for oxygen than Hemoglobin A such that oxygen can be delivered to the baby's system via the mother's blood stream. There are two genes that encode fetal globin that are very similar in sequence and are termed HBG1 (also referred to as Ggamma) and HBG2 (Agamma), based on their order of arrangement in the beta globin gene locus. Like adult hemoglobin, fetal hemoglobin protein contains two a globin chains, but in place of the adult β-globin chains, it has two fetal gamma (γ)-globin chains (i.e., fetal hemoglobin is α2γ2). At approximately 30 weeks of gestation, the synthesis of gamma globin in the fetus starts to drop, while the production of beta globin increases. By approximately 10 months of age, the newborn's hemoglobin is nearly all α2β2 although some HbF persists into adulthood (approximately 1-3% of total hemoglobin). The regulation of the switch from production of gamma- to beta-globin is quite complex, and primarily involves a down-regulation of gamma globin transcription with a simultaneous up-regulation of beta globin transcription.

Genetic defects in the sequences encoding the hemoglobin chains can be responsible for a group of diseases known as hemoglobinopathies that include sickle cell anemia and the alpha and beta thalassemias. In the majority of patients with hemoglobinopathies, the genes encoding gamma globin remain present, but expression is relatively low due to normal gene repression occurring around parturition as described above.

It is estimated that 1 in 5000 people in the U.S. have sickle cell disease (SCD), mostly in people of sub-Saharan Africa descent (Roseff (2009) *Immunohematology* 25(2):67) There appears to be a benefit for heterozygous carriers of the sickle cell mutation due to protection against malaria, so this trait may have been positively selected over time, such that it is estimated that in sub-Saharan Africa, up to 28% of the population has the sickle cell trait (Elguero et al. (2015) *PNAS USA* 112 (22): 7051). Sickle cell disease is caused by a mutation in the β globin gene as a consequence of a valine substitution for glutamic acid at amino acid #6 (a GAG to GTG mutation at the DNA level), where the resultant hemoglobin is referred to as "hemoglobin S" or "HbS." Under lower oxygen conditions, a conformational shift in the deoxy form of HbS exposes a hydrophobic patch on the protein between the E and F helices. The hydrophobic residues of the valine at position 6 of the beta chain in hemoglobin are able to associate with the hydrophobic patch, causing HbS molecules to aggregate and form fibrous precipitates. These aggregates in turn cause the abnormality or 'sickling' of the RBCs, resulting in a loss of cell flexibility. The sickling RBCs are no longer able to squeeze into the capillary beds and can result in vaso-occlusive crisis in sickle cell patients. In addition, sickled RBCs are more fragile than normal RBCs, and tend towards hemolysis, eventually leading to anemia in the patient.

Treatment and management of sickle cell patients is a life-long proposition involving antibiotic treatment, pain management and transfusions during acute episodes. One approach is the use of hydroxyurea, which exerts its effects in part by increasing the production of gamma globin. Long term side effects of chronic hydroxyurea therapy are still unknown, however, and treatment gives unwanted side effects that lead to low patient compliance, and has variable efficacy from patient to patient (Brandow and Panepinto (2011) *Am J Hematol* 86(9):804-806). Despite an increase in the efficacy of sickle cell treatments, the life expectancy of patients is still only in the mid to late 50's and the associated morbidities of the disease have a profound impact on a patient's quality of life.

Thalassemias are also diseases relating to hemoglobin and typically involve a reduced expression of globin chains. This can occur through mutations in the regulatory regions of the genes or from a mutation in a globin coding sequence that results in reduced expression or reduced levels or functional globin protein. Alpha thalassemias, caused by mutations in the alpha globin locus, are mainly associated with people of Western Africa and South Asian descent, and may confer malarial resistance. Beta thalassemia, caused by mutations in the beta globin locus, is mainly associated with people of Mediterranean descent, typically from Greece and the coastal areas of Turkey and Italy. In thalassemia minor, only one of the β globin alleles bears a mutation. Individuals will suffer from microcytic anemia, and detection usually involves lower than normal mean corpuscular volume (<80 fL). The alleles of subjects with thalassemia minor are β+/β or β0/β (where 'β+' refers to alleles that allow some amount of β chain formation to occur, 'β' refers to wild type β globin alleles, and 'β0' refers to β globin mutations associated with a complete absence of beta-globin expression). Thalassemia intermedia subjects can often manage a normal life but may need occasional transfusions, especially at times of illness or pregnancy, depending on the severity of their anemia. These patient's alleles can be β+/β+ or β0/β+. Thalassemia major occurs when both alleles have thalassemia mutations. This is severely microcytic and hypochromic anemia. Untreated, it causes anemia, splenomegaly and severe bone deformities and progresses to death before age 20. Treatment consists of periodic blood transfusion; splenectomy for splenomegaly and chelation of transfusion-caused iron overload. Bone marrow transplants are also being used for treatment of people with severe thalassemias if an appropriate donor can be identified, but this procedure can have significant risks.

One approach that has been proposed for the treatment of both SCD and beta thalassemias is to increase the expression of gamma globin with the aim to have HbF functionally replace the aberrant adult hemoglobin. As mentioned above, treatment of SCD patients with hydroxyurea is thought to be successful in part due to its effect on increasing gamma globin expression. The first group of compounds discovered to affect gamma globin expression were cytotoxic drugs. The ability to cause de novo synthesis of gamma-globin by pharmacological manipulation was first shown using 5-azacytidine in experimental animals (DeSimone (1982) *Proc Nat'l Acad Sci USA* 79(14):4428-31). Subsequent studies confirmed the ability of 5-azacytidine to increase HbF in patients with β-thalassemia and sickle cell disease (Ley, et al., (1982) *N. Engl. J. Medicine,* 307: 1469-1475, and Ley, et al., (1983) *Blood* 62: 370-380). In addition, short chain fatty acids (e.g. butyrate and derivatives) have been shown in experimental systems to increase HbF (Constantoulakis et al., (1988) *Blood* 72(6):1961-1967). Also, there is a segment of the human population with a condition known as 'Hereditary Persistence of Fetal Hemoglobin' (HPFH) where elevated amounts of HbF persist in adulthood (10-40% in HPFH heterozygotes (see Thein et al. (2009) *Hum. Mol. Genet* 18 (R2): R216-R223). This is a rare condition, but in the absence of any associated beta globin abnormalities, is not associated with any significant clinical manifestations, even when 100% of the individual's hemoglobin is HbF. When individuals that have a beta thalassemia also have co-incident HPFH, the expression of HbF can lessen the severity of the disease (Potoka and Gladwin (2015) *Am J Physiol Lung Cell Mol Physiol.* 308(4): L314-L324). Further, the severity of the natural course of sickle cell disease can vary significantly from patient to patient, and this variability, in part, can be traced to the fact that some individuals with milder disease express higher levels of HbF.

One approach to increase the expression of HbF involves identification of genes whose products play a role in the regulation of gamma globin expression. One such gene is BCL11A, first identified because of its role in lymphocyte development. BCL11A encodes a zinc finger protein that is thought to be involved in the developmental stage-specific regulation of gamma globin expression. BCL11A is expressed in adult erythroid precursor cells and down-regulation of its expression leads to an increase in gamma globin expression. In addition, the splicing of the BCL11A mRNA is developmentally regulated. In embryonic cells, the shorter BCL11A mRNA variants, known as BCL11A-S and BCL11A-XS are primarily expressed, while in adult cells, the longer BCL11A-L and BCL11A-XL mRNA variants are predominantly expressed. See, Sankaran et al. (2008) *Sci-* ence 322 p. 1839. The BCL11A protein appears to interact with the beta globin locus to alter its conformation and thus its expression at different developmental stages. Use of an inhibitory RNA targeted to the BCL11A gene has been proposed (see, e.g., U.S. Patent Publication No. 2011/0182867) but this technology has several potential drawbacks, namely that complete knock down may not be achieved, delivery of such RNAs may be problematic and the RNAs must be present continuously, requiring multiple treatments for life.

Targeting of BCL11A enhancer sequences provides a mechanism for increasing HbF. See, e.g., U.S. Patent Publication No. 2015/0132269 and PCT Publication No. WO 2016/183298. Genome-wide association studies have identified a set of genetic variations at the BCL11A gene locus that are associated with increased HbF levels. These variations are a collection of small nucleotide polymorphisms (SNP) found in non-coding regions of BCL11A that function as a stage-specific, lineage-restricted enhancer region. Further investigation revealed that this BCL11A enhancer is required in erythroid cells for BCL11A expression, but is not required for its expression in B cells (see Bauer et al. (2013) *Science* 342:253-257). The enhancer region was found within intron 2 of the BCL11A gene, and three areas of DNAseI hypersensitivity (often indicative of a chromatin state that is associated with regulatory potential) in intron 2 were identified. These three areas were identified as "+62", "+58" and "+55" in accordance with the distance in kilobases from the transcription start site of BCL11A. These enhancer regions are roughly 350 (+55); 550 (+58); and 350 (+62) nucleotides in length (Bauer 2013, ibid).

When developing a nuclease for use in therapeutic treatments of humans, it is essential that the nuclease have the utmost safety characteristics. Specifically, the nucleases must have very low levels of off-target cleavage. Significant numbers of double strand cuts in locations other than the user-specified target can lead to repression of off-target genes, and in rare instances, the occurrence of chromosomal translocations (see Hoban and Bauer (2016) *Blood* 127(21): 2525-2535 and Schaefer et al. (2017) *Nature Methods* 14(6):547-548, in press). Improvements in specificity can be achieved by eliminating non-specific interactions between the engineered nuclease and the genomic DNA (see U.S. Provisional Patent Application Nos. 62/378,978 and 62/443,981).

Thus, there remains a need for additional highly specific methods and compositions for the alteration of BCL11A gene expression, for example to treat hemoglobinopathies such as sickle cell disease and beta thalassemia.

SUMMARY

The present invention describes highly specific compositions and methods for use in gene therapy and genome engineering. Specifically, the methods and compositions described relate to inactivating (e.g., by completely or partially abolishing its expression) a BCL11A gene, for example, a gene that acts as regulator of one or more additional genes. In particular, the invention describes methods and compositions for interfering with enhancer function in a BCL11A gene to diminish or knock out its activity in specific cell lineages (e.g., erythroid). Additionally, the invention provides methods and compositions for interfering with BCL11A enhancer functions wherein the enhancer sequences are not located within the coding sequences of the BCL11A gene, and wherein the reagents provided exhibit highly specific activity. The resulting down-regulation of the BCL11A gene in these circumstances results in increased expression of gamma globin, and the number of off-target cleavage events is reduced.

In some aspects, the invention comprises a non-naturally occurring zinc finger protein comprising a zinc finger protein (ZFP) comprising 4, 5 or 6 fingers, each finger comprising a recognition helix region that recognizes a DNA target subsite wherein the recognition helix regions comprise the sequences in the order shown in a single row of Table 1. Within each zinc finger, the 7 amino acid recognition helix region is numbered −1 to +6 within the zinc finger backbone (of approximately 30 residues, including zinc coordinating residues). In certain embodiments, 1, 2, 3 or more of the component zinc fingers of the zinc finger proteins described herein further comprise mutations to one or more residues outside the recognition helix region, including but not limited to mutations to amino acids at position −5, position −14 or at both positions −5 and −14 (numbering continuing from the −1 to +6 numbering used for the recognition helix region) are mutated. See, e.g., Qm4 and Qm14 mutations described in U.S. Provisional Patent Applications 62/378,978 and 62/443,981. The component zinc fingers of the zinc finger protein can be linked by any linkers, for example as described in U.S. Pat. No. 8,772,453. In certain embodiments, the ZFP comprises the recognition helixes as shown in Table 1 for the proteins designated as follows: 63014 (which binds to the target site shown in SEQ ID NO:1) and 65722 (which binds to the target site shown in SEQ ID NO:2).

In certain embodiments, the zinc finger proteins as described herein are fused to a functional domain (e.g., transcriptional activation domain, transcriptional repression domain, cleavage domain (to form a zinc finger nuclease), etc.). Any linker may be used to operably link the cleavage domain and the zinc finger protein, including but not limited to linkers as described in U.S. Pat. Nos. 9,394,531 and 9,567,609. Furthermore, when a FokI cleavage domain is used, further mutations in the catalytic domain, dimerization domain, to phosphate contact residues (not in the dimerization or catalytic domain), and combinations of mutations in any one of the catalytic domain, dimerization domain and to phosphate contact residues may be present, including but not limited to ELD or KKR mutations to the dimerization domain, mutations to residues 525 (K to S) of the FokI domain, and combinations of ELD or KKR mutations to the dimerization domain and mutations to residues 525 (K to S) of the FokI domain, numbered relative to wild-type. See, U.S. Pat. Nos. 7,888,121; 7,914,796; 8,034,598; 8,623,618 and U.S. Patent Publication No. 2011/0201055 and U.S. Provisional Patent Application Nos. 62/378,978 and 62/443,981.

In certain embodiments, zinc finger nucleases (ZFNs) may be used in dimerizing pairs to cleave at or near one or both of the target sites for the ZFNs of the pair, for example, the "left partner" of Table 1 (e.g., 63014) can form a dimer with the "right partner" of Table 1 (e.g., 65722) to cleave BCL11A enhancer sequences. In certain embodiments, the pair of ZFNs comprises the following amino acid sequences:

63014:
(SEQ ID NO: 3)
MDYKDHDGDYKDHDIDNIKDDDDKMAPKKKRKVGIHGVPAAMAERPFQCR

ICMQNFSDQSNLRAHIRTHTGEKPFACDICGRKFARNFSLTMHTKIHTGS

-continued

QKPFICMQNFSSTGNLTNHIRTHTGEKPFACDICGRKFATSGSLTRHTKI

HTHPRAPIPKPFQCRICMQNFSDQSNLRAHIRTHTGEKPFACDICGRKFA

AQCCLFHHTKIH-Linker-

ELEEKKSELRHKLKYVPHEYIELIEIARNSTQDRILEMKVMEFFMKVYGY

RGKHLGGSRKPDGAIYTVGSPIDYGVIVDTKAYSGGYNLPIGQADEMERY

VEENQTRDKHLNPNEWWKVYPSSVTEFKFLFVSGHFKGNYKAQLTRLNHI

TNCNGAVLSVEELLIGGEMIKAGTLTLEEVRRKFNNGEINFRS;
and (SEQ ID NO: 4)
MDYKDHDGDYKDHDIDYKDDDDKMAPKKKRKVGIHGVPAAMAERPFQCRI

CMQKFARNDHRTTHTKIHTGEKPFQCRICMQNFSQKAHLIRHIRTHTGEK

PFACDICGRKFAQKGTLGEHTKTHTGSQKPFQCRICMQNFSRGRDLSRHI

RTHTGEKPFACDICGRKFARRDNLHSHTKIH-Linker-

ELEEKKSELRHKLKYVPHEYIELIEIARNSTQDRILEMKVMEFFMKVYGY

RGKHLGGSRKPDGAIYTVGSPIDYGVIVDTKAYSGGYNLPIGQADEMQRY

VKENQTRNKHINPNEWWKVYPSSVTEFKFLFVSGHFSGNYKAQLTRLNRK

TNCNGAVLSVEELLIGGEMIKAGTLTLEEVRRKFNNGEINF, wherein the Linker sequence can be any linker sequence known in the art, for example as described in U.S. Pat. Nos. 9,394,531 and 9,567,609. In certain embodiments, the linker for 63014 comprises or consists of the L7c5 linker (LRGSISRARPLNPHP (SEQ ID NO:5)) and the linker used in 65722 comprises or consists of the L0 linker (LRGSQLVKS (SEQ ID NO:6), see U.S. Pat. No. 9,567,609). The FokI cleavage domain sequence C-terminal to the Linker of the sequences shown above may also comprise alternative FokI domains operably linked to the zinc finger protein. In certain embodiments, the FokI cleavage domain may include alternate or additional mutations to the catalytic domain, the dimerization domain, phosphate contact residues, and combinations of mutations to any one of the catalytic domain, dimerization domain and phosphate contact residues.

In another aspect, the invention comprises delivery of at least one nuclease (e.g., a nuclease that binds to a BCL11A enhancer sequence) to a human stem cell or precursor cell (HSC/PC) for the purpose of genome engineering. In certain embodiments, the nuclease comprises a zinc finger protein (ZFP) comprising 4, 5 or 6 fingers, each finger comprising a recognition helix region that recognizes a target subsite wherein the recognition helix regions comprise the sequences in the order shown in a single row of Table 1. In other embodiments, the ZFN nuclease comprises the pair of nucleases designated 63014/65722. The nuclease(s) as described herein may further comprise a linker (e.g., between the DNA-binding domain and the cleavage domain), for example a linker as shown in U.S. Pat. No. 9,567,609, including but not limited to (SEQ ID NO: 5)
LRGSISRARPLNPHP
or (LRGSQLVKS (SEQ ID NO: 6)).

In some embodiments, the nuclease is delivered as a peptide, while in others it is delivered as a nucleic acid encoding the at least one nuclease. In some embodiments, more than one nuclease is used. In some preferred embodiments, the nucleic acid encoding the nuclease is an mRNA, and in some instances, the mRNA is protected. In some aspects, the mRNA may be chemically modified (See e.g. Kormann et al. (2011) Nature Biotechnology 29(2):154-157). In other aspects, the mRNA may comprise an ARCA cap (see U.S. Pat. Nos. 7,074,596 and 8,153,773). In further embodiments, the mRNA may comprise a mixture of unmodified and modified nucleotides (see U.S. Patent Publication No. 2012/0195936). In a preferred embodiment, the nucleic acid encoding the nuclease(s) is delivered to the HSC/PC via electroporation. In some embodiments, the nuclease cleaves at or near the binding site of a transcription factor. In some aspects, the transcription factor is GATA-1.

In other aspects, the invention comprises a cell or cell line in which an endogenous BCL11A enhancer sequence is genetically modified by a nuclease as described herein (e.g., shown in Table 1), for example as compared to the wild-type sequence of the cell. The genetic modification to the BCL11A enhancer results in modification of globin (beta and gamma) gene expression. Nuclease-modified cells or cell lines as described herein are distinguishable in structure, function, and combinations of both structure and function from wild-type. The genetically modified cell or cell lines may be heterozygous or homozygous for the modification. The modifications may comprise insertions (e.g., transgene insertion) deletions, and combinations of insertions and deletions; such insertions, deletions, and combinations of insertions and deletions are commonly referred to as "indels". In some preferred embodiments, indels result in the destruction of a transcription factor binding site. In certain embodiments, the modification is at or near the nuclease(s) binding site(s), cleavage site(s), and combinations of binding and cleavage sites, for example, within 1-300 (or any value therebetween) base pairs upstream or downstream of the site(s) of cleavage, more preferably within 1-100 base pairs (or any value therebetween) of either side of the binding site(s), cleavage site(s), and combinations of binding and cleavage sites shown in Table 1, even more preferably within 1 to 50 base pairs (or any value therebetween) on either side of the binding site(s), cleavage site(s), and combinations of binding and cleavage sites. In certain embodiments, the genetic modification of the BCL11A enhancer sequence is within and/or between sequences shown in Table 1 (target sites). The modification may also include modifications to one or more nucleotides in the cleavage sites. The modification may also include modifications to one or more nucleotides in the binding sites. The modification may further include modifications to one or more nucleotides in the cleavage sites, and in one or more of the binding sites. In certain embodiments, one or more of the nuclease target site(s) is(are) not modified. In other embodiments, at least one of the target sites for the nuclease(s) is(are) modified. In certain embodiments, the modification is at or near the "+58" region of the BCL11A enhancer, for example, at or near a nuclease binding site shown in any of SEQ ID NO:1 and SEQ ID NO:2. Any cell or cell line may be modified by the nucleases as described herein, for example a stem cell (hematopoietic stem cell such as a CD34+ hematopoietic stem cell) or red blood cell (RBC) precursor cell.

Also described are cells or cell lines obtained following modification by a nuclease as described herein, for example cells or cell lines descended from a nuclease-modified cell or cell line as described herein. Partially or fully differentiated cells descended from the modified stem cells as described herein are also provided (e.g., RBCs or RBC precursor cells). The cells descended from the nuclease-modified cells may be propagated, differentiated, and combinations of both propagated and differentiated in vitro (culture) or may differentiate within a live subject, for example following ex vivo administration of a nuclease-modified stem cell. Any of the genetically modified cells or cell lines disclosed herein may show increased expression of gamma globin. Compositions such as pharmaceutical compositions comprising the genetically modified cells as described herein are also provided.

In other aspects, the invention comprises delivery of a donor nucleic acid to a target cell to provide a genetically modified cell in which the donor is integrated into the cell. The donor may be delivered prior to, after, or along with the nucleic acid encoding the nuclease(s) of Table 1. The donor nucleic acid may comprise an exogenous sequence (transgene) to be integrated into the genome of the cell, for example, an endogenous locus. In some embodiments, the donor may comprise a full-length gene or fragment thereof flanked by regions of homology with the targeted cleavage site. In some embodiments, the donor lacks homologous regions and is integrated into a target locus through homology independent mechanism (i.e. NHEJ). The donor may comprise any nucleic acid sequence, for example a nucleic acid that, when used as a substrate for homology-directed repair of the nuclease-induced double-strand break, leads to a donor-specified deletion to be generated at the endogenous chromosomal locus (e.g., BCL11A enhancer region) or, alternatively (or in addition to), novel allelic forms of (e.g., point mutations that ablate a transcription factor binding site) the endogenous locus to be created. In some aspects, the donor nucleic acid is an oligonucleotide wherein integration leads to a gene correction event, or a targeted deletion.

In other aspects, the nuclease, donor, and combinations of both the nuclease and donor is(are) delivered by viral, non-viral, and combinations of viral and non-viral gene transfer methods. In preferred embodiments, the donor is delivered to the cell via an adeno-associated virus (AAV). In some instances, the AAV comprises LTRs that are of a heterologous serotype in comparison with the capsid serotype.

In some aspects, deletions comprising regions within the DNAseI hypersensitive regions of the enhancer (e.g., the +58 region of the BCL11A enhancer) are made using one or more nucleases as shown in Table 1. These deletions can comprise from about 1 nucleotide to about 551 nucleotides. Thus, the deletions can comprise, 1, 5, 10, 15, 20, 25, 30, 40, 50, 100, 150, 200, 250, 300, 350, 400, 450, 500, 550 nucleotides, or any value therebetween. In some embodiments, the deletions comprise binding regions for one or more transcription factors. In some preferred embodiments, the deletions comprise a GATA-1 binding site, or the binding site for GATA-1 in combination with other factors.

In some embodiments, the DNA binding domains of Table 1 are fused to a functional domain. Some aspects include fusion of the DNA binding domains with domains capable of regulating the expression of a gene. In some embodiments, the fusion proteins comprise the DNA binding domain of Table 1 fused to a gene expression modulatory domain where the modulator represses gene expression.

In some embodiments, the HSC/PC cells are contacted with the nucleases, the DNA binding proteins, and combinations of the nucleases and DNA binding proteins of the invention (i.e., ZFPs as shown in Table 1). In some embodiments, the nucleases, the DNA binding proteins, and combinations of the nucleases and DNA binding proteins are delivered as nucleic acids and in other embodiments, they are delivered as proteins. In some embodiments, the nucleic acids are mRNAs encoding the, the DNA binding proteins, and combinations of the nucleases and DNA binding proteins, and in further embodiments, the mRNAs may be protected. In some embodiments, the mRNA may be chemically modified, may comprise an ARCA cap, a mixture of unmodified and modified nucleotides, and combinations of an ARCA cap and a mixture of unmodified and modified nucleotides. Cells or cell lines descended from these cells are also provided, including partially or fully differentiated cells.

In some aspects, the HSC/PC are contacted with the nucleases, the DNA binding proteins, and combinations of the nucleases and DNA binding proteins of the invention ex vivo, following apheresis of the HSC/PC from a subject, or purification from harvested bone marrow. In some embodiments, the nucleases described herein cause modifications within the BCL11A enhancer regions, for example resulting a genetically modified cell that is structurally, functionally, and combinations of structurally and functionally distinct from wild-type cells, other modified (e.g., nuclease-modified) cells, and combinations of wild-type and other modified cells. In further embodiments, the HSC/PC containing the BCL11A enhancer region modifications are introduced back into the subject. In some instances, the HSC/PC containing the BCL11A enhancer region modifications are expanded prior to introduction. In other aspects, the genetically modified HSC/PCs are given to the subject in a bone marrow transplant wherein the HSC/PC engraft, differentiate and mature in vivo. In some embodiments, the HSC/PC are isolated from the subject following G-CSF-induced mobilization, plerixafor-induced mobilization, and combinations of G-CSF- and plerixafor-induced mobilization, and in others, the cells are isolated from human bone marrow or human umbilical cords. In some aspects, the subject is treated to a mild myeloablative procedure prior to introduction of the graft comprising the modified HSC/PC, while in other aspects, the subject is treated with a vigorous myeloablative conditioning regimen. In some embodiments, the methods and compositions of the invention are used to treat or prevent a hemoglobinopathy. In some aspects, the hemoglobinopathy is a thalassemia. In some aspects, the hemoglobinopathy is a beta thalassemia, while in other aspects, the hemoglobinopathy is sickle cell disease.

In some embodiments, the HSC/PC are further contacted with a donor molecule. In some embodiments, the donor molecule is delivered by a viral vector. The donor molecule may comprise one or more sequences encoding a functional polypeptide (e.g., a cDNA or fragment thereof), with or without a promoter. Additional sequences (coding or non-coding sequences) may be included when a donor molecule is used for inactivation, including but not limited to, sequences encoding a 2A peptide, SA site, IRES, etc.

In one aspect, the methods and compositions of the invention comprise methods for contacting the HSC/PC in vivo. The nucleases, DNA binding proteins, or combination of nucleases and DNA binding proteins are delivered to HSC/PC in situ by methods known in the art. In some embodiments, the nucleases and/or DNA binding proteins of the invention comprise a viral particle that is administered to the subject in need, while in others, the nucleases, DNA binding proteins, or combination of nucleases and DNA binding proteins comprise a nanoparticle (e.g. liposome). In some embodiments, the viral particles, nanoparticles, or combination of viral particles and nanoparticles are delivered to the organ (e.g. bone marrow) wherein the HSC/PC reside.

In another aspect, described herein are methods of integrating a donor nucleic acid into the genome of a cell via homology-independent mechanisms. The methods comprise creating a double-stranded break (DSB) in the genome of a cell and cleaving the donor molecule using a nuclease as described herein, such that the donor nucleic acid is integrated at the site of the DSB. In certain embodiments, the donor nucleic acid is integrated via non-homology dependent methods (e.g., NHEJ). As noted above, upon in vivo cleavage the donor sequences can be integrated in a targeted manner into the genome of a cell at the location of a DSB. The donor sequence can include one or more of the same target sites for one or more of the nucleases used to create the DSB. Thus, the donor sequence may be cleaved by one or more of the same nucleases used to cleave the endogenous gene into which integration is desired. In certain embodiments, the donor sequence includes different nuclease target sites from the nucleases used to induce the DSB. DSBs in the genome of the target cell may be created by any mechanism. In certain embodiments, the DSB is created by one or more zinc-finger nucleases (ZFNs), fusion proteins comprising a zinc finger binding domain that is engineered to bind a sequence within the region of interest, and a cleavage domain or a cleavage half-domain.

In one aspect, the donor may encode a regulatory protein of interest (e.g. ZFP TFs, TALE TFs or a CRISPR/Cas TF) that binds to, modulates expression of, or both binds to and modulates expression of a gene of interest. In one embodiment, the regulatory proteins bind to a DNA sequence and prevents binding of other regulatory factors. In another embodiment, the binding of the regulatory protein may modulate (i.e. induce or repress) expression of a target DNA.

In some embodiments, the transgenic HSC/PC cell, transgenic animal, or combination of transgenic HSC/PC cell and animal includes a transgene that encodes a human gene. In some instances, the transgenic animal comprises a knock out at the endogenous locus, and replacement of the endogenous gene with its human counterpart, thereby allowing the development of an in vivo system where the human protein may be studied in isolation. Such transgenic models may be used for screening purposes to identify small molecules or large biomolecules or other entities which may interact with or modify the human protein of interest. In some aspects, the transgene is integrated into the selected locus (e.g., safe-harbor) into a stem cell (e.g., an embryonic stem cell, an induced pluripotent stem cell, a hematopoietic stem cell, etc.) or animal embryo obtained by any of the methods described herein, and then the embryo is implanted such that a live animal is born. The animal is then raised to sexual maturity and allowed to produce offspring wherein at least some of the offspring comprise edited endogenous gene sequence or the integrated transgene.

In another aspect, provided herein is a method of altering gene expression (e.g., BCL11A, a globin gene, and combinations of BCL11A and a globin gene) in a cell, the method comprising: introducing, into the cell, one or more nucleases as described herein (shown in Table 1), under conditions such that the one or more proteins are expressed and expression of the gene is altered. In certain embodiments, expression of a globin gene (e.g., gamma globin or beta globin) is altered (e.g., increased). Any of the methods described herein may further comprise integrating a donor sequence (e.g., transgene or fragment thereof under the control of an exogenous or endogenous promoter) into the genome of the cell, for example integrating a donor at or near the site of nuclease cleavage in the BCL11A gene. The donor sequence is introduced to the cell using a viral vector, as an oligonucleotide, on a plasmid, and combinations of one or more methods selected from using a viral vector, as an oligonucleotide, or on a plasmid. The cell in which gene expression is altered may be, for example, a red blood cell (RBC) precursor cell, a hematopoietic stem cell (e.g., CD34+ cell), and combinations of RBC precursor cell and a hematopoietic stem cell.

In other embodiments, provided herein is a method of producing a genetically modified cell comprising a genomic modification within an endogenous BCL11A enhancer sequence (a modification to the nucleotide sequence of the BCL11A enhancer sequence), the method comprising the steps of: a) contacting a cell with a polynucleotide (e.g. DNA or mRNA) encoding a zinc finger nuclease comprising 4, 5, or 6 zinc finger domains in which each of the zinc finger domains comprises a recognition helix region in the order shown in a single row of Table 1; b) subjecting the cell to conditions conducive to expressing the zinc finger protein from the polynucleotide; and c) modifying the endogenous BCL11A enhancer sequence with the expressed zinc finger protein sufficient to produce the genetically modified cell. In certain embodiments, the cells are stimulated with at least one cytokine (e.g., prior to step (a)). The polynucleotide may be contacted with the cell using any suitable method, including but not limited to, via transfection, using a non-viral vector, using a viral vector, by chemical means or by exposure to an electric field (e.g., electroporation).

Cells comprising one or a combination of the genomic modifications described herein are also provided, including cells descended from the cells produced by the methods described herein.

Also provided is a method of treating a patient in need of an increase in globin gene expression, the method comprising administering to the patient the pharmaceutical preparation, wherein the pharmaceutical preparation comprises genetically modified cells, proteins, polynucleotides, and combinations of one or more selected from genetically modified cells, proteins, and polynucleotides, as described herein in an amount sufficient to increase the globin gene expression in the patient. In certain embodiments, the patient is known to have, is suspected of having, or is at risk of developing a thalassemia or sickle cell disease.

A kit, comprising the nucleic acids, proteins, genetically modified cells, and combinations of one or more selected from the nucleic acids, proteins, and genetically modified cells of the invention, is also provided. The kit may comprise nucleic acids encoding the nucleases, (e.g. RNA molecules or ZFN, TALEN or CRISPR/Cas system encoding genes contained in a suitable expression vector), aliquots of the nuclease proteins, donor molecules, suitable modifiers of stem cell self-renewal ("stemness"), cells, buffers, instructions (e.g., for performing the methods of the invention) and the like, including various combinations of these kit components. The invention includes, but is not limited to, a genetically modified cell (e.g., stem cell such as a hematopoietic (CD34+) stem cell or RBC precursor cell) comprising at least one genomic modification made by a nuclease (e.g., as shown in a single row of Table 1), wherein the genomic modification is within an endogenous BCL11A enhancer sequence, and further wherein the genomic modification is selected from the group consisting of insertions, deletions and combinations thereof and comprises a modification at, near or between any of SEQ ID NO:1 and SEQ ID NO:2. In certain embodiments, the cell is a genetically modified differentiated cell descended from a stem cell as described herein (e.g., a RBC descended from a hematopoietic stem cell or RBC precursor cell).

The nuclease may comprise at least one zinc finger nuclease (ZFN) (e.g., as shown in Table 1), at least one TALEN, and combinations of at least one ZFN and at least one TALEN. The nuclease(s) may be introduced into the cell in protein form, as a polynucleotide encoding the nuclease (s), or as a combination of protein form and polynucleotide encoding the nuclease(s). In certain embodiments, the genomic modification comprises an insertion that comprises integration of a donor polynucleotide encoding a transgene. Also provided are pharmaceutical compositions comprising one or more of the genetically modified cells as described herein.

Also provided is a DNA-binding protein comprising a zinc finger protein comprising 4, 5 or 6 zinc finger domains comprising a recognition helix region, wherein the zinc finger proteins comprise the recognition helix regions in the order shown in a single row of Table 1. Also provided is a TALE protein comprising a plurality of repeats that bind to a sequence comprising a portion (e.g., at least 4, 5, 6 or more) base pairs of the target sites shown in Table 1. A fusion protein comprising a zinc finger protein or TALE protein as described herein and a wild-type or engineered cleavage domain or cleavage half-domain is also provided as are polynucleotides encoding the proteins (ZFPs, TALEs, ZFNs, TALENs) as described herein. Cells (e.g., isolated stem cells such as hematopoietic (CD34+) stem cells) comprising one or more polynucleotides, proteins, and combinations of polynucleotides and proteins as described herein are also provided. Also provided are kits comprising one or more proteins, polynucleotides, cells, or combinations thereof as described herein.

A method of altering globin gene expression in a cell (e.g., RBC precursor cell, hematopoietic stem cell and combinations of RBC precursor cell and hematopoietic stem cell) is also described, the method comprising: introducing, into the cell, one or more polynucleotides encoding one or more nucleases as described herein, under conditions such that the one or more proteins are expressed and expression of the globin gene (e.g., gamma globin, beta globin, and combinations of gamma and beta globin) is altered (e.g., increased). In certain embodiments, the methods further comprise integrating a donor sequence into the genome of the cell, for example using a viral vector, as an oligonucleotide or on a plasmid. The donor sequence may comprise a transgene under the control of an endogenous or exogenous promoter.

Also provided is a method of producing a genetically modified cell comprising a genomic modification within an endogenous BCL11A enhancer sequence (e.g., target site as shown in Table 1), the method comprising the steps of: (a) contacting a cell with a polynucleotide encoding a fusion protein comprising a zinc finger nuclease comprising 4, 5, or 6 zinc finger domains in which each of the zinc finger domains comprises a recognition helix region in the order shown in a single row of Table 1; (b) subjecting the cell to conditions conducive to expressing the fusion protein from the polynucleotide; and (c) modifying the endogenous BCL11A enhancer sequence with the expressed fusion protein sufficient to produce the genetically modified cell. In certain embodiments, the method further comprises stimulating the cells with at least one cytokine. The polynucleotide(s) may be delivered inside the cell, for example using a non-viral delivery system, a viral delivery system, a delivery vehicle, and combinations selected from a non-viral delivery system, a viral delivery system, and a delivery vehicle and may comprise subjecting the cells to an electric field or employing cell membrane disruption as a delivery mechanism (so called 'Squeeze Technology', see e.g. Sharei et al. (2015) *PLOS ONE* doi: 10.1371/journal/pone.0118803).

Methods of treating a patient in need of an increase in globin gene expression (e.g., a patient is known to have, is suspected of having, or is at risk of developing a hemoglobinopathy such as a thalassemia (e.g., β-thalassemia) or sickle cell disease are also provided, the method comprising administering to the patient the pharmaceutical composition as described herein (e.g., proteins, polynucleotides, cells or a combination selected from proteins, polynucleotides and cells) in an amount sufficient to increase the globin gene expression in the patient.

These and other aspects will be readily apparent to the skilled artisan in light of disclosure as a whole.

BRIEF DESCRIPTION OF THE DRAWINGS

FIG. 1 shows the first step of the assay, in which cells are treated with ZFNs in the presence of supplemental oligonucleotide duplex DNA, which is captured into a fraction of the resulting cleavage events. FIG. 1B shows the subsequence step in which cells are cultured for seven days, genomic DNA is isolated, and segments of the genome flanking donor integration sites are amplified via adaptor-mediated PCR using a primer to the integrated oligonucleotide duplex. Amplicons are then sequenced to reveal candidate cleavage sites.

FIG. 2 depicts the location of 455 potential off-target loci identified by the oligonucleotide duplex integration site assay using the 51857/51949 original or parent ZFN pair. The top 63 loci are highlighted in gray and were analyzed in follow up indel analyses. Each locus is identified by the chromosome and base number indicating the most likely location of cleavage, as well as an indication of the number of integrants detected at that locus.

FIGS. 3A through 3C depict exemplary phosphate contacting residues within the zinc finger scaffold. FIG. 3A depicts a zinc finger interaction with a DNA molecule, and shows the location of the wild type arginine side chain and how it interacts with the phosphate backbone of the DNA molecule. FIG. 3B (SEQ ID Nos:7 to 17) depicts exemplary ZFN sequences showing where this arginine is located in the primary sequence of each zinc finger (vertical row of 'R' residues indicated via bold arrow) and also highlights those arginines that were substituted with glutamine in the ZFP backbone to eliminate the corresponding phosphate contact (individually boxed 'R' residues). The sequences also show the recognition helix regions (where residues −1 to +3, +5 and +6 are boxed and shaded) as well as a portion of the linker between the C-terminal zinc finger domain and the cleavage domain (cleavage domain not shown). FIG. 3C further depicts the spatial location of another potential backbone contacting lysine sidechain present in the FokI cleavage domain, which during specificity optimization may be substituted to a serine.

DETAILED DESCRIPTION

Figure 1A:
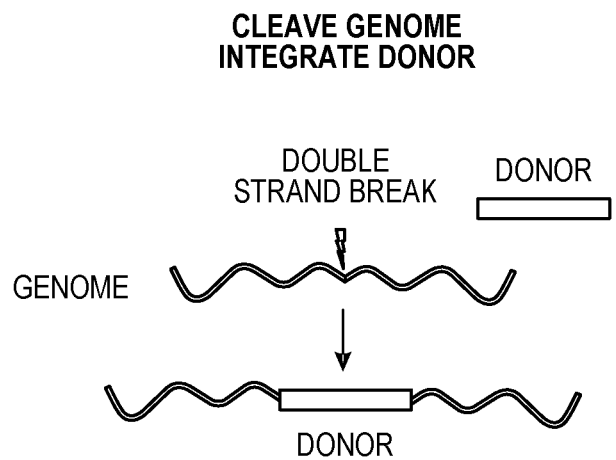
FIGS. 1A and 1B are schematics depicting an overview of the oligonucleotide duplex integration site assay.

Disclosed herein are compositions and methods for genome engineering for the modulation of BCL11A, gamma globin, and combinations of BLC11A and gamma globin expression and for the treatment, prevention, or treatment and prevention of hemoglobinopathies. In particular, via targeting with nucleases comprising the ZFPs having the recognition helix regions as shown in a single row of Table 1, disruption of an enhancer of BCL11A is efficiently achieved in HSC/PC and results in a change in relative gamma globin expression during subsequent erythropoiesis. This modulation of BCL11A and gamma globin expression is particularly useful for treatment of hemoglobinopathies (e.g., beta thalassemias, sickle cell disease) wherein there is insufficient beta globin expression or expression of a mutated form of beta-globin. Using the methods and compositions of the invention, the complications and disease related sequelae caused by the aberrant beta globin can be overcome by alteration of the expression of gamma globin in erythrocyte precursor cells.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar, phosphate moieties (e.g., phosphorothioate backbones), and combinations selected from base, sugar and phosphate moieties. In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind to another molecule. A binding protein can bind to, for example, a DNA molecule (a DNA-binding protein), an RNA molecule (an RNA-binding protein), a protein molecule (a protein-binding protein), or can bind to a combination of molecules selected from a DNA molecule, an RNA molecule or a protein. In the case of a protein-binding protein, it can bind to itself (to form homodimers, homotrimers, etc.), it can bind to one or more molecules of a different protein or proteins, or it can bind to both itself and one or molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein.

Zinc finger and TALE binding domains can be "engineered" to bind to a predetermined nucleotide sequence, for example via engineering (altering one or more amino acids) of the recognition helix region of a naturally occurring zinc finger or TALE protein. Therefore, engineered DNA binding proteins (zinc fingers or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP and/or TALE designs and binding data. See, for example, U.S. Pat. Nos. 6,140,081; 6,453,242; 6,534,261 and 8,585,526; see also PCT Publication Nos. WO 98/53058; WO 98/53059; WO 98/53060; WO 02/016536 and WO 03/016496.

A "selected" zinc finger protein or TALE is a protein not found in nature whose production results primarily from an empirical process such as phage display, interaction trap or hybrid selection. See e.g., U.S. Pat. Nos. 5,789,538; 5,925,523; 6,007,988; 6,013,453; 6,200,759; 8,586,526; PCT Publication Nos. WO 95/19431; WO 96/06166; WO 98/53057; WO 98/54311; WO 00/27878; WO 01/60970 WO 01/88197, WO 02/099084.

"TtAgo" is a prokaryotic Argonaute protein thought to be involved in gene silencing. TtAgo is derived from the bacteria *Thermus thermophilus*. See, e.g., Swarts et al. ibid, G. Sheng et al. (2013) *Proc. Natl. Acad. Sci. U.S.A.* 111, 652). A "TtAgo system" is all the components required including, for example, guide DNAs for cleavage by a TtAgo enzyme.

"Recombination" refers to a process of exchange of genetic information between two polynucleotides, including but not limited to, donor capture by non-homologous end joining (NHEJ) and homologous recombination. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, "synthesis-dependent strand annealing," in which the donor is used to resynthesize genetic information that will become part of the target, related processes, or combinations thereof. Such specialized HR often results in an alteration of the sequence of the target molecule such that part or all of the sequence of the donor polynucleotide is incorporated into the target polynucleotide.

In the methods of the disclosure, one or more targeted nucleases as described herein create a double-stranded break (DSB) in the target sequence (e.g., cellular chromatin) at a predetermined site. The DSB may result in indels by homology-directed repair or by non-homology-directed repair mechanisms. Deletions may include any number of base pairs. Similarly, insertions may include any number of base pairs including, for example, integration of a "donor" polynucleotide, optionally having homology to the nucleotide sequence in the region of the break. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

In any of the methods described herein, additional pairs of zinc-finger proteins or TALEN can be used for additional double-stranded cleavage of additional target sites within the cell.

Any of the methods described herein can be used for insertion of a donor of any size, or partial or complete inactivation of one or more target sequences in a cell by targeted integration of donor sequence that disrupts expression of the gene(s) of interest. Cell lines with partially or completely inactivated genes are also provided.

In any of the methods described herein, the exogenous nucleotide sequence (the "donor sequence" or "transgene") can contain sequences that are homologous, but not identical, to genomic sequences in the region of interest, thereby stimulating homologous recombination to insert a non-identical sequence in the region of interest. Thus, in certain embodiments, portions of the donor sequence that are homologous to sequences in the region of interest exhibit between about 80 to 99% (or any integer therebetween) sequence identity to the genomic sequence that is replaced. In other embodiments, the homology between the donor and genomic sequence is higher than 99%, for example if only 1 nucleotide differs as between donor and genomic sequences of over 100 contiguous base pairs. In certain cases, a non-homologous portion of the donor sequence can contain sequences not present in the region of interest, such that new sequences are introduced into the region of interest. In these instances, the non-homologous sequence is generally flanked by sequences of 50-1,000 base pairs (or any integral value therebetween) or any number of base pairs greater than 1,000, that are homologous or identical to sequences in the region of interest. In other embodiments, the donor sequence is non-homologous to the first sequence, and is inserted into the genome by non-homologous recombination mechanisms.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Pat. Nos. 7,888,121; 7,914,796; 8,034,598; 8,623,618 and U.S. Patent Publication No. 2011/0201055, incorporated herein by reference in their entireties.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 100,000,000 nucleotides in length (or any integer value therebetween or thereabove), preferably between about 100 and 100,000 nucleotides in length (or any integer therebetween), more preferably between about 2000 and 20,000 nucleotides in length (or any value therebetween) and even more preferable, between about 5 and 15 kb (or any value therebetween).

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

An "accessible region" is a site in cellular chromatin in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

A "target site" or "target sequence" is a nucleic acid sequence that defines a portion of a nucleic acid to which a binding molecule will bind, provided sufficient conditions for binding exist.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogenous molecule can also be the same type of molecule as an endogenous molecule but derived from a different species than the cell is derived from. For example, a human nucleic acid sequence may be introduced into a cell line originally derived from a mouse or hamster.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

As used herein, the term "product of an exogenous nucleic acid" includes both polynucleotide and polypeptide products, for example, transcription products (polynucleotides such as RNA) and translation products (polypeptides).

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP or TALE DNA-binding domain and one or more activation domains) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding sequences, transcribed sequences, and combinations of coding and transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, microRNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Genome editing (e.g., cleavage, alteration, inactivation, random mutation) can be used to modulate expression. Gene inactivation refers to any reduction in gene expression as compared to a cell that does not include a ZFP, TALE or CRISPR/Cas system as described herein. Thus, gene inactivation may be partial or complete.

A "protected" mRNA is one in which the mRNA has been altered in some manner to increase the stability or translation of the mRNA. Examples of protections include the use of replacement of up to 25% of the cytodine and uridine residues with 2-thiouridine (s2U) and 5-methylcytidine (m5C). The resulting mRNA exhibits less immunogenicity and more stability as compared with its unmodified counterpart. (see Karikó et al. ((2012), *Molecular Therapy*, Vol. 16, No. 11, pages 1833-1844). Other changes include the addition of a so-called ARCA cap, which increases the translationability of the in vitro produced mRNA (see U.S. Pat. No. 7,074,596).

A "region of interest" is any region of cellular chromatin, such as, for example, a gene or a non-coding sequence within or adjacent to a gene, in which it is desirable to bind an exogenous molecule. Binding can be for the purposes of targeted DNA cleavage, targeted recombination, and combinations of targeted DNA cleavage and targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

"Eukaryotic" cells include, but are not limited to, fungal cells (such as yeast), plant cells, animal cells, mammalian cells and human cells (e.g., T-cells).

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP, TALE or Cas DNA-binding domain is fused to an activation domain, the ZFP, TALE or Cas DNA-binding domain and the activation domain are in operative linkage if, in the fusion polypeptide, the ZFP, TALE of Cas DNA-binding domain portion is able to bind its target site, its binding site, and combinations of its target site and binding site, while the activation domain is able to upregulate gene expression. When a fusion polypeptide in which a ZFP, TALE or Cas DNA-binding domain is fused to a cleavage domain, the ZFP, TALE or Cas DNA-binding domain and the cleavage domain are in operative linkage if, in the fusion polypeptide, the ZFP, TALE or Cas DNA-binding domain portion is able to bind its target site, its binding site, and combinations of its target site and its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, can contain one or more amino acid or nucleotide substitutions, and can be combinations possessing more, fewer, or the same number of residues as the corresponding native molecule and containing one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

The terms "subject" and "patient" are used interchangeably and refer to mammals such as human patients and non-human primates, as well as experimental animals such as pigs, cows, rabbits, dogs, cats, rats, mice, and other animals. Accordingly, the term "subject" or "patient" as used herein means any mammalian patient or subject to which the or stem cells of the invention can be administered. Subjects of the present invention include those that have been exposed to one or more chemical toxins, including, for example, a nerve toxin.

"Stemness" refers to the relative ability of any cell to act in a stem cell-like manner, i.e., the degree of toti-, pluri-, multi- or oligo-potency and expanded or indefinite self-renewal that any particular stem cell may have.

Nucleases

Described herein are compositions, particularly nucleases, that are useful for in vivo cleavage of a donor molecule carrying a transgene and nucleases for cleavage of the genome of a cell such that the transgene is integrated into the genome in a targeted manner. In certain embodiments, one or more of the nucleases are naturally occurring. In other embodiments, one or more of the nucleases are non-naturally occurring, i.e., engineered in the DNA-binding domain, the cleavage domain, and a combination of the DNA-binding domain and cleavage domain. For example, the DNA-binding domain of a naturally-occurring nuclease may be altered to bind to a selected target site (e.g., a meganuclease that has been engineered to bind to site different than the cognate binding site). In other embodiments, the nuclease comprises heterologous DNA-binding and cleavage domains (e.g., zinc finger nucleases; TAL-effector domain DNA binding proteins; meganuclease DNA-binding domains with heterologous cleavage domains).

A. DNA-Binding Domains

In certain embodiments, the DNA binding domain of one or more of the nucleases used for in vivo cleavage, targeted cleavage of the genome of a cell, and combinations of in vivo cleavage and targeted cleavage of the genome of a cell comprises a zinc finger protein. A single zinc finger protein is made up of multiple zinc finger domains (e.g., 3, 4, 5, 6, or more zinc finger domains). Each zinc finger domain of is about 30 amino acids in length that it contains a beta turn (containing the two zinc coordinating residues and an alpha helix (containing the two invariant zinc coordinating residues), which are held in a particular conformation that allow binding to the protein to a target sequence. Canonical (C2H2) zinc finger domains having two cysteine (Cys) zinc coordinating residues in the beta turn and two histidine (His) zinc coordinating residues in the alpha helix or non-canonical (CH3) can be used. See, e.g., U.S. Pat. No. 9,234,187. A 7-amino acid recognition helix is contained between the zinc coordinating residues of the beta turn and the zinc coordinating residues of the alpha helix. The recognition helix region is numbered −1 to +6 within the zinc finger domain and the amino acids outside this recognition region (and excluding the zinc coordinating residues are referred to as backbone residues).

Preferably, the zinc finger protein is non-naturally occurring in that the recognition helix is engineered to bind to a target site of choice. See, for example, See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061, all incorporated herein by reference in their entireties.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Furthermore, in certain embodiments, the ZFP DNA-binding domains further comprise on or more modifications to the backbone of one or more the component zinc finger domains. The specificity of a ZFP for a target DNA sequence is dependent upon sequence specific contacts between the zinc finger domains and specific DNA bases, in particular, between the recognition helix region and the target site (typically each recognition helix binds to a target subsite of 3 nucleotides). In addition, the zinc finger domains also comprise amino acid residues that take part in non-specific interactions with the phosphates of the DNA backbone. Elrod-Erickson et al. ((1996) *Structure* 4:1171) demonstrated through co-crystallization of a zinc finger protein and its cognate DNA target that there are specific amino acids capable of interacting with the phosphates on the DNA backbone through formation of hydrogen bonds. Zinc finger proteins that employ the well-known Zif268 backbone typically have an arginine as the amino terminal residue of their second strand of β-sheet, which is also the second position carboxyl-terminal to the second invariant cysteine. This position can be referred to as (−5) within each zinc finger domain, as it is $5^{th}$ residue preceding the start of the α-helix (and position −5 relative to the recognition helix numbered −1 to +6). The arginine at this position can interact with a phosphate on the DNA backbone via formation of a charged hydrogen bond with its side-chain guanidinium group. Zinc finger proteins in the Zif268 backbone also frequently have a lysine at a position that is 4 residues amino-terminal to the first invariant cysteine. This position can be referred to as (−14) within each finger, as it is $14^{th}$ residue preceding the start of the α-helix for zinc fingers with two residues between the zinc coordinating cysteine residues (and position −14 relative to the recognition helix region numbered −1 to +6). The lysine can interact with a phosphate on the DNA backbone via formation of a water-mediated charged hydrogen bond with its side-chain amino group. Since phosphate groups are found all along the DNA backbone, this type of interaction between the zinc finger and a DNA molecule is generally considered to be non-sequence specific (J. Miller, Massachusetts Institute of Technology Ph.D. Thesis, 2002).

Recent studies have hypothesized that non-specific phosphate contacting side chains in some nucleases may also account for some amount of non-specificity of those nucleases (Kleinstiver et al. (2016) *Nature* 529(7587):490-5; Guilinger et al. (2014) *Nat Meth:* 429-435). Researchers have proposed that these nucleases may possess 'excess DNA-binding energy', meaning that the nucleases may have a greater affinity for their DNA target than is required to substantially bind and cleave the target site. Thus, attempts were made to decrease the cationic charges in the TALE DNA binding domain (Guilinger, ibid) or the Cas9 DNA binding domain (Kleinstiver, ibid) to lower the DNA-binding energy of these nucleases, which resulted in increased cleavage specificity in vitro. However, additional studies (Sternberg et al. (2015) *Nature* 527(7576):110-113) also suggest a role in proper folding and activation of the Cas9 nuclease domain for some of the cationic amino acids that were mutated in the Kleinstiver study of the Cas9 DNA binding domain. Thus, the exact role of these amino acids in Cas9 activity is not known.

The methods and compositions of the invention thus include mutations to amino acids within the ZFP DNA binding domain ('ZFP backbone') that can interact non-specifically with phosphates on the DNA backbone, but they do not comprise changes in the DNA recognition helices. Thus, the invention includes mutations of cationic amino acid residues in the ZFP backbone that are not required for nucleotide target specificity. In some embodiments, these mutations in the ZFP backbone comprise mutating a cationic amino acid residue to a neutral or anionic amino acid residue. In some embodiments, these mutations in the ZFP backbone comprise mutating a polar amino acid residue to a neutral or non-polar amino acid residue. In preferred embodiments, mutations at made at position (−5), position (−9), position (−14), and combinations of mutations selected from mutations made at position (−5), position (−9) and position (−14) relative to the DNA binding helix. In some embodiments, a zinc finger may comprise one or more mutations at (−5), (−9), (−14), and combinations of mutations selected from mutations at (−5), (−9), and (−14). In further embodiments, one or more zinc finger(s) in a multi-finger zinc finger protein may comprise mutations in (−5), (−9), (−14) and combinations selected from (−5), (−9), and (−14). In some embodiments, the amino acids at (−5), (−9), (−14) and combinations selected from (−5), (−9), and (−14) (e.g. an arginine (R) or lysine (K)) are mutated to an alanine (A), leucine (L), Ser (S), Asp (D), Glu (E), Tyr (Y) and/or glutamine (Q).

In any of these fusion polypeptides described herein, the ZFP partners may further comprise mutations in the zinc finger DNA binding domain in the (−5), (−9), (−14) positions, and combinations of mutations selected from mutations at (−5), (−9), and (−14). In some embodiments, the Arg (R) at position −5 is changed to a Tyr (Y), Asp (D), Glu (E), Leu (L), Gin (Q), or Ala (A). In other embodiments, the Arg (R) at position (−9) is replaced with Ser (S), Asp (D), or Glu (E). In further embodiments, the Arg (R) at position (−14) is replaced with Ser (S) or Gin (Q). In other embodiments, the fusion polypeptides can comprise mutations in the zinc finger DNA binding domain where the amino acids at the (−5), (−9), (−14) positions, and combinations of mutations selected from mutations at (−5), (−9), and (−14) are changed to any of the above listed amino acids in any combination.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

Selection of target sites; ZFPs and methods for design and construction of fusion proteins (and polynucleotides encoding same) are known to those of skill in the art and described in detail in U.S. Pat. Nos. 6,140,081; 5,789,538; 6,453,242; 6,534,261; 5,925,523; 6,007,988; 6,013,453; 6,200,759; PCT Publication Nos. WO 95/19431; WO 96/06166; WO 98/53057; WO 98/54311; WO 00/27878; WO 01/60970; WO 01/88197; WO 02/099084; WO 98/53058; WO 98/53059; WO 98/53060; WO 02/016536 and WO 03/016496.

Nearly any linker (spacer) may be used between one or more of the components of the DNA-binding domain (e.g., zinc fingers), between one or more DNA-binding domains, between the DNA-binding domain and the functional domain (e.g., nuclease), and between one or more DNA-binding domains and between the DNA-binding domain and the functional domain. Non-limiting examples of suitable linker sequences include U.S. Pat. Nos. 8,772,453; 7,888,121; 6,479,626; 6,903,185; and 7,153,949; and U.S. Patent Publication Nos. 2009/0305419; 2015/0064789 and 2015/0132269. Thus, the proteins described herein may include any combination of suitable linkers between the individual DNA-binding components, between the DNA-binding domain and the functional domain, or between one or more DNA-binding domains and between the DNA-binding domain and the functional domain of the compositions described herein.

B. Cleavage Domains

Any suitable cleavage domain can be operatively linked to the DNA-binding domains as described herein to form a nuclease. The cleavage domain may be heterologous to the DNA-binding domain, for example a zinc finger DNA-binding domain and a cleavage domain from a nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) *Nucleases*, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof; as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However, any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

For optimal cleavage specificity by a sequence-selective (artificial) nuclease, it is desirable to arrange conditions so that on-target binding and activity is not saturating. Under saturating conditions—by definition—an excess of nuclease is used over what is necessary to achieve complete on-target activity. This excess provides no on-target benefit but can nonetheless result in increased cleavage at off-target sites. For monomeric nucleases, saturating conditions may be readily avoided by performing a simple dose response study to identify and avoid the saturating plateau on a titration curve. However, for a dimeric nuclease such as ZFN, TALEN or dCas-Fok, identifying and avoiding saturating conditions may be more complicated if the binding affinities of the individual monomers are dissimilar. In such cases, a dose response study using a simple 1:1 nuclease ratio will only reveal the saturation point of the weaker binding monomer. Under such a scenario, if, for example, monomer affinities differ by a factor of 10, then at the saturation point identified in a 1:1 titration study the higher affinity monomer will be present at a concentration that is 10-fold higher than it needs to be. The resulting excess of the higher affinity monomer can in turn lead to increased off-target activity without providing any beneficial increase in cleavage at the intended target, potentially leading to a decreased specificity overall for any given nuclease pair.

An exemplary Type IIS restriction enzyme, whose cleavage domain is separable from the binding domain, is FokI. This particular enzyme is active as a dimer. Bitinaite et al.

(1998) *Proc. Natl. Acad. Sci. USA* 95:10,570-10,575. Accordingly, for the purposes of the present disclosure, the portion of the Fok I enzyme used in the disclosed fusion proteins is considered a cleavage half-domain. Thus, for targeted double-stranded cleavage, targeted replacement of cellular sequences using zinc finger-Fok I fusions, and combinations of targeted double-stranded cleavage and targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a zinc finger binding domain and two Fok I cleavage half-domains can also be used. Parameters for targeted cleavage and targeted sequence alteration using zinc finger-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in U.S. Pat. No. 7,888,121 incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in See, e.g., U.S. Pat. Nos. 7,914,796; 8,034,598 and 8,623,618, the disclosures of all of which are incorporated by reference in their entireties herein. Amino acid residues at positions 446, 447, 479, 483, 484, 486, 487, 490, 491, 496, 498, 499, 500, 531, 534, 537, and 538 of FokI are all targets for influencing dimerization of the FokI cleavage half-domains where the numbering is with respect to the crystal structures 1FOK.pdb and 2FOK.pdb (see Wah et al. (1997) *Nature* 388:97-100) having the sequence shown below:

```
Wild type FokI cleavage half domain
                                       (SEQ ID NO: 18)
QLVKSELEEKKSELRHKLKYVPHEYIELIEIARNSTQDRILEMKVMEFFM

KVYGYRGKHLGGSRKPDGAIYTVGSPIDYGVIVDTKAYSGGYNLPIGQAD

EMQRYVEENQTRNKHINPNEWWKVYPSSVTEFKFLFVSGHFKGNYKAQLT

RLNHITNCNGAVLSVEELLIGGEMIKAGTLTLEEVRRKFNNGEINF
```

Exemplary engineered cleavage half-domains of FokI that form obligate heterodimers include a pair in which a first cleavage half-domain includes mutations at amino acid residues at positions 490 and 538 of FokI and a second cleavage half-domain includes mutations at amino acid residues 486 and 499.

Thus, in one embodiment, a mutation at 490 replaces Glu (E) with Lys (K); the mutation at 538 replaces Ile (I) with Lys (K); the mutation at 486 replaced Gin (Q) with Glu (E); and the mutation at position 499 replaces Ile (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E: I499L". The engineered cleavage half-domains described herein are obligate heterodimer mutants in which aberrant cleavage via the ZFN homodimers is minimized or abolished. See, e.g., U.S. Patent Publication No. 2008/0131962, the disclosure of which is incorporated by reference in its entirety for all purposes. In certain embodiments, the engineered cleavage half-domain comprises mutations at positions 486, 499 and 496 (numbered relative to wild-type FokI), for instance mutations that replace the wild type Gin (Q) residue at position 486 with a Glu (E) residue, the wild type Ile (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Ile (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). See, e.g., U.S. Pat. Nos. 7,914,796; 8,034,598 and 8,623,618. In other embodiments, the engineered cleavage half domain comprises the "Sharkey", "Sharkey" mutations, and combinations of the "Sharkey" and "Sharkey" mutations (see Guo et al. (2010) *J. Mol. Biol.* 400(1):96-107).

Thus, cleavage half domains derived from Fold may comprise a mutation in one or more of amino acid residues as shown in SEQ ID NO:18, including mutations in the dimerization domain as described above; mutations in the catalytic domain, mutations in other amino acid residues such as phosphate contact residues, and any combination of mutations selected from mutations in the dimerization domain, mutations in the catalytic domain, and mutations in other amino acid residues such as phosphate contact residues. Mutations include substitutions (of a wild-type amino acid residue with a different residue), insertions (of one or more amino acid residues), deletions (of one or more amino acid residues), and any combination of mutations selected from substitutions, insertions and deletions. In certain embodiments, one or more of residues 414-426, 443-450, 467-488, 501-502, 521-531 (numbered relative to SEQ ID NO:18), and any combination of such residues, are mutated since these residues are located close to the DNA backbone in a molecular model of a ZFN bound to its target site described in Miller et al. ((2007) *Nat Biotechnol* 25:778-784). In certain embodiments, one or more residues at positions 416, 422, 447, 448, and 525 are mutated. In certain embodiments, the mutation comprises a substitution of a wild-type residue with a different residue, for example a serine (S) residue. In certain embodiments, the FokI cleavage domain of the nucleases described herein comprise an ELD dimerization domain mutation, a KKR dimerization domain mutation, a K525S mutation, and any combination selected from an ELD dimerization domain mutation or a KKR dimerization domain mutation and a K525S mutation.

Engineered cleavage domains described herein can be prepared using any suitable method, for example, by site-directed mutagenesis of wild-type cleavage half-domains (Fok I) as described in U.S. Pat. Nos. 7,888,121; 7,914,796;

8,034,598 and 8,623,618. Furthermore, the cleavage domains described herein may be fused to a DNA-binding domain (e.g., ZFP) using any suitable linker, including, but not limited to the linkers described in U.S. Pat. Nos. 9,394,531 and 9,567,609.

Alternatively, nucleases may be assembled in vivo at the nucleic acid target site using so-called "split-enzyme" technology (see, e.g. U.S. Patent Publication No. 2009/0068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases can be screened for activity prior to use, for example in a yeast-based chromosomal system as described in WO 2009/042163 and 20090068164. Expression of the nuclease may be under the control of a constitutive promoter or an inducible promoter, for example the galactokinase promoter which is activated (de-repressed) in the presence of raffinose, galactose and a combination of raffinose and galactose and repressed in presence of glucose.

The nuclease(s) as described herein may make one or more double-stranded, one or more single-stranded cuts, and combinations of one or more double-stranded and one or more single-stranded cuts in the target site. In certain embodiments, the nuclease comprises a catalytically inactive cleavage domain (e.g., FokI, a Cas protein and combinations of FokI and a Cas protein). See, e.g., U.S. Pat. Nos. 9,200,266; 8,703,489 and Guillinger et al. (2014) *Nature Biotech.* 32(6):577-582. The catalytically inactive cleavage domain may, in combination with a catalytically active domain act as a nickase to make a single-stranded cut. Therefore, two nickases can be used in combination to make a double-stranded cut in a specific region. Additional nickases are also known in the art, for example, McCaffery et al. (2016) *Nucleic Acids Res.* 44(2):e11. doi: 10.1093/nar/gkv878. Epub 2015 Oct. 19.

Target Sites

As described in detail above, DNA domains can be engineered to bind to any sequence of choice. An engineered DNA-binding domain can have a novel binding specificity, compared to a naturally-occurring DNA-binding domain. In certain embodiments, the DNA-binding domains bind to a sequence within a BCL11A enhancer sequence, for example a target site (typically 9, 10, 11, 12, 13, 14, 15, 16, 17, 18, 19, 20, 21 or even more base pairs) is between exon 2 and exon 3 of BCL11A, including DNA-binding domains that bind to a sequence within a DNAseI hypersensitive site in the BCL11A enhancer sequence (e.g., +58) as shown in Table 1. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties. Rational design of TAL-effector domains can also be performed. See, e.g., U.S. Patent Publication No. 2011/0301073.

Exemplary selection methods applicable to DNA-binding domains, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as PCT Publication Nos. WO 98/37186; WO 98/53057; WO 00/27878; WO 01/88197 and U.K. Patent No. GB 2,338,237. In addition, enhancement of binding specificity for zinc finger binding domains has been described, for example, in co-owned WO 02/077227.

Selection of target sites; nucleases and methods for design and construction of fusion proteins (and polynucleotides encoding same) are known to those of skill in the art and described in detail in U.S. Patent Publication Nos. 2005/0064474 and 2006/0188987, incorporated by reference in their entireties herein.

In addition, as disclosed in these and other references, DNA-binding domains (e.g., multi-fingered zinc finger proteins) and fusions of DNA-binding domain(s) and functional domain(s) may be linked together using any suitable linker sequences, including for example, linkers of 5 or more amino acids. U.S. Pat. Nos. 8,772,453; 7,888,121 (e.g., "ZC" linker); U.S. Pat. Nos. 6,479,626; 6,903,185; and 7,153,949; U.S. Publication No. 2009/0305419) and 2015/0064789. The proteins described herein may include any combination of suitable linkers between the individual DNA-binding domains of the protein. See, also, U.S. Pat. No. 8,586,526.

Donors

In certain embodiments, the present disclosure relates to nuclease-mediated targeted integration of an exogenous sequence into the genome of a cell using the BCL11A enhancer region-binding molecules described herein. As noted above, insertion of an exogenous sequence (also called a "donor sequence" or "donor" or "transgene"), for example for deletion of a specified region, for correction of a mutant gene, for a combination of deletion of a specified region and correction of a mutant gene, or for increased expression of a wild-type gene. It will be readily apparent that the donor sequence is typically not identical to the genomic sequence where it is placed. A donor sequence can contain a non-homologous sequence flanked by two regions of homology to allow for efficient HDR at the location of interest or can be integrated via non-homology directed repair mechanisms such as NHEJ. Additionally, donor sequences can comprise a vector molecule containing sequences that are not homologous to the region of interest in cellular chromatin. A donor molecule can contain several, discontinuous regions of homology to cellular chromatin, and, for example, lead to a deletion of a BCL11A enhancer region (or a fragment thereof) when used as a substrate for repair of a DSB induced by one of the nucleases described here. Further, for targeted insertion of sequences not normally present in a region of interest, said sequences can be present in a donor nucleic acid molecule and flanked by regions of homology to sequence in the region of interest.

Polynucleotides for insertion can also be referred to as "exogenous" polynucleotides, "donor" polynucleotides or molecules or "transgenes." The donor polynucleotide can be DNA or RNA, single-stranded or double-stranded, and can be introduced into a cell in linear or circular form. See, e.g., U.S. Patent Application Publication Nos. 2010/0047805 and 2011/0207221. The donor sequence(s) are preferably contained within a DNA MC, which may be introduced into the cell in circular or linear form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and self-complementary oligonucleotides are optionally ligated to one or both ends. See, for example, Chang et al. (1987) *Proc. Natl. Acad. Sci. USA* 84:4959-4963; Nehls et al.

(1996) *Science* 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues. If introduced in double-stranded form, the donor may include one or more nuclease target sites, for example, nuclease target sites flanking the transgene to be integrated into the cell's genome. See, e.g., U.S. Patent Publication No. 2013/0326645.

A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (IDLV)).

In certain embodiments, the double-stranded donor includes sequences (e.g., coding sequences, also referred to as transgenes) greater than 1 kb in length, for example between 2 and 200 kb, between 2 and 10 kb (or any value therebetween). The double-stranded donor also includes at least one nuclease target site, for example. In certain embodiments, the donor includes at least 2 target sites, for example for a pair of ZFNs or TALENs. Typically, the nuclease target sites are outside the transgene sequences, for example, 5' and/or 3' to the transgene sequences, for cleavage of the transgene. The nuclease cleavage site(s) may be for any nuclease(s). In certain embodiments, the nuclease target site(s) contained in the double-stranded donor are for the same nuclease(s) used to cleave the endogenous target into which the cleaved donor is integrated via homology-independent methods.

The donor is generally inserted so that its expression is driven by the endogenous promoter at the integration site, namely the promoter that drives expression of the endogenous gene into which the donor is inserted (e.g., globin, AAVS1, etc.). However, it will be apparent that the donor may comprise a promoter, an enhancer, and combinations of both a promoter and enhancer, for example a constitutive promoter or an inducible or tissue specific promoter.

The donor molecule may be inserted into an endogenous gene such that all, some or none of the endogenous gene is expressed. In other embodiments, the transgene (e.g., with or without globin encoding sequences) is integrated into any endogenous locus, for example a safe-harbor locus. See, e.g., U.S. Patent Publication Nos. 2008/0299580; 2008/0159996 and 2010/0218264.

Furthermore, although not required for expression, exogenous sequences may also include transcriptional or translational regulatory sequences, for example, promoters, enhancers, insulators, internal ribosome entry sites, sequences encoding 2A peptides, polyadenylation signals, and combinations thereof.

The transgenes carried on the donor sequences described herein may be isolated from plasmids, cells or other sources using standard techniques known in the art such as PCR. Donors for use can include varying types of topology, including circular supercoiled, circular relaxed, linear and the like. Alternatively, they may be chemically synthesized using standard oligonucleotide synthesis techniques. In addition, donors may be methylated or lack methylation. Donors may be in the form of bacterial or yeast artificial chromosomes (BACs or YACs).

The double-stranded donor polynucleotides described herein may include one or more non-natural bases, one or more backbones, and combinations of one or more non-natural bases and one or more backbones. In particular, insertion of a donor molecule with methylated cytosines may be carried out using the methods described herein to achieve a state of transcriptional quiescence in a region of interest.

The exogenous (donor) polynucleotide may comprise any sequence of interest (exogenous sequence). Exemplary exogenous sequences include, but are not limited to any polypeptide coding sequence (e.g., cDNAs), promoter sequences, enhancer sequences, epitope tags, marker genes, cleavage enzyme recognition sites and various types of expression constructs. Marker genes include, but are not limited to, sequences encoding proteins that mediate antibiotic resistance (e.g., ampicillin resistance, kanamycin resistance, neomycin resistance, G418 resistance, puromycin resistance, hygromycin resistance, blasticidin resistance), sequences encoding colored or fluorescent or luminescent proteins (e.g., green fluorescent protein, enhanced green fluorescent protein, red fluorescent protein, luciferase), and proteins which mediate enhanced cell growth, gene amplification (e.g., dihydrofolate reductase) and combinations of enhanced cell growth and gene amplification. Epitope tags include, for example, one or more copies of FLAG, His, Myc, tandem affinity purification (TAP), HA, biotinylatable peptide, or any detectable amino acid sequence.

In a preferred embodiment, the exogenous sequence (transgene) comprises a polynucleotide encoding any polypeptide of which expression in the cell is desired, including, but not limited to antibodies, antigens, enzymes, receptors (cell surface or nuclear), hormones, lymphokines, cytokines, reporter polypeptides, growth factors, and functional fragments of any of the above. The coding sequences may be, for example, cDNAs.

For example, the exogenous sequence may comprise a sequence encoding a polypeptide that is lacking or non-functional in the subject having a genetic disease, including but not limited to any of the following genetic diseases: achondroplasia, achromatopsia, acid maltase deficiency, adenosine deaminase deficiency (OMIM No. 102700), adrenoleukodystrophy, aicardi syndrome, alpha-1 antitrypsin deficiency, alpha-thalassemia, androgen insensitivity syndrome, apert syndrome, arrhythmogenic right ventricular, dysplasia, ataxia telangictasia, barth syndrome, beta-thalassemia, blue rubber bleb nevus syndrome, canavan disease, chronic granulomatous diseases (CGD), cri du chat syndrome, cystic fibrosis, dercum's disease, ectodermal dysplasia, fanconi anemia, fibrodysplasiaossificans progressive, fragile X syndrome, galactosemis, Gaucher's disease, generalized gangliosidoses (e.g., GM1), hemochromatosis, the hemoglobin C mutation in the $6^{th}$ codon of beta-globin (HbC), hemophilia, Huntington's disease, Hurler Syndrome, hypophosphatasia, Klinefleter syndrome, Krabbes Disease, Langer-Giedion Syndrome, leukocyte adhesion deficiency (LAD, OMIM No. 116920), leukodystrophy, long QT syndrome, Marfan syndrome, Moebius syndrome, mucopolysaccharidosis (MPS), nail patella syndrome, nephrogenic diabetes insipdius, neurofibromatosis, Neimann-Pick disease, osteogenesis imperfecta, porphyria, Prader-Willi syndrome, progeria, Proteus syndrome, retinoblastoma, Rett syndrome, Rubinstein-Taybi syndrome, Sanfilippo syndrome, severe combined immunodeficiency (SCID), Shwachman syndrome, sickle cell disease (sickle cell anemia), Smith-Magenis syndrome, Stickler syndrome, Tay-Sachs disease, Thrombocytopenia Absent Radius (TAR) syndrome, Treacher Collins syndrome, trisomy, tuberous sclerosis, Turner's syndrome, urea cycle disorder, von Hippel-Landau disease, Waardenburg syndrome, Williams syndrome, Wilson's disease, Wiskott-Aldrich syndrome, X-linked lymphoproliferative syndrome (XLP, OMIM No. 308240).

Additional exemplary diseases that can be treated by targeted integration include acquired immunodeficiencies, lysosomal storage diseases (e.g., Gaucher's disease, GM1, Fabry disease and Tay-Sachs disease), mucopolysaccahidosis (e.g. Hunter's disease, Hurler's disease), hemoglobinopathies (e.g., sickle cell disease, HbC, α-thalassemia, β-thalassemia) and hemnophilias.

In certain embodiments, the exogenous sequences can comprise a marker gene (described above), allowing selection of cells that have undergone targeted integration, and a linked sequence encoding an additional functionality. Non-limiting examples of marker genes include GFP, drug selection marker(s) and the like.

Additional gene sequences that can be inserted may include, for example, wild-type genes to replace mutated sequences. For example, a wild-type Factor IX gene sequence may be inserted into the genome of a stem cell in which the endogenous copy of the gene is mutated. The wild-type copy may be inserted at the endogenous locus, or may alternatively be targeted to a safe harbor locus.

Construction of such expression cassettes, following the teachings of the present specification, utilizes methodologies well known in the art of molecular biology (see, for example, Ausubel or Maniatis). Before use of the expression cassette to generate a transgenic animal, the responsiveness of the expression cassette to the stress-inducer associated with selected control elements can be tested by introducing the expression cassette into a suitable cell line (e.g., primary cells, transformed cells, or immortalized cell lines).

Furthermore, although not required for expression, exogenous sequences may also transcriptional or translational regulatory sequences, for example, promoters, enhancers, insulators, internal ribosome entry sites, sequences encoding 2A peptides, polyadenylation signals, and combinations of 2A polypeptides and polyadenylation signals. Further, the control elements of the genes of interest can be operably linked to reporter genes to create chimeric genes (e.g., reporter expression cassettes).

Targeted insertion of non-coding nucleic acid sequence may also be achieved. Sequences encoding antisense RNAs, RNAi, shRNAs and micro RNAs (miRNAs) may also be used for targeted insertions.

In additional embodiments, the donor nucleic acid may comprise non-coding sequences that are specific target sites for additional nuclease designs. Subsequently, additional nucleases may be expressed in cells such that the original donor molecule is cleaved and modified by insertion of another donor molecule of interest. In this way, reiterative integrations of donor molecules may be generated allowing for trait stacking at a particular locus of interest or at a safe harbor locus.

Delivery

The nucleases as described herein (Table 1), polynucleotides encoding these nucleases, donor polynucleotides and compositions comprising the proteins, polynucleotides, and combinations of proteins and polynucleotides described herein may be delivered in vivo or ex vivo by any suitable means into any cell type.

Suitable cells include eukaryotic (e.g., animal) and prokaryotic cells and eukaryotic and prokaryotic cell lines. Non-limiting examples of such cells or cell lines generated from such cells include COS, CHO (e.g., CHO-S, CHO-KI, CHO-DG44, CHO-DUXB11, CHO-DUKX, CHOKISV), VERO, MDCK, WI38, V79, B14AF28-G3, BHK, HaK, NS0, SP2/0-Ag14, HeLa, HEK293 (e.g., HEK293-F, HEK293-H, HEK293-T), and perC6 cells as well as insect cells such as Spodopterafugiperda (Sf), or fungal cells such as *Saccharomyces, Pichia* and *Schizosaccharomyces*. In certain embodiments, the cell line is a CHO, MDCK or HEK293 cell line. Suitable cells also include stem cells such as, by way of example, embryonic stem cells, induced pluripotent stem cells, hematopoietic stem cells, neuronal stem cells and mesenchymal stem cells.

Methods of delivering nucleases as described herein are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

Nucleases, donor constructs, and combinations of nucleases and donor constructs as described herein may also be delivered using vectors containing sequences encoding one or more of the ZFN(s), described herein. Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824, incorporated by reference herein in their entireties. Furthermore, it will be apparent that any of these vectors may comprise one or more of the sequences needed for treatment. Thus, when one or more nucleases and a donor construct are introduced into the cell, the nucleases, donor polynucleotide, and combinations of nucleases and donor polynucleotide may be carried on the same vector or on different vectors (DNA MC(s)). When multiple vectors are used, each vector may comprise a sequence encoding one or multiple nucleases, one or more donor constructs, and combinations of one or more nucleases and one or more donor constructions. Conventional viral and non-viral based gene transfer methods can be used to introduce nucleic acids encoding nucleases, donor constructs, and combinations of nucleases and donor constructs in cells (e.g., mammalian cells) and target tissues. Non-viral vector delivery systems include DNA or RNA plasmids, DNA MCs, naked nucleic acid, and nucleic acid complexed with a delivery vehicle such as a liposome or poloxamer. Suitable non-viral vectors include nanotaxis vectors, including vectors commercially available from InCellArt (France). Viral vector delivery systems include DNA and RNA viruses, which have either episomal or integrated genomes after delivery to the cell. For a review of in vivo delivery of engineered DNA-binding proteins and fusion proteins comprising these binding proteins, see, e.g., Rebar (2004) *Expert Opinion Invest. Drugs* 13(7):829-839; Rossi et al. (2007) *Nature Biotech.* 25(12): 1444-1454 as well as general gene delivery references such as Anderson, *Science* 256:808-813 (1992); Nabel & Felgner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Böhm (eds.) (1995); and Yu et al., *Gene Therapy* 1:13-26 (1994).

Methods of non-viral delivery of nucleic acids include electroporation, lipofection, microinjection, biolistics, virosomes, liposomes, immunoliposomes, polycation or lipid:nucleic acid conjugates, naked DNA, artificial virions, membrane deformation, and agent-enhanced uptake of DNA. Sonoporation using, e.g., the Sonitron 2000 system (RichMar) can also be used for delivery of nucleic acids.

Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc., (see for example U.S. Pat. No. 6,008,336). Lipofection is described in e.g., U.S. Pat. Nos. 5,049,386; 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024.

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787). Other lipid:nucleic acid complexes include those comprising novel cationic lipids, novel pegylated lipids, and combinations of novel cationic lipids and novel pegylated lipids (see e.g. U.S. Provisional Patent Application Nos. 62/432,042 and 62/458,373).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et al (2009) *Nature Biotechnology* 27(7):643).

The use of RNA or DNA viral based systems for the delivery of nucleic acids encoding engineered ZFPs, TALEs and CRISPR/Cas systems take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of ZFPs include, but are not limited to, retroviral, lentiviral, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *PNAS* 81:6466-6470 (1984); and Samulski et al., *J. Virol.* 63:03822-3828 (1989).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al., *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother.* 44(1):10-20 (1997); Dranoff et al., *Hum. Gene Ther.* 1:111-2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)). Other AAV serotypes, including AAV1, AAV2, AAV3, AAV4, AAV5, AAV6, AAV7, AAV8, AAV9 and AAVrh.10 and any novel AAV serotype can also be used in accordance with the present invention.

Replication-deficient recombinant adenoviral vectors (Ad) can be produced at high titer and readily infect a number of different cell types. Most adenovirus vectors are engineered such that a transgene replaces the Ad E1a, E1b, or E3 genes; subsequently the replication defective vector is propagated in human 293 cells that supply deleted gene function in trans. Ad vectors can transduce multiple types of tissues in vivo, including nondividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al, *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include HEK293 and Sf9 cells, which can be used to package AAV and adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV. In some embodiments, AAV is produced using a baculovirus expression system (see e.g. U.S. Pat. Nos. 6,723,551 and 7,271,002).

Purification of AAV particles from a 293 or baculovirus system typically involves growth of the cells which produce the virus, followed by collection of the viral particles from the cell supernatant or lysing the cells and collecting the virus from the crude lysate. AAV is then purified by methods known in the art including ion exchange chromatography (e.g. see U.S. Pat. Nos. 7,419,817 and 6,989,264), ion exchange chromatography and CsCl density centrifugation (e.g. PCT publication WO2011094198A1), immunoaffinity chromatography (e.g. WO2016128408) or purification using AVB Sepharose (e.g. GE Healthcare Life Sciences).

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl. Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Vectors (e.g., retroviruses, adenoviruses, liposomes, etc.) containing nucleases, donor constructs, and combinations of nucleases and donor constructs can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Vectors suitable for introduction of polynucleotides (e.g. nuclease-encoding, double-stranded donors, and combinations of nuclease-encoding and double-stranded donors) described herein include non-integrating lentivirus vectors (IDLV). See, for example, Ory et al. (1996) *Proc. Natl. Acad. Sci. USA* 93:11382-11388; Dull et al. (1998) *J. Virol.* 72:8463-8471; Zuffery et al. (1998) *J. Virol.* 72:9873-9880; Follenzi et al. (2000) *Nature Genetics* 25:217-222; U.S. Patent Publication No. 2009/0117617.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences*, 17$^{th}$ ed., 1989).

It will be apparent that the nuclease-encoding sequences and donor constructs can be delivered using the same or different systems. For example, the nucleases and donors can be carried by the same DNA MC. Alternatively, a donor polynucleotide can be carried by a MC, while the one or more nucleases can be carried by a standard plasmid or AAV vector. Furthermore, the different vectors can be administered by the same or different routes (intramuscular injection, tail vein injection, other intravenous injection, intraperitoneal administration or intramuscular injection). The vectors can be delivered simultaneously or in any sequential order.

Thus, the instant disclosure includes in vivo or ex vivo treatment of diseases and conditions that are amenable to insertion of a transgenes encoding a therapeutic protein. The compositions are administered to a human patient in an amount effective to obtain the desired concentration of the therapeutic polypeptide in the serum or the target organ or cells. Administration can be by any means in which the polynucleotides are delivered to the desired target cells. For example, both in vivo and ex vivo methods are contemplated. Intravenous injection to the portal vein is a preferred method of administration. Other in vivo administration modes include, for example, direct injection into the lobes of the liver or the biliary duct and intravenous injection distal to the liver, including through the hepatic artery, direct injection in to the liver parenchyma, injection via the hepatic artery, and retrograde injection through the biliary tree. Ex vivo modes of administration include transduction in vitro of resected hepatocytes or other cells of the liver, followed by infusion of the transduced, resected hepatocytes back into the portal vasculature, liver parenchyma or biliary tree of the human patient, see e.g., Grossman et al., (1994) *Nature Genetics*, 6:335-341.

The effective amount of nuclease(s) and donor to be administered will vary from patient to patient and according to the therapeutic polypeptide of interest. Accordingly, effective amounts are best determined by the physician administering the compositions and appropriate dosages can be determined readily by one of ordinary skill in the art. After allowing sufficient time for integration and expression (typically 4-15 days, for example), analysis of the serum or other tissue levels of the therapeutic polypeptide and comparison to the initial level prior to administration will determine whether the amount being administered is too low, within the right range or too high. Suitable regimes for initial and subsequent administrations are also variable, but are typified by an initial administration followed by subsequent administrations if necessary. Subsequent administrations may be administered at variable intervals, ranging from daily to annually to every several years. One of skill in the art will appreciate that appropriate immunosuppressive techniques may be recommended to avoid inhibition or blockage of transduction by immunosuppression of the delivery vectors, see e.g., Vilquin et al., (1995) *Human Gene Ther.*, 6:1391-1401.

Formulations for both ex vivo and in vivo administrations include suspensions in liquid or emulsified liquids. The active ingredients often are mixed with excipients which are pharmaceutically acceptable and compatible with the active ingredient. Suitable excipients include, for example, water, saline, dextrose, glycerol, ethanol or the like, and combinations thereof. In addition, the composition may contain minor amounts of auxiliary substances, such as, wetting or emulsifying agents, pH buffering agents, stabilizing agents or other reagents that enhance the effectiveness of the pharmaceutical composition.

Cells

Also described herein are cells and cell lines in which an endogenous BCL11A enhancer sequence is modified by the nucleases described herein (Table 1). The modification may be, for example, as compared to the wild-type sequence of the cell. The cell or cell lines may be heterozygous or homozygous for the modification. The modifications to the BCL11A sequence may comprise indels.

The modification is preferably at or near the nuclease(s) binding site(s), cleavage site(s) and combinations of binding site(s) and cleavage site(s), for example, within 1-300 (or any value therebetween) base pairs upstream or downstream of the site(s) of cleavage, more preferably within 1-100 base pairs (or any value therebetween) of either side of the binding site(s), cleavage site(s), or binding site(s) and cleavage site(s), even more preferably within 1 to 50 base pairs (or any value therebetween) on either side of the binding site(s), cleavage site(s), or binding site(s) and cleavage site(s). In certain embodiments, the modification is at or near the "+58" region of the BCL11A enhancer, for example, at or near a nuclease binding site shown in any of the first column of Table 1.

Any cell or cell line may be modified, for example a stem cell, for example an embryonic stem cell, an induced pluripotent stem cell, a hematopoietic stem cell, a neuronal stem cell and a mesenchymal stem cell. Other non-limiting examples of cells as described herein include T-cells (e.g., CD4+, CD3+, CD8+, etc.); dendritic cells; B-cells. A descendent of a stem cell, including a partially or fully differentiated cell, is also provided (e.g., a RBC or RBC precursor cell). Non-limiting examples other cell lines including a modified BCL11A sequence include COS, CHO (e.g., CHO-S, CHO-K1, CHO-DG44, CHO-DUXB11, CHO-DUKX, CHOK1SV), VERO, MDCK, WI38, V79, B14AF28-G3, BHK, HaK, NS0, SP2/0-Ag14, HeLa, HEK293 (e.g., HEK293-F, HEK293-H, HEK293-T), and perC6 cells as well as insect cells such as Spodopterafugiperda (Sf), or fungal cells such as *Saccharomyces*, *Pichia* and *Schizosaccharomyces*.

The cells as described herein are useful in treating or preventing a disorder, for example, by ex vivo therapies. The nuclease-modified cells can be expanded and then reintroduced into the patient using standard techniques. See, e.g., Tebas et al. (2014) *New Eng J Med* 370(10):901. In the case of stem cells, after infusion into the subject, in vive differentiation of these precursors into cells expressing the functional transgene also occurs. Pharmaceutical compositions comprising the cells as described herein are also provided. In addition, the cells may be cryopreserved prior to administration to a patient.

Any of the modified cells or cell lines disclosed herein may show increased expression of gamma globin. Compositions such as pharmaceutical compositions comprising the genetically modified cells as described herein are also provided Applications The methods and compositions disclosed herein are for modifying expression of protein, or correcting an aberrant gene sequence that encodes a protein expressed in a genetic disease, such as a sickle cell disease or a thalassemia. Thus, the methods and compositions provide for the treatment or prevention of such genetic diseases. Genome editing, for example of stem cells, can be used to correct an aberrant gene, insert a wild type gene, or change the expression of an endogenous gene. By way of non-limiting example, a wild type gene, e.g. encoding at least one globin (e.g., a globin, γ globin, β globin and combinations thereof), may be inserted into a cell (e.g., into an endogenous BCL11A enhancer sequence using one or more nucleases as described herein) to provide the globin proteins deficient or lacking in the cell and thereby treat a genetic disease, e.g., a hemoglobinopathy, caused by faulty globin expression. Alternatively or in addition, genomic editing with or without administration of the appropriate donor, can correct the faulty endogenous gene, e.g., correcting the point mutation in α- or β-hemoglobin, to restore expression of the gene or treat a genetic disease, e.g. sickle cell disease, knock out or alteration (overexpression or repression) of any direct or indirect globin regulatory gene (e.g. inactivation of the γ globin-regulating gene BCL11A or the BCL11A-regulator KLF1). Specifically, the methods and compositions of the invention have use in the treatment or prevention of hemoglobinopathies.

The nucleases of the invention are targeted to the BCL11A enhancer region, known to be required for the expression of BCL11A during erythropoiesis, and hence the down regulation of gamma globin expression. Modification of this enhancer region may result in erythrocytes with increased gamma globin expression, and thus may be helpful for the treatment or prevention of sickle cell disease or beta thalassemia.

The following Examples relate to exemplary embodiments of the present disclosure in which the nuclease comprises a zinc finger nuclease (ZFN). It will be appreciated that this is for purposes of exemplification only and that other nucleases can be used, for example TtAgo and CRISPR/Cas systems, homing endonucleases (meganucleases) with engineered DNA-binding domains, fusions of naturally occurring of engineered homing endonucleases (meganucleases) DNA-binding domains, including combinations of homing endonucleases (meganucleases) with engineered DNA-binding domains and fusions of naturally occurring of engineered homing endonucleases (meganucleases) DNA-binding domains, and heterologous cleavage domains, fusions of meganucleases and TALE proteins, including combinations of heterologous cleavage domains and fusions of meganucleases and TALE proteins.

EXAMPLES

Example 1: Assembly of Zinc Finger Nucleases

ZFNs were assembled against the human BCL11A gene and activity was tested by deep sequencing analysis of DNA isolated from transfected cells as described below. ZFNs specific for the +58 region of the enhancer region were made as described. ZFN pair 51857/51949 has been described previously (see WO 2016/183298).

Example 2: Off Target Analysis

Figure 1B:
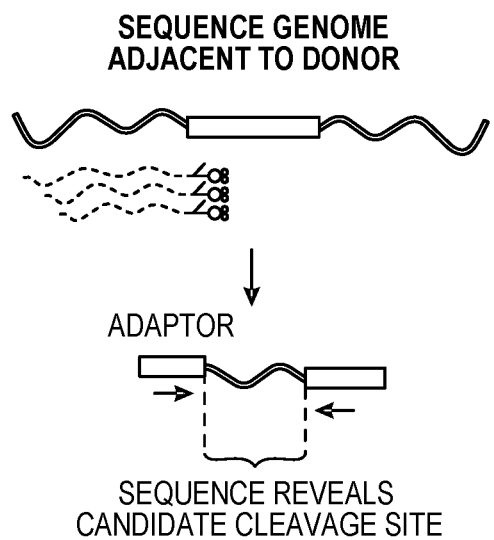

To analyze off target cleavage by the ZFN pairs, a two stage unbiased specificity analysis was performed. In the first stage, (FIG. 1), candidate off-target sites for each ZFN were identified via an oligonucleotide duplex integration site assay using a procedure similar to that described by Tsai et al. ((2015), *Nat Biotechnol* 33(2):187-197. doi: 10.1038/nbt.3117).

The oligonucleotide duplex integration site assay is based on the observation that co-introduction of a nuclease and a short segment of duplex DNA into a target cell results in dplex integration during repair of a fraction of genome cleavage events via the NHEJ DNA repair pathway (Orlando et al., (2010), *Nucleic Acids Res*, 38(15) e152. doi: 10.1093/nar/gkq512; Gabriel et al., (2011), *Nat Biotechnol*. 2011 Aug. 7; 29(9):816-23. doi: 10.1038/nbt.1948; Tsai et al., ibid). Upon integration the duplex provides a permanent tag of the cleavage event. Sites of integration are then identified via ligation of an oligonucleotide adaptor to sheared genomic DNA, followed by 2 rounds of 25 cycles of nested PCR, and deep sequencing of the resulting donor-genome junctions. This assay allows for evaluation of all potential integration sites within the genome.

The integration site assay was performed in K562 cells to maximize donor delivery, ZFN expression, and donor integration. Moreover as K562 cells divide quickly (doubling time approximately 24 hours) they are expected to impose minimal epigenetic restrictions on the ability of ZFNs to cleave cellular targets. Cells ($2 \times 10^5$) were electroporated with 0.47 µg of oligonucleotide duplex donor and 400 ng of each ZFN-encoding mRNA using an Amaxa shuttle and settings optimized for maximal on-target activity of the ZFNs. Four replicate samples were prepared for each combination of oligo and mRNA. On day 7 post-transfection, genomic DNA was isolated for each sample (Qiagen DNeasy Blood and Tissue Kit) and 400 ng (133000 haploid genomes) was used as input for the amplification protocol outlined in FIG. 1. Samples were then processed essentially as described (Tsai et al. ibid). Final products were pooled, quantified, and sequenced on a MiSeq Instrument (Illumina) using a v2 300 cycle sequencing kit with paired-end 150 bp reads and 8 bp/16 bp dual index reads to detect the sample barcodes on each end of the amplicon.

To generate a list of candidate off target sites, sequencing data were filtered for correct priming sequence, followed by trimming of adapter sequences and mapping to the genome. Next, junction coordinates were mapped, and the duplex-genome junction, as well as the position of the break caused by DNA shearing, were used to identify distinct integration events. Integration events were then processed to identify clusters of integrations in close proximity within the genome (minimum of 4 distinct integration events within 100 bp of each other, summed across all replicates). Clusters residing on contigs that were unmappable in the hg38 assembly (i.e. chrUn in hg38) were removed from further analysis. Clusters mapping to repetitive loci (median of three or more hits to the genome across all sequences in a cluster) were also removed as prior experience has shown these to be amplification artifacts. Remaining clusters were scored as candidate ZFN cleavage sites if they were derived from at least 2 replicate ZFN treated samples (of 4 total) and exhibited ≥5 fold excess of integration events in ZFN treated samples versus controls. Candidate cleavage sites were ranked by the total number of unique integrations in the ZFN treated samples. Candidate loci identified via this analysis are provided in FIG. 2 for ZFN pair 51857/51949, ranked by integrant count.

Example 3: Optimization of ZFNs

Figure 3C:
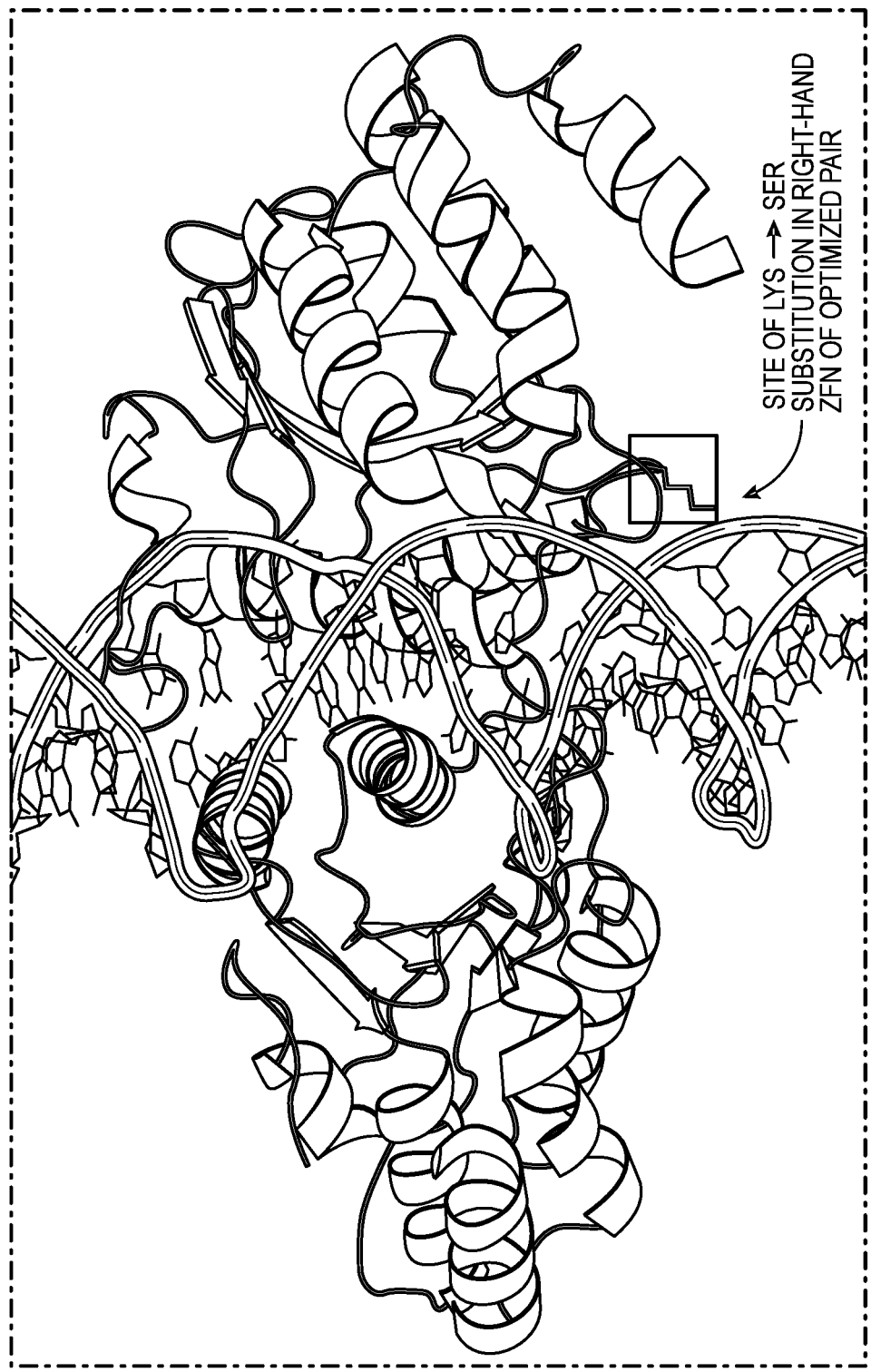

To decrease off target cleavage, a strategy for nuclease optimization in which nonspecific phosphate contacts are selectively removed to bring about global suppression off-target cleavage (Guilinger et al. (2014) *Nat Methods*. 11(4): 429-35. doi: 10.1038/nmeth.2845; Kleinstiver et al. (2016) *Nature* 529(7587):490-5. doi: 10.1038/nature16526; Slaymaker et al. (2016) *Science*) 351(6268):84-8. doi: 10.1126/science.aad5227) was adopted (see U.S. Provisional Application Nos. 62/443,981 and 62/378,978). Amino acid substitutions were made at a key position within the zinc finger framework that interacts with the phosphate backbone of the DNA (Pavletich and Pabo, (1991) *Science* 252(5007): 809-17; Elrod-Erickson et al. (1996) *Structure* 4(10):1171-80) (FIG. 3A-3B) as well as at a single position in the right ZFN Fold domain also predicted to make a phosphate contact (FIG. 3C).

Specificity was further improved by allowing independent expression of each ZFN from two separated mRNAs, which enables optimization of delivery ratios. These efforts yielded optimized ZFN pairs that are highly related to the original one, differing by substitutions that decrease the energetics of interaction with the DNA phosphate backbone but that minimally or do not impact sequence specific base recognition. Consistent with this, the integration site assay yielded 455 loci for potential targets of ZFN cleavage for the original 51857/51949 pair. For the optimized pair, a much smaller number of loci were identified for further examination as potential targets of ZFN cleavage (72 total) by this analysis. For both pairs, the intended target within the BCL11A enhancer was the top ranked locus. Moreover a much higher fraction of integration events was noted at the BCL11A enhancer for the optimized pair, consistent with its greater specificity.

It is important to note that in defining the sequence data processing pipeline, key parameters were chosen conservatively, to err on the side of including as many candidate off target loci as feasible instead of filtering them out. This was done to ensure that every locus that might represent a bona fide cleavage site for the optimized ZFNs would be identified and tested in follow-up indel studies, even at the cost of accepting a much greater number that would become false positives. It was expected that the first stage of analysis would yield a large set of candidate loci for each ZFN pair, of which the large majority (particularly for the optimized ZFNs) would not represent true off-target cleavage sites but rather background events that would prove negative for cleavage in follow-up indel studies.

In the second stage of analysis, candidate off-target loci identified via the integration site assay were screened for evidence of modification (e.g., the presence of indels) in ZFN-treated CD34+ HSPC.

In particular, human CD34+ HSPC derived from mobilized peripheral blood were treated with the original and optimized ZFN pairs using clinical scale and clinical conditions for RNA transfection (120 μg/mL of mRNA for the original ZFN pair and 100 μg/mL of mRNA for the optimized pair). Genomic DNA was isolated 2 days post-transfection, followed by PCR amplification of candidate off-target loci and deep sequencing to quantify indel levels. For both the original and optimized ZFN pairs, the same set of 137 candidate off-target loci were screened at this step, along with a smaller number of candidate off-target sites that had been identified via other methods in earlier studies with the original ZFNs.

Figure 4:
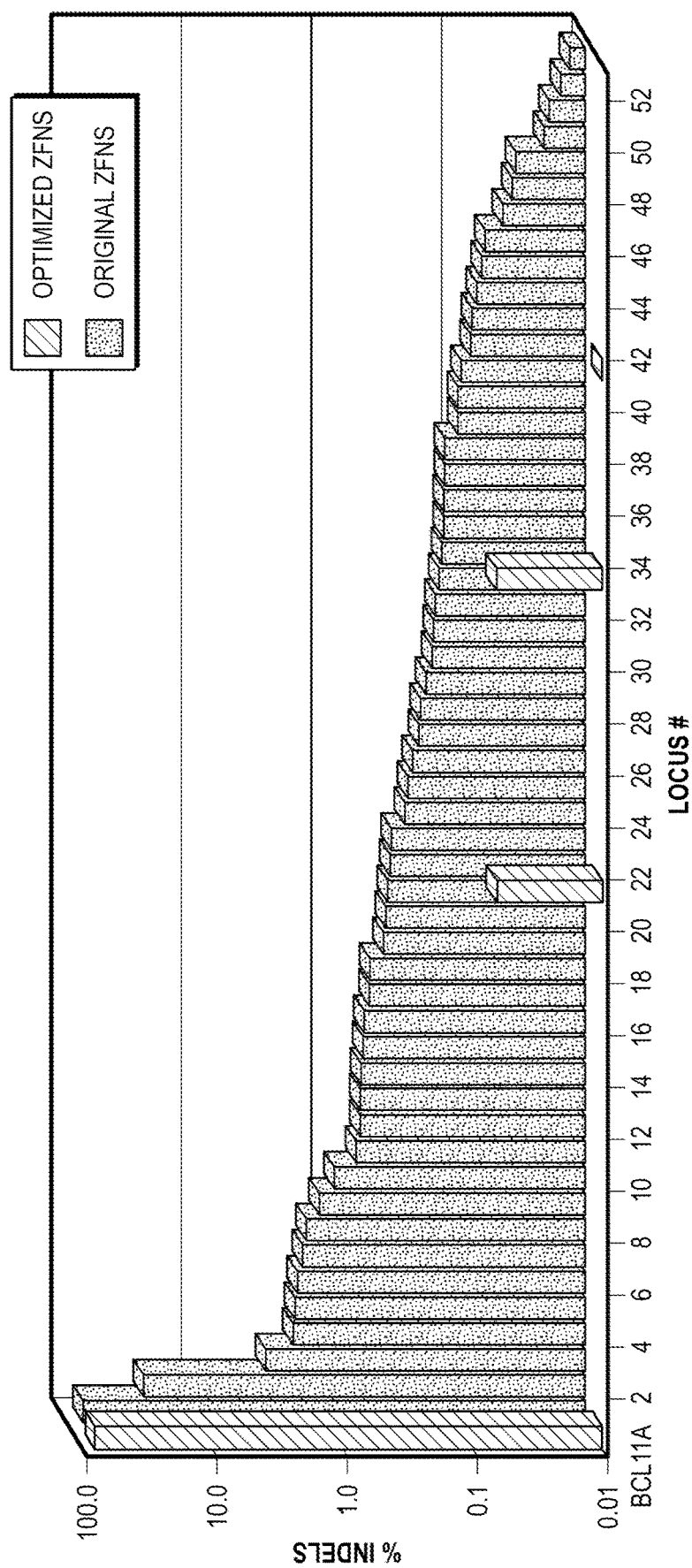
FIG. 4 is a graph comparing modification levels via treatment of CD34 cells with either the original 51857/51949 pair or with the optimized 63014/65722 pair at various tested loci. Shown across the bottom or on the x-axis, are the loci identified as potential cleavage targets, with the percent indels for each site shown on the vertical or γ-axis. Note that the γ-axis is shown in a log scale. The dark gray bars show the loci cleaved by the 51857/51949 pair, and the amount of cleavage detected, while the light gray bars are those loci cleaved by the optimized pair where nearly all cleavage measured is at the targeted BCL11γ target sequence.

The results showed that the optimized ZFNs are markedly more specific than the original pair. This is apparent not only from the number of loci that were scored positive for evidence of ZFN cleavage (52 for the original pair vs 3 for the optimized pair), but also from the observed indel levels, which for the optimized pair were much lower. FIG. 4 shows plots of indel values at every locus exhibiting evidence of ZFN cleavage in this study (note log scale of y axis). Aggregating off-target indels across all such loci indicates a reduction in off-target activity of 300 fold (46.5% aggregate off-target indels for the original pair, vs 0.15% off-target indels for the optimized pair). This reduction in off-target activity was achieved without any loss in activity at the intended target site (72.5% indels for the original pair vs 81.9% for the optimized ZFNs). In these studies, the original pair (or parental pair) was 51857/51949, while the optimized ZFN pair was 63014/65722 (see below).

The nuclease designs are shown below in Table 1:

TABLE 1

ZFN pairs specific for +58 BCL11A enhancer region

| SBS # (target site, 5'-3') | Design [Helix Sequence, SEQ ID] [Mutations to finger backbone] | | | | | | Linker Fok mutants |
|---|---|---|---|---|---|---|---|
| | F1 | F2 | F3 | F4 | F5 | F6 | |
| Left partner | | | | | | | |
| 51857 aaAGCAACtG TTAGCTTGCA Ctagacta (SEQ ID NO: 1) | DQSNLRA (SEQ ID NO: 19) none | RNFSLTM (SEQ ID NO: 20) none | STGNLTN (SEQ ID NO: 21) none | TSGSLTR (SEQ ID NO: 22) none | DQSNLRA (SEQ ID NO: 19) none | AQCCLFH (SEQ ID NO: 23) none | L7c5 ELD |
| 63014 aaAGCAACtG TTAGCTTGCA Ctagacta (SEQ ID NO: 1) | DQSNLRA (SEQ ID NO: 19) Qm5 | RNFSLTM (SEQ ID NO: 20) none | STGNLTN (SEQ ID NO: 21) Qm5 | TSGSLTR (SEQ ID NO: 22) none | DQSNLRA (SEQ ID NO: 19) Qm5 | AQCCLFH (SEQ ID NO: 23) none | L7c5 ELD |
| 65459 aaAGCAACtG TTAGCTTGCA Ctagacta (SEQ ID NO: 1) | DQSNLRA (SEQ ID NO: 19) Qm14Qm5 | RNFSLTM (SEQ ID NO: 20) none | STGNLTN (SEQ ID NO: 21) Qm5 | TSGSLTR (SEQ ID NO: 22) none | DQSNLRA (SEQ ID NO: 19) Qm5 | AQCCLFH (SEQ ID NO: 23) none | L7c5 ELD |
| Right Partner | | | | | | | |
| 51949 caCAGGCTCC AGGAAGGgtt TGGCCTCT (SEQ ID NO: 2) | RNDHRTT (SEQ ID NO: 24) none | QKAHLIR (SEQ ID NO: 25) none | QKGTLGE (SEQ ID NO: 26) none | RGRDLSR (SEQ ID NO: 34) none | RRDNLHS (SEQ ID NO: 27) none | N/A N/A | L0 KKR |
| 65722 caCAGGCTCC AGGAAGGgtt TGGCCTCT (SEQ ID NO: 2) | RNDHRTT (SEQ ID NO: 24) Qm5 | QKAHLIR (SEQ ID NO: 25) Qm5 | QKGTLGE (SEQ ID NO: 26) none | RGRDLSR (SEQ ID NO: 34) Qm5 | RRDNLHS (SEQ ID NO: 27) none | N/A N/A | L0 KKR K525S |

TABLE 1-continued

ZFN pairs specific for +58 BCL11A enhancer region

| SBS # (target site, 5'-3') | Design [Helix Sequence, SEQ ID] [Mutations to finger backbone] | | | | | | Linker Fok mutants |
|---|---|---|---|---|---|---|---|
| | F1 | F2 | F3 | F4 | F5 | F6 | |
| 65526 caCAGGCTCC AGGAAGGgtt TGGCCTCT (SEQ ID NO: 2) | RNDHRTT (SEQ ID NO: 24) Qm5 | QKAHLIR (SEQ ID NO: 25) Qm5 | QKGTLGE (SEQ ID NO: 26) none | RGRDLSR (SEQ ID NO: 34) Qm5 | RRDNLHS (SEQ ID NO: 27) Qm5 | N/A N/A | L0 KKR R416S |
| 65549 caCAGGCTCC AGGAAGGgtt TGGCCTCT (SEQ ID NO: 2) | RNDHRTT (SEQ ID NO: 24) Qm5 | QKAHLIR (SEQ ID NO: 25) Qm5 | QKGTLGE (SEQ ID NO: 26) Qm5 | RGRDLSR (SEQ ID NO: 34) Qm5 | RRDNLHS (SEQ ID NO: 27) none | N/A N/A | L0 KKR K525S |
| 65550 caCAGGCTCC AGGAAGGgtt TGGCCTCT (SEQ ID NO: 2) | RNDHRTT (SEQ ID NO: 24) Qm5 | QKAHLIR (SEQ ID NO: 25) Qm5 | QKGTLGE (SEQ ID NO: 26) none | RGRDLSR (SEQ ID NO: 34) Qm5 | RRDNLHS (SEQ ID NO: 27) Qm5 | N/A N/A | L0 KKR K525S |

Table 1 shows characterizing information pertaining to each ZFN. Starting from the left, the SBS number (e.g. 51857) is displayed with the DNA target that the ZFN binds to displayed below the SBS number. Next are shown the amino acid recognition helix designs for fingers 1-6 or 1-5 (subdivided column 2 of Table 1). Also shown in Table 1 under the appropriate helix designs are mutations made to the ZFP backbone sequences of the indicated finger, as described in U.S. Provisional Patent Application Nos. 62/378,978 and 62/443,981. In the notation used in Table 1, "Qm5" means that at position minus 5 (relative to the helix which is numbered −1 to +6) of the indicated finger, the arginine at this position has been replaced with a glutamine (Q), while "Qm14" means that the arginine (R) normally present in position minus 14 has been replaced with a glutamine (Q). "None" indicates no changes outside the recognition helix region. Thus, for example, SBS #63014 includes the Qm5 mutation in fingers 1, 3 and 5 while fingers 2, 4 and 6 do not have mutations to the zinc finger backbone (e.g., the zinc finger sequence outside the recognition helix region).

Finally, the right-most column of Table 1 shows the linker used to link the DNA binding domain to the Fold cleavage domain (e.g., "L7c5" (LRGSISRARPLNPHP (SEQ ID NO:5), as described for example in U.S. Pat. No. 9,567,609) is displayed on top line of the column, with the sites of the Fold phosphate contact mutations and dimerization mutations shown in the box below the linker designation. In specifics, indicated on top line of the Fok mutants box is the type of mutation found in the dimerizing domain (e.g., ELD or KKR as described for example in U.S. Pat. No. 8,962,281). Below the dimerization mutant designations is shown any mutations present in the Fold domain made to remove a non-specific phosphate contact shown on the bottom (e.g. K525S or R416S where serine residues at amino acid positions 525 or 416 have been substituted for either a lysine or arginine, respectively as described in U.S. Provisional Patent Application Nos. 62/378,978 and 62/443,981). Thus, for example, in SBS #63014, the linker is an L7c5 linker and the Fok cleavage domain includes the ELD dimerization mutants and no phosphate contact mutations. Further, for SBS #65722, the linker is an L0 linker (LRGSQLVKS (SEQ ID NO:6), also referred to as the 'standard' linker, see U.S. Pat. No. 9,567,609) and the FokI cleavage domain includes the KKR dimerization mutations and the K525S FokI phosphate contact mutation.

All ZFNs were tested for functionality (cleavage activity as determined by assaying for indels as described in Example 4 below) and found to be active.

Furthermore, in order to determine which ZFN designs were the most specific, indel analyses of known sites of off-target cleavage by the original ZFN pair were performed in ZFN-treated CD34+ HSPC. To accomplish this, human CD34+ HSPC derived from mobilized peripheral blood were treated with the original and optimized ZFN pairs using clinical conditions and mRNA concentrations (120 μg/mL for the original ZFN pair and 100 μg/mL for the optimized pair). Genomic DNA was isolated 2 days post-transfection from these cells and untreated controls, followed by PCR amplification of each candidate locus and deep sequencing to quantify indel levels.

Modification levels at each locus were determined by paired-end deep sequencing on an Illumina MiSeq using a 300 cycle cartridge. Paired sequences were merged, adaptor trimmed via SeqPrep filtered for a quality score of ≥15 across all bases, and then mapped to the human genome (hg38 assembly). Sequences that mapped to an incorrect locus were discarded. Sequences shorter than the wild-type amplicon by >70 bp or >70% were removed in order to minimize primer-dimer products. A Needleman-Wunsch alignment (Needleman and Wunsch, (1970), *J Mol Biol* 48(3):443-53)) was performed between the target amplicon and each MiSeq read to map indels. Indels in aligned sequences were defined as described in Gabriel et al. 2011 (ibid) except that indels 1 bp in length were also accepted to avoid undercounting real events. Note that a fraction of loci either did not amplify or did not sequence, or were rejected from analysis due to high background (>1% modification in control samples) or insufficient sequencing depth (<10000 reads). The results of this analysis and comparison to the 'parent' 51857/51949 ZFN pair are provided below in Table 2.

TABLE 2

Off target cleavage analysis

| ZFN dimer | | µg RNA L:R | BCL11A % indels | Off-target: # of loci | | | # indel-positive OT loci | | In parent? Capture/ confirmed |
|---|---|---|---|---|---|---|---|---|---|
| Left | Right | | | target | PCR'd | Analyzable | P < 0.05 | manual | |
| 51857 | 51949 | 60:60 | 73.0 | 23 | 21 | 17 | 15 | 17 | — |
| 63014 | 65722 | 60:15 | 82.2 | 31 | 24 | 14 | 0 | 4 | 4/3 |
| 63014 | 65526 | 60:15 | 81.2 | 23 | 22 | 9 | 3 | 4 | 4/4 |
| 63014 | 65527 | 60:60 | 81.4 | 30 | 24 | 10 | 4 | 4 | 4/2 |
| 63014 | 65549 | 60:60 | 80.0 | 30 | 24 | 13 | 0 | 2 | 2/1 |
| 63014 | 65550 | 60:60 | 79.8 | 30 | 24 | 9 | 0 | 1 | 1/1 |
| 65459 | 65526 | 60:15 | 76.9 | 23 | 19 | 14 | 0 | 2 | 2/2 |

Example 4: Activity of ZFNs in Human CD34+ Cells

For in vitro testing, the nucleases were tested in CD34+ cells. ZFNs were supplied as mRNAs, where the mRNAs were made in vitro as follows: plasmids comprising the genes encoding the ZFN are linearized and used for in vitro mRNA transcription using the mMessage mMachine® T7 Ultra Kit (Ambion/Applied Biosystems). The mRNA was then purified using an RNeasy® mini kit (Qiagen).

CD34+ cells were isolated from mobilized peripheral blood and maintained in X-VIVO 10 medium supplemented with penicillin, streptomycin and glutamine as well as StemSpan CC110 and incubated at 37° C. and 5% CO2. Cells were transfected 48 hours post-isolation or post-thaw. A small aliquot was mixed 1:1 with trypan blue solution 0.4% (w/v) in PBS (Corning) and the cell numbers were determined on a TC20 Automated Cell Counter (Bio-Rad).

For large scale transfections, cells were washed with MaxCyte Electroporation Buffer (Maxcyte) and re-suspended at 3 to 5e7 cells per mL in Electroporation buffer in 100 µL. Typically, mRNA concentrations between 60 µg/mL and 120 µg/mL were used to screen candidate ZFN sets. Cells were then grown in growth media at 3e6 cells per mL for 18 hours at 30° C. and then diluted to 1e6 cells per 20 mL for an additional 24 hours at 37° C. For determination of cleavage activity, genomic DNA was isolated 2-3 days post-transfection, and the level of gene modification at the BCL11A enhancer locus was measured via deep sequencing on a MiSeq sequencer (Illumina).

The ZFN pairs from Table 1 were tested in CD34+ cells and the activity results are shown below in Table 3.

TABLE 3

Activity of ZFN pairs against BCL11A target

| Right ZFN | Left ZFN | R ZFN conc. (µg) | L ZFN conc. (µg) | Indels (%) |
|---|---|---|---|---|
| 51857 | 51949 | 60 | 60 | 72.98 |
| 63014 | 65722 | 15 | 60 | 80.62 |
| 63014 | 65722 | 60 | 15 | 82.19 |
| 63014 | 65526 | 60 | 15 | 81.22 |
| 63014 | 65527 | 60 | 60 | 81.43 |

TABLE 3-continued

Activity of ZFN pairs against BCL11A target

| Right ZFN | Left ZFN | R ZFN conc. (µg) | L ZFN conc. (µg) | Indels (%) |
|---|---|---|---|---|
| 63014 | 65549 | 60 | 60 | 79.82 |
| 63014 | 65550 | 60 | 60 | 79.96 |
| GFP control | | | | 0.07 |

In addition to analyzing the nuclease activity in CD34+ cells prior to erythroid differentiation, edited cells were also differentiated in vitro into erythroid cells. The protocol followed was based on Bauer et al. (2012) *Blood* 118(15): 2945-53). In brief, the protocol below was followed:

Day 0 to Day 7: $4 \times 10^4$ CD34+ cells were cultured at a density of 2×104/mL in differentiation medium (EDM) (Iscove's Modified Dulbecco's Medium [IMDM], 330 µg/mL Transferrin, 10 µg/mL Human Insulin, 2 U/mL Heparin sodium, 5% Human AB+ plasma) in the presence of $10^{-6}$ M hydrocortisone, 100 ng/mL stem cell factor (SCF), 5 ng/mL IL 3, and 3 IU/mL erythropoietin (EPO).

Day 4: Cells resuspended in fresh EDM containing SCF, IL-3, EPO, and hydrocortisone.

Day 7 to Day 11: Cells were resuspended at a density of $1.5 \times 10^5$ cells per fresh mL of EDM supplemented with SCF and EPO.

Day 11 to Day 21: On day 11, cells were replated at $1 \times 10^6$/mL in fresh EDM supplemented with EPO. Cells were subsequently replated in this same media at $5 \times 10^6$/mL on day 14. Growth plateaus during this period of time between day 14 to 18, when cell viabilities began to drop until termination of the cultures at day 21.

Cell counts were taken at the time of seeding and throughout the differentiation by measuring Acridine Orange positivity and Propidium Iodide exclusion (AOPI) using a Nexcelom Bioscience Cellometer K2 with the AOPI Erythroid Assay mode with fluorescence channel 1 (AO) set to 700 milliseconds and fluorescence channel 2 (PI) set to 5000 milliseconds.

The percentage of enucleated cells was determined at day 21 of the differentiation using the following protocol. The enucleation rate was comparable among untransfected controls and ZFN-transfected samples with percentages 59-63% from these two groups:

1. Cell count
2. 100,000 cells, spin down at 450× g, 5 min, RT.
3. Resuspend in 50 μL PBS-BSA+1 μL GlyA-FITC (DAKO).
4. Stain for 15 min in fridge.
5. Add 1 mL PBS-BSA, vortex, spin down.
6. Resuspend in 250 μL (2 drops NucRed per mL).
7. Acquire on FACS Canto using the APC channel for NucRed.
8. Nucleated erythroid cells will be in the GlyA positive NucRed negative/low fraction and erythroblasts will be in the double GlyA-NucRed positive fraction.

BCL11A gene modification was measured by MiSeq deep sequencing in DNA samples harvested a) 48 hours after electroporation b) on the day of thawing the cells, at the time when the in vitro differentiation was started and c) at day 14 of the in vitro erythroid differentiation. While the differentiation was performed for 21 days, the day 14 timepoint for DNA analysis was chosen since it is prior to enucleation of a large fraction of the erythroid cells which results in a loss of DNA recovery. The observed modification percentages at the BCL11A enhancer are listed in Table 4 together with details of the transfection conditions.

TABLE 4

BCL11A Gene Modification Levels by MiSeq Analysis

| CD34+ Cell Prep | Transfection | BCL11A Gene Modification (%) | | |
|---|---|---|---|---|
| | | Day 2 post TF | Post-Thaw | Day 14 of differentiation |
| Prep #1 | 80 μg/mL 63014 + 20 μg/mL 65722 | 78.6 | 81.4 | 72.0 |
| | Untransfected | 0.1 | 0.2 | 0.2 |
| Prep#2 | 80 μg/mL 63014 + 20 μg/mL 65722 | 75.4 | 77.3 | 72.3 |
| | Untransfected | 0.1 | 0.1 | 0.0 |

These data show that CD34+ cell transfection with optimized pair 63014 and 65722 mRNA leads to very efficient gene modification at the BCL11A enhancer target site (>75% of alleles modified) and that the modification is maintained very well (>90% retention of the modification) after freezing and thawing of the cells and after erythroid differentiation.

The ZFN pair 63014/65722 was selected for further analysis. The amino acid sequences for these ZFNs are shown below, where each comprises a nuclear localization signal (NLS, Kalderon et al. (1984) *Cell* 39 (3 Pt 2):499-509) and a hydrophilic peptide (Hopp et al. (1988) *Nat Biotechnol* 6:1204-10) which enhances on-target ZFN activity, both fused to the N-terminal coding sequence. Thus, the mRNA and amino acid sequences of the ZFNs are as follows:

63014 mRNA (1725 nt)
(SEQ ID NO: 28)
5'ggagacaagcuuugaauuacaagcuugcuuguucuuuuugcagaagc ucagaauaaacgcucaacuuuggcagaucgaauucgccauggacuacaaa gaccaugacggugauuauaaagaucaugacaucgauuacaaggaugacga ugacaaggauggccccaagaagaagaggaaggucggcauccacgggguac ccgccgcuauggcugagaggcccauccagugucgaaucugcaugcagaac uucagugaccaguccaaccugcgcgcccacaaccgcacccacaccggcga gaagccuuuugccugugacauuuguggaggaaauuugcccgcaacuucu cccugaccaugcauaccaagauacacacgggcagccaaaagcccuuccag ugucgaaucugcaugcagaacuucaguuccaccggcaaccugaccaacca cauccgcacccacaccggcgagaagccuuuugccugugacauuugugga ggaaauuugccaccuccggcucccugacccgccauaccaagauacacacg cacccgcgcgccccgaucccgaagccuuccagugucgaaucugcaugca gaacuucagugaccaguccaaccugcgcgcccacauccgcacccacaccg gcgagaagccuuuugccugugacauuuguggaggaaauuugccgcccag uguugucguuccaccauaccaagauacaccugcgggauccaucagcag agccagaccacugaacccgcacccggagcuggaggagaagaaguccgagc ugcggcacaagcugaaguacgugccccacgaguacaucgagcugaucgag aucgccaggaacagcacccaggaccgcauccuggagaugaaggugaugga guucuucaugaagguguacggcuacaggggaaagcaccugggcggaagca gaaagccugacggcgccaucuauacaguggggcagccccaucgauuacggc gugaucguggacacaaaggccuacagcggcggcuacaaucugccuaucgg ccaggccgacgagauggagagauacguggaggagaaccagacccgggaua gcaccucaaccccaacgaguggugaagguguaccuagcagcgugacc gaguucaaguuccuguucgugagcggccacuucaagggcaacuacaaggc ccagcugaccaggcugaaccacaucaccaacugcaauggcgccgugcuga gcguggaggagcugcugaucggcggcgagaugaucaaagccggcacccug acacuggaggaggugcggcgcaaguucaacaacggcgagaucaacuucag aucuugauaacucgagucuagaagcucgcuuucuugcuguccaauuucua uuaaagguuccuuuguucccuaaguccaacuacuaaacuggggauauua ugaagggccuugagcaucuggauucugccuaauaaaaaacauuuauuuuc auugcugcguagaagcucgcuuucuugcuguccaauuucuauuaaaggu uccuuuguucccuaaguccaacuacuaaacuggggauauuaugaagggc cuugagcaucuggauucugccuaauaaaaaacauuuauuuucauugcugc gggacauucuuaauuaaaaaaaaaaaaaaaaaaaaaaaaaaaaaaaaaaa aaaaaaaaaaaaaaaaaaaaaaaacuag.

63014 amino acid sequence (recognition helix regions are underlined; linker is shown in upper case italics; mutations to fingers 1, 3 and 5 backbone residues are shown in double-underlining; the dimerization domain mutations (ELD) are shown in bold and italics; hydrophilic peptide is indicated in lower case text; and the nuclear localization signal (NLS) is shown in lowercase italics):

(SEQ ID NO: 29)

MdykdhdgdykdhdidykddddkMApkkkrkvGIHGVPAAMAERPFQCRICMQNFSDQSNL

RAHIRTHTGEKPFACDICGRKFARNFSLTMHTKIHTGSQKPFQCRICMQNFSSTG

NLTNHIRTHTGEKPFACDICGRKFATSGSLTRHTKIHTHPRAPIPKPFQCRICMQNF

SDQSNLRAHIRTHTGEKPFACDICGRKFAAQCCLFHHTKIHLRGSISRARPLNPHPE

LEEKKSELRHKLKYVPHEYIELIEIARNSTQDRILEMKVMEFFMKVYGYRGKHLG

GSRKPDGAIYTVGSPIDYGVIVDTKAYSGGYNLPIGQADEMERYVEENQTRDKH

LNPNEWWKVYPSSVTEFKFLFVSGHFKGNYKAQLTRLNHITNCNGAVLSVEELL

IGGEMIKAGTLTLEEVRRKFNNGEINFRS.

65722 mRNA (1680 nucleotides):

(SEQ ID NO: 30)

5' gggagacaagcuugaauacaagcuugcuuguucuuuuugcagaagcucagaauaaacgcucaacuuuggcagau cgaauucgccuagagaucuggcggcggagagggcagaggaagucuucuaaccugcggugacguggaggagaaucc cggcccuaggaccauggacuacaaagaccaugacggugauuauaaagaucaugacaucgauuacaaggaugacgau gacaagauggcccccaagaagaagaggaaggucggcauucauggggguacccgccgcuauggcugagaggcccuucc agugucgaaucugcaugcagaaguuugcccgcaacgaccaccgcaccacccauaccaagauacacacgggcgagaag cccuuccagugucgaaucugcaugcagaacuucagucagaaggcccaccugauccgccacauccgcacccacaccgg cgagaagcccuuugccugugacauuugugggaggaaauuugcccagaagggcacccugggcgagcauaccaagaua cacacgggaucucagaagcccuuccagugucgaaucugcaugcagaacuucagucgcggccgcgaccugucccgcc acauccgcacccacaccggcgagaagcccuuugccugugacauuugugggaggaaauuugcccgccgcgacaaccu gcacucccauaccaagauacaccugcggggaucccagcuggugaagagcgagcuggaggagaagaaguccgagcug cggcacaagcugaaguacgugccccacgaguacaucgagcugaucgagaucgccaggaacagcacccaggaccgcau ccuggagaugaaggugauggaguucuucaugaagguguacggcuacaggggaaagcaccugggcggaagcagaaa gccugacggcgccaucuauacagugggcagccccaucgauuacggcgugaucguggacacaaaggccuacagcggc ggcuacaaucugccuaucggccaggccgacgagaugcagagauacgugaaggagaaccagacccggaauaagcacau caaccccaacgagugguggaaggguacccuagcagcgugaccgaguucaaguccuguucgugagcggccacuuc agcggcaacuacaaggcccagcugaccaggcugaaccgcaaaaccaacugcaauggcgccgugcugagcguggagga gcugcugaucggcggcgagaugaucaaagccggcaccccugacacuggaggaggugcggcgcaaguucaacaacggc gagaucaacuucugauaacucgagucuagaagcucgcuuucuugcuguccaauuucuauuaaaggguuccuugu cccuaagccaacuacuaaacuggggauauuaugaagggccuugagcaucuggauucugccuaauaaaaaacauu uauuuucauugcugcgcuagaagcucgcuuucuugcuguccaauuucuauuaaaggguuccuuguucccuaaguc caacuacuaaacuggggauauuaugaagggccuugagcaucuggauucugccuaauaaaaaacauuuauuuucau ugcugcgggacauucuuaauuaaaaaaaaaaaaaaaaaaaaaaaaaaaaaaaaaaaaaaaaaaaaaaaaaaaaaa aacuag.

65722 amino acid sequence (recognition helix regions are underlined; linker is shown in upper case italics; hydrophilic peptide is in lower case; nuclease localization signal is in lower case italics; mutations to fingers 1, 2 and 4 backbone residues are shown in double-underlining; the dimerization domain mutations (ELD) are shown in bold and italics; and the FokI phosphate contact mutation(s) is shown in wavy underlining):

(SEQ ID NO: 31)
Mdykdhdgdykdhdidykddddk MA*pkkkrkv*GIHGVPAAMAERPFQCRICMQKFARNDHR

TTHTKIHTGEKPFQCRICMQNFSQKAHLIRHIRTHTGEKPFACDICGRKFAQKGTL

GEHTKIHTGSQKPFQCRICMQNFSRGRDLSRHIRTHTGEKPFACDICGRKFARRD

NLHSHTKIH*LRGSQLVKS*ELEEKKSELRHKLKYVPHEYIELIEIARNSTQDRILEMK

VMEFFMKVYGYRGKHLGGSRKPDGAIYTVGSPIDYGVIVDTKAYSGGYNLPIGQ

ADEMQRYV*KEN*QTRNKHINPNEWWKVYPSSVTEFKFLFVSGHFSGNYKAQLTR

LN*RK*TNCNGAVLSVEELLIGGEMIKAGTLTLEEVRRKFNNGEINF.

Example 5: Assessment of Globin Levels in Erythrold Progeny

Figure 5A:
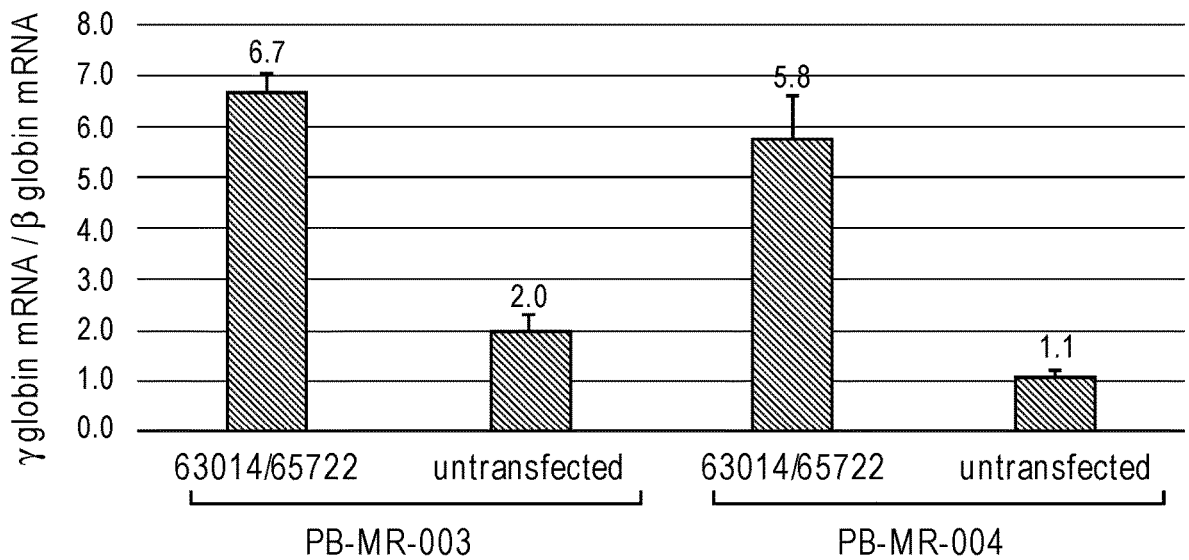
FIGS. 5A and 5B are graphs depicting the relative ratios of globin mRNAs made in hCD34+ cells following treatment with BCL11A specific ZFNs and erythroid differentiation. CD34+ cells derived from two healthy human donors (PB-MR-003 or PB-MR-004) were treated or not treated with the ZFN pair and then α, β, and γ globin expression was analyzed. The best method to determine the amount of γ globin mRNA found following ZFN treatment is to express the change in expression as either a ratio of γ globin to β globin (FIG. 5A), or γ globin to α globin mRNA (FIG. 51B).
Figure 5B:
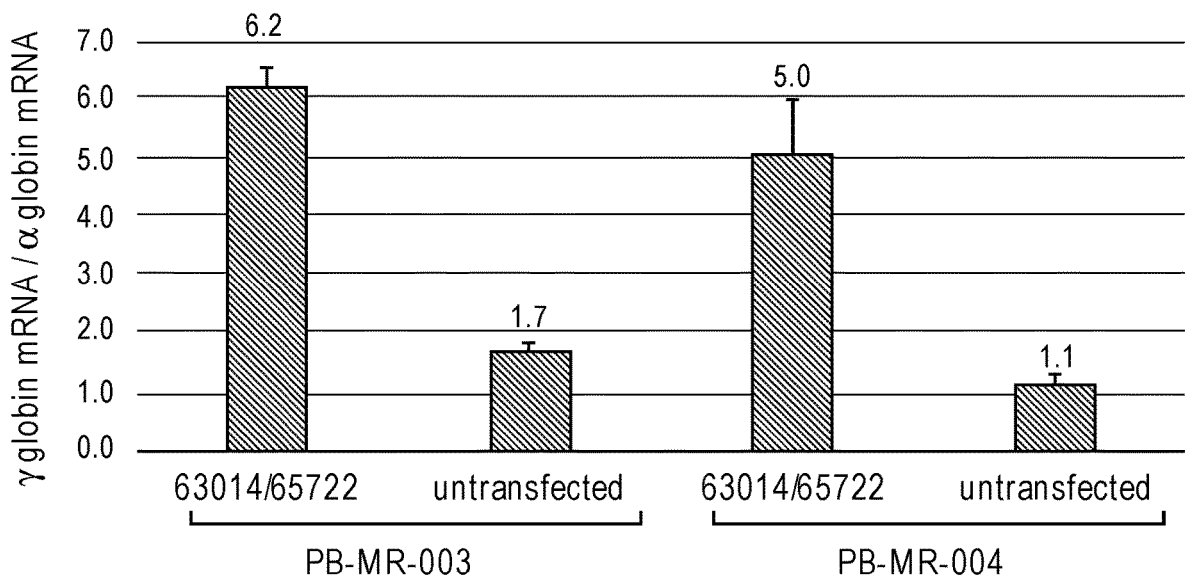

Levels of α-, β- and γ-globin mRNA in cellular mRNA isolated at day 14 of the differentiation (before overall mRNA levels decline dramatically in the course of enucleation and erythroid maturation) were determined by RT-qPCR for the two cell preps shown above in Table 4. The γ-globin mRNA values are shown normalized relative to the β-globin mRNA (FIG. 5A) or to the α-globin mRNA values (FIG. 5B) from the same samples (using arbitrary units based on the ratio in the untransfected RT-PCR standard defined as 1).

Figure 6:
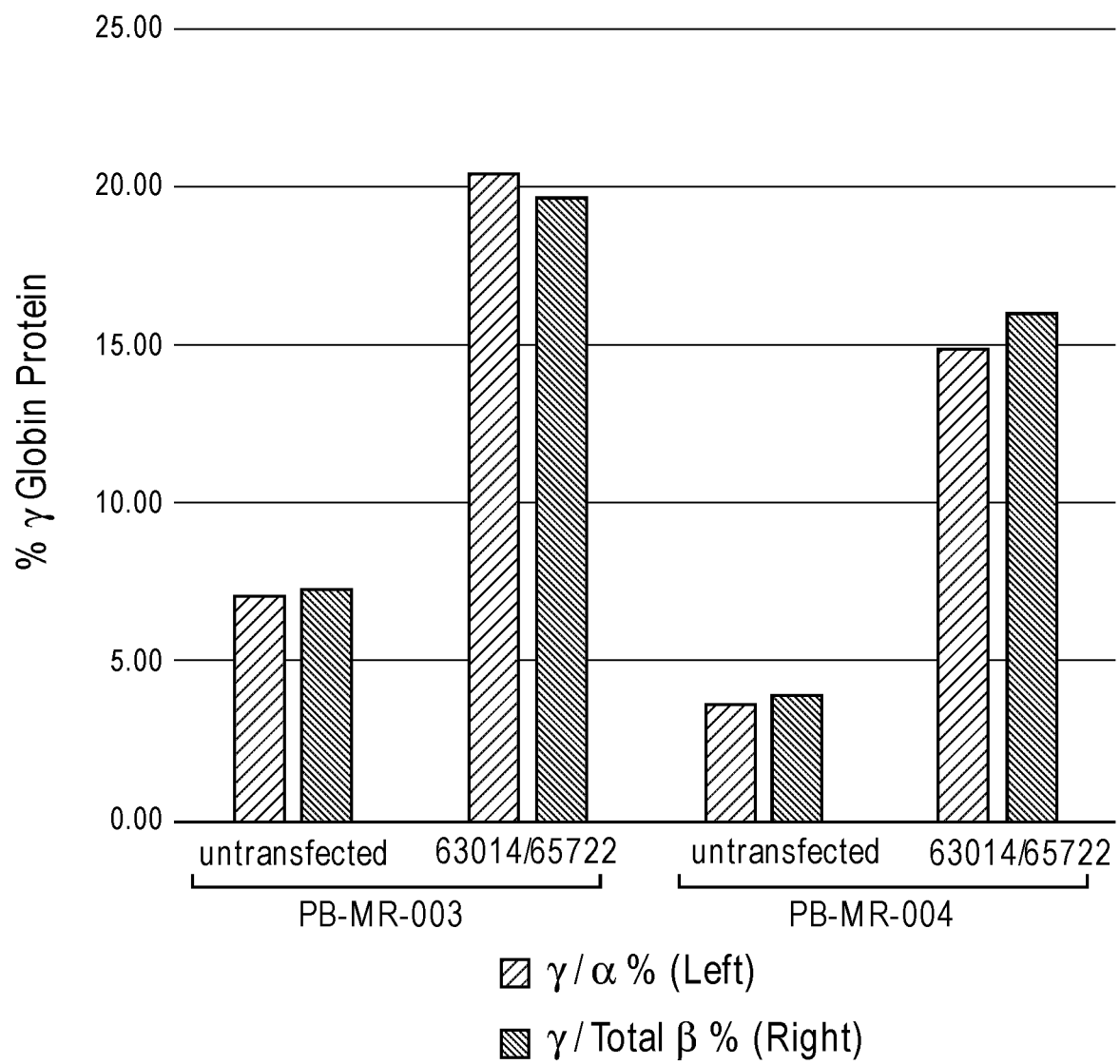
FIG. 6 is a graph depicting the relative amounts of γ-globin protein produced in the treated CD34+ cells. As above, two CD34+ cell lots derived from healthy human donors were used (PB-MR-003 and PB-MR-004). In this experiment, an approximate 3-4 fold elevation of fetal globin protein percentages to levels of about 15&%-20% was observed in erythroid progeny of HSPCs upon 63014/65722-mediated disruption of the BCL11A enhancer in both donor lots.

Reverse phase HPLC of protein samples isolated at day 21, the end point of the erythroid differentiation, was used to determine whether ZFN mediated modification of the BCL11A erythroid enhancer elevates fetal hemoglobin at the protein level. The Gamma globin (sum of the Agamma and Ggamma peaks) to alpha globin ratios were determined, as well as the Gamma globin (sum of the Agamma and Ggamma peaks)/over beta-like globin ratios (sum of the Agamma, Ggamma, beta and delta-globin peaks) and are shown in FIG. 6.

In this experiment an approximate 3-4 fold elevation of fetal globin protein percentages to levels of about 15%-20% was observed in erythroid progeny of HSPCs upon 63014/65722-mediated disruption of the BCL11A enhancer.

Example 6: Engraftment of Edited Cells in NSG Mice

Edited human CD34+ cells were then injected into NSG mice to assess engraftment. The extent of human chimerism (i.e. the percentage of human CD45+ cells) was measured using fluorescence activated cell sorting (FACS) in peripheral blood collected at 8, and 12, 16 and 20 weeks post transplantation, and in bone marrow collected at 12 weeks and 20 weeks. In addition, to test the level of engraftment of ZFN modified cells, the level of gene disruption at the BCL11A enhancer locus was evaluated by direct high-throughput sequencing of the ZFN target locus and compared to the levels of target gene modification measured in the input material.

HSPC from two healthy donors (termed PB-MR-003 and PB-MR-004) were mobilized with G-SCF and Plerixafor and purified as described in Yannaki et al. ((2012) *Mol Ther* 20(1):230-8. doi: 10.1038/mt.2011). Platelet depletion was performed on the leukapheresis product using the Fresenius-Kabi Lovo device before it was enriched for CD34+ cells using the Miltenyi Biotech CliniMACS Plus instrument. The purified cells were then seeded in culture for transfection.

Two days after CD34+ cell purification, the cells were electroporated using the Maxcyte instrument in the presence of either 120 μg/mL of a single mRNA encoding the parental ZFN pair, 63014/65722 or optimized amounts of two separate mRNAs encoding the optimized ZFN pair 80 μg/mL 63014 and 20 μg/mL 65722. Before transfection, an aliquot of the cells were set aside as the untransfected control. 95 million cells were transfected from PB-MR-003 and 120 million cells were transfected from PB-MR-004.

Following electroporation, a transient overnight culture at 30° C. was performed and cells were then cultured for an additional 24 hours at 37° C. Two days post-electroporation, cells aliquots for DNA analysis were taken and the remaining cells were harvested, cryopreserved, and stored in liquid nitrogen.

Conditioning: Mice were treated with 10 mg/kg/day Baytril water 1-2 days prior to irradiation and sublethally irradiated with 300 RAD 16-24 hours before transplantation. Transplantation was performed via tail vein injection (see below). Then mice received fresh Baytril water. Baytril water was replace one week later and Baytril water addition was discontinued 14 days after transplantation.

Transplantation: On the day of transplantation, prewarm X-Vivo 10/1% PSG+3 cytokine cocktail (Recombinant Human Stem Cell Factor (SCF), Recombinant Human Thrombopoietin (TPO), and Recombinant Human Flt-3 Ligand (Flt-3L)) at 37° C., prepare fresh PBS/0.1% BSA at ambient temperature (sterile/filtered). The cryopreserved cells were thawed at 37° C., pelleted, resuspended in prewarmed X-Vivo medium, pelleted again, resuspended in PBS/0.1% BSA and counted. After another pelleting the cell pellet was resuspended in 550 μL per mouse of PBS/0.1% BSA (2×10^6 cells/mL based off the cell count). Cells were then injected at room temperature into mouse tail vein with a 25 gauge needle. Study groups are shown below in Table 5.

TABLE 5

Dosing groups for Engraftment of edited hCD34+ cells

| | | | | | Sex, Age, Number: 60 Female NSG Mice | | |
|---|---|---|---|---|---|---|---|
| | | Species: Mouse | | Viability | | | |
| | | | % | 1 d | Dose | N/Sacrifice | |
| Group No. | N/ Group | Test Article | indels (Day 2) | Post- Thaw | (cells/ mouse) | Week 12 | Week 20 |
| 1 | 10 (M1-10) | PB-MR-003 donor cells, treated with 63014 and 65722 mRNA. | 79% | 83% | 1 million | 5 | 5 |
| 3 | 10 (M21-30) | PB-MR- 003.untransfected | 0.1% | 95% | 1 million | 5 | 5 |
| 4 | 10 (M31-40) | PB-MR-004 donor cells treated with 63014 and 65722 mRNA. | 75% | 77% | 1 million | 5 | 5 |
| 6 | 10 (M51-60) | PB-MR- 004.untransfected | 0.1% | 92% | 1 million | 5 | 5 |

Animals were observed daily for general health and weighed daily for the first 2 weeks and weighed bi-weekly thereafter. Peripheral blood was collected from the submandibular vein (100 µL) at 8, 12, 16 and 20 weeks post transplantation or via cardiac puncture (1 mL) for the sacrificed animals at 12 and 20 weeks post-transplantation. Half of the animals in each groups (5 mice per group) were euthanized at 12 weeks post transplantation and bone marrow and terminal blood were collected for analysis. The remaining animals in each group (5 mice per group) were sacrificed at 20 weeks post transplantation.

Blood collection, cell harvest and processing: Peripheral blood was collected via the submandibular vein or cardiac puncture into EDTA tubes and centrifuged at 500×g for 5 min to remove the plasma. Following phosphate-buffered saline (PBS) bovine serum albumin (BSA) wash and centrifugation, a 10× volume of hemolytic buffer was added to the pellet, and the mixture was incubated at 37° C. for 15 min, centrifuged and washed again. The pelleted fraction was reconstituted in 1 mL PBS BSA; an aliquot was removed and centrifuged at 1,000×g for 5 min, with the resultant pellet preserved for genotyping. The supernatant fraction was utilized for FACS analyses.

Bone marrow, femur, tibia and pelvic bones were collected in Iscove's Modified Dulbecco's Medium (IMDM) containing fetal calf serum (FCS); total bone marrow was flushed into a PBS BSA solution and filtered using a 70 µm nylon strainer. Volume was adjusted to 10 mL with PBS BSA, and an aliquot was used for cell counting (Cellometer).

ZFN activity was analyzed using MiSeq deep sequencing. In brief, Genomic DNA from mice injected with either untransfected control CD34+ HSPC or CD34+ HSPC transfected with enhancer targeting ZFN mRNA was isolated from blood samples obtained at 8 week and 12 week or from bone marrow at 12 weeks post-injection. The region of interest (containing the ZFN binding site within the BCL11A locus) was PCR amplified and the level of modification was determined by paired end deep sequencing on the Illumina platform (MiSeq).

To generate libraries compatible with the Illumina MiSeq sequencing platform, adaptors, barcodes, and flow cell binder (short DNA sequence) were attached to the target specific amplicons using two sets of fusion primers in sequential PCRs. For MiSeq evaluations of human BCL11A enhancer modification in the mouse blood and bone marrow samples, the protocol had to be adjusted due to the low target DNA amounts in these samples.

The following primers were used for the MiSeq Adaptor PCR:

PRJIYLFN-f2:
(SEQ ID NO: 32)
ACA CGA CGC TCT TCC GAT CTN NNN AGT CCT CTT CTA
CCC CAC CCA
and PRJIYLFN-r4:
(SEQ ID NO: 33)
GAC GTG TGC TCT TCC GAT CTC TAC TCT TAG ACA TAA
CAC ACC AGG G.

For the analysis, DNA from mouse bone marrow samples was isolated by DNeasy and approximately 100 ng of DNA were used in each PCR reaction. DNA from mouse blood samples was isolated by Tissue XS and 10 µL of the 15 µL isolated DNA was used in each reaction. In addition to the DNA, the following were added to each MiSeq PCR reaction: 25 µL HotStar Taq mix (Qiagen), 0.5 µL each of the BCL11A enhancer primers listed above (at a concentration of 100 nM), and water to a 50 µL total reaction volume. Typical MiSeq PCR conditions were: 95° C. denaturation for 15', and 30 cycles at 94° C. for 30", 62° C. for 30" and 72° C. for 40", followed by a 10' elongation at 72° C. After the MiSeq PCR, the PCR product was diluted between 1:50 and 1:200 with water, or left undiluted for samples with very low starting cell numbers. Barcode PCR was performed with 1 µL of the MiSeq PCR product diluted as described above, 25 µL HotStar Taq mix, 1 µL forward barcode primer, 1 µL reverse barcode primer (both at a concentration of 10 nM) and water to a 50 µL total reaction volume. Barcode PCR conditions were: 95C denaturation for 15', and 18 cycles at 94° C. for 30", 60° C. for 30" and 72° C. for 30", followed by a 10' elongation at 72° C. Barcode PCR products were pooled and sequenced on the Illumina MiSeq sequencer. The results are shown in Table 5 above.

FACS analysis for chimerism, and cell lineage determination. To assess the degree of human chimerism, the fraction of cells in the peripheral blood (at 8, 12, 16 and 20 weeks post engraftment) and bone marrow (at 12 and 20 weeks post engraftment) were stained with hCD45-APC Cy7 (Biolegend) and hCD45-BV510 (BD Biosciences) antibodies respectively and FACS analysis was performed In addition, hematopoietic lineages analysis was performed by staining bone marrow cells with the specific antibodies described in Table 6 below:

TABLE 6

Antibody sources for cell markers

| | |
|---|---|
| CD3-FITC: BD 561807 (clone UCHT1) | BD 561807 |
| CD19-PE: BD 340364 (clone SJ25C1) | BD 340364 |
| CD45-BV510 | BD 363204 |
| Lin-APC (CD3/UCHT1, CD14/HCD14, CD16/3G8, CD19/HIB19, CD20/2H7, CD56/HCD56) | BIOLEGEND 348803 |
| CD33-PE-CF594 | BD 562492 |
| GlyA-FITC | DAKO 0870 |
| CD38-PerCP Cy5.5 | BD 551400 |
| CD14-PE | BD 555398 |
| CD34-PE Cy7 | BD 560710 |
| CD71-APC Cy7/H7 | BD 563671 |
| CD15-BV650 | BD 554232 |
| CD8-PerCP Cy5.5 | BD 341051 |
| CD4-PE Cy7 | BD 344512 |
| CD56-APC | BD 318310 |
| IgM-APC Cy7 | BD 314520 |
| CD20-BV650 | BD 563780 |

In addition, to purify and sort the HSPC populations, we used an enrichment/depletion strategy using magnetic cell separation (MACS). Bone marrow cells were first stained with CD19-biotin, CD3-biotin, B220-biotin, TERI 19-biotin and m-ckit-biotin (BD Biosciences) and then incubated with anti-biotin beads (Miltenyi Biotec). The positive fraction and depleted fraction were separated using LS columns (Miltenyi Biotec) placed in the magnetic field of a MACS. After separation, the positive fraction was stained with Streptavidin-APC, CD3-FITC, CD19-PE, CD45-BV510 (BD Biosciences) and the depleted fraction with CD34-FITC (BD Biosciences), Gly-A-PE (DAKO), CD19-APC (BD), Lin-APC (Biolegend), Streptavidin-APC, CD45-BV510, CD33-PE-CF594 (BD) and CD38-PECy-7 (Biolegend).

Untransfected HSPC and 63014/65722-transfected HSPC were engrafted into NSG mice using standard procedures as described above. The degree of human chimerism in these mice following engraftment was assessed by measuring the fraction of hCD45 positive cells using FACS.

Figure 7:
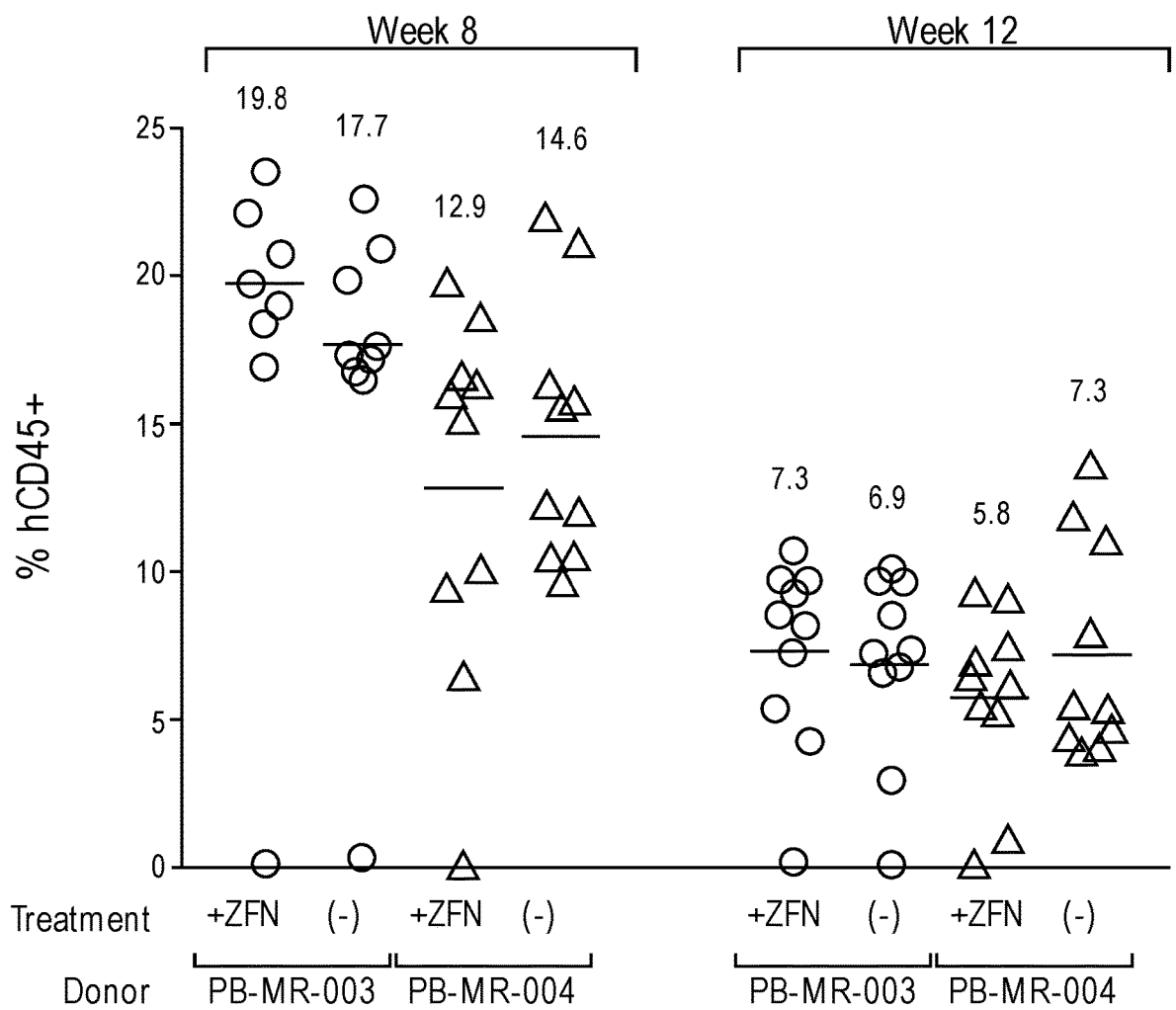
FIG. 7 is a graph indicating relative human chimerism in mice engrafted with 63014/65722 treated donor lots ("+ZFN") as described above. Human chimerism was measured through the detection of cells bearing a hCD45 marker on their surface using FACS. Percentages of human hCD45+ cells in the peripheral blood collected at either 8 or 12 weeks post-transplant are indicated. The data showed good engraftment levels in this study with comparable human chimerism following engraftment of untransfected control ("(−)") and ZFN transfected HSPC ("+ZFN"). Open circles and triangles represent individual animals.
Figure 8:
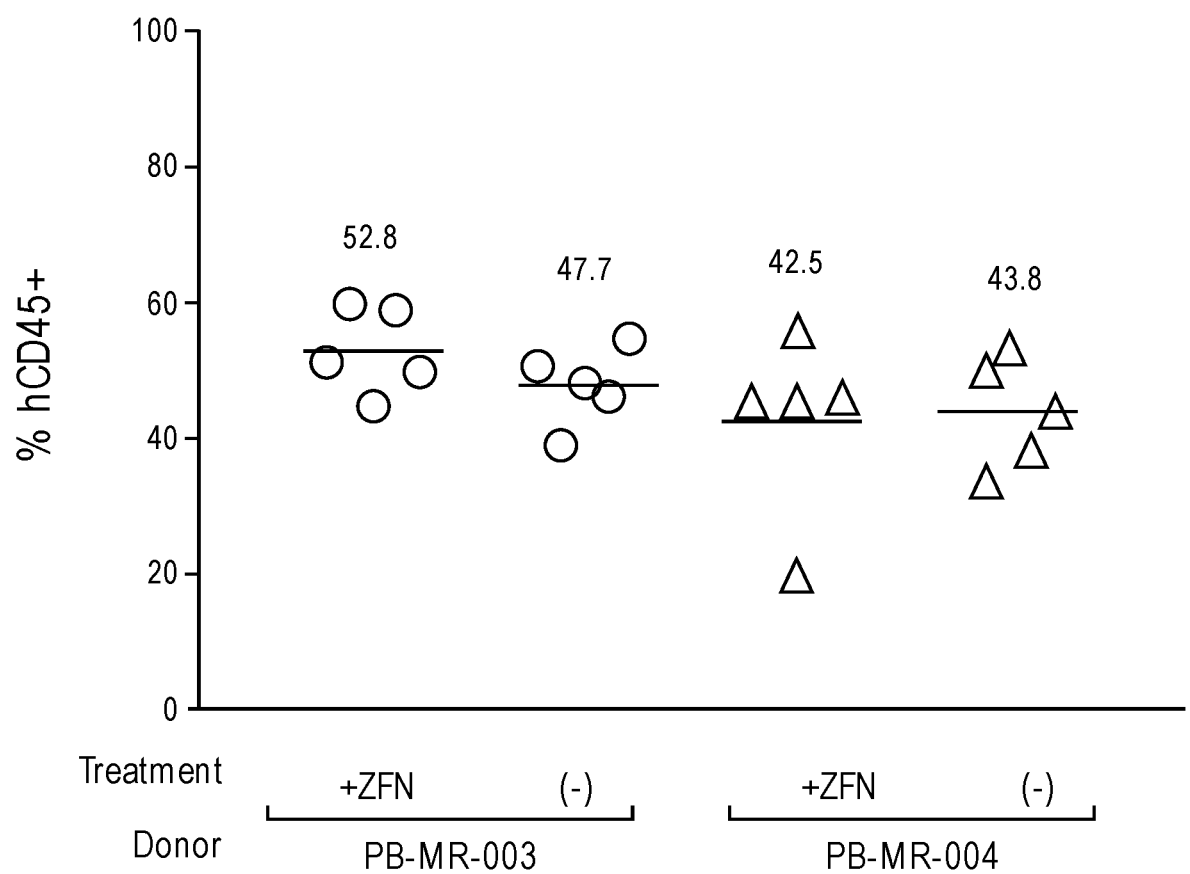
FIG. 8 shows the percentage of chimerism detected in the bone marrow of the engrafted mice where human cells were identified by the presence of hCD45 on their cell surfaces. Samples were analyzed at 12 weeks post-engraftment.
Figure 9A:
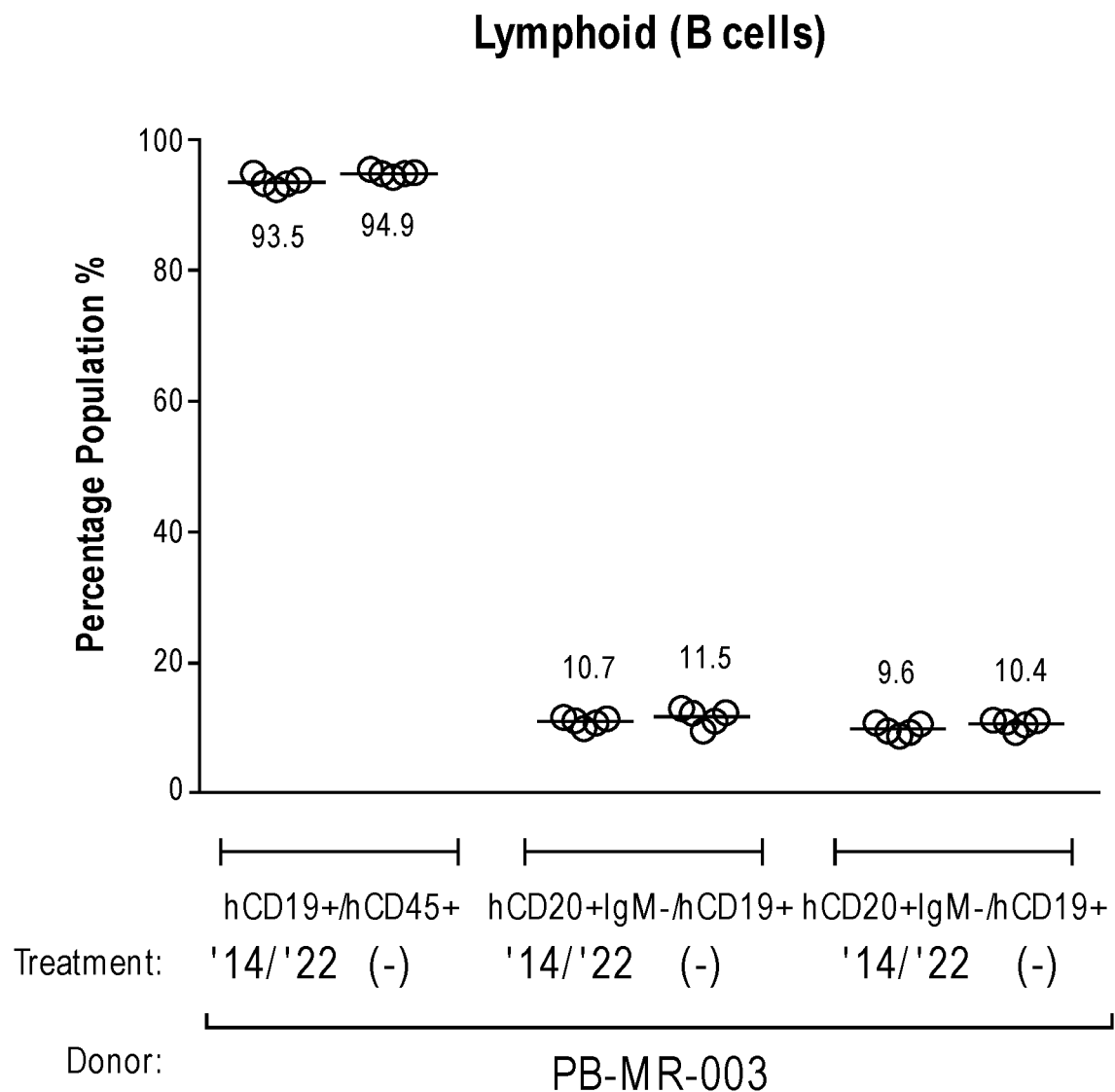
FIGS. 9A through 9D are graphs depicting the reconstitution of various hematopoietic cell lineages tested by FACS analysis of bone marrow cells in engrafted mice obtained at week 12 with antibodies recognizing lineage specific cell surface markers. The data showed comparable representation of all analyzed human hematopoietic lineages in the bone marrow at week 12 post-injection between the BCL11A-specific ZFN mRNA treated CD34+ cell progeny ("14/'22") and that of the untransfected cells ("(−)"). Shown are data from lymphoid, myeloid, erythroid and HSPC (FIGS. 9A through 9D, respectively) for cells derived from both donors ("003" and "004"). The data showed comparable representation of all analyzed human hematopoietic lineages in the bone marrow at week 12 post-injection between the Bell 1A ZFN mRNA treated CD34+ cell progeny and that of the untransfected cells.
Figure 9B:
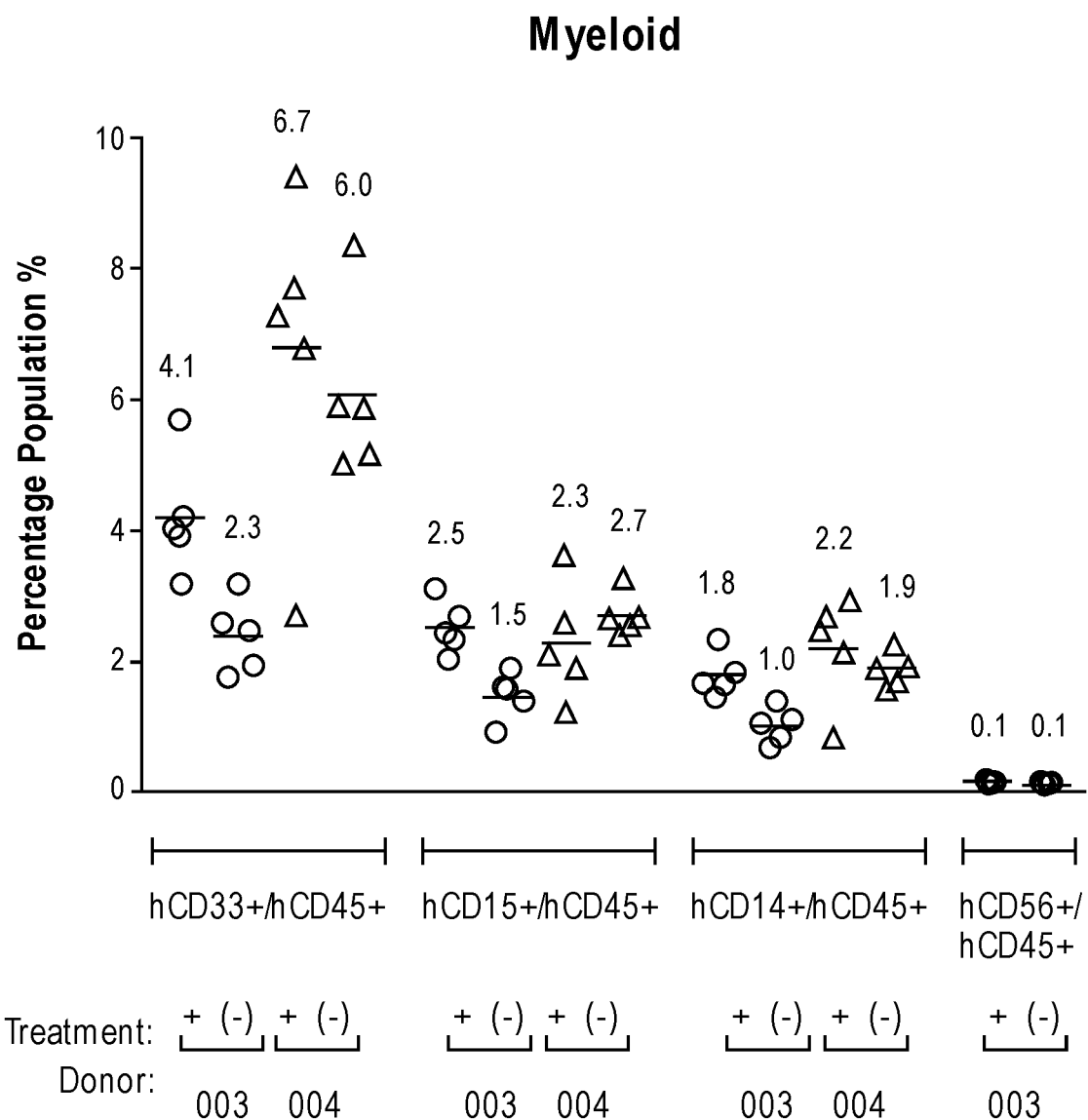
Figure 9C:
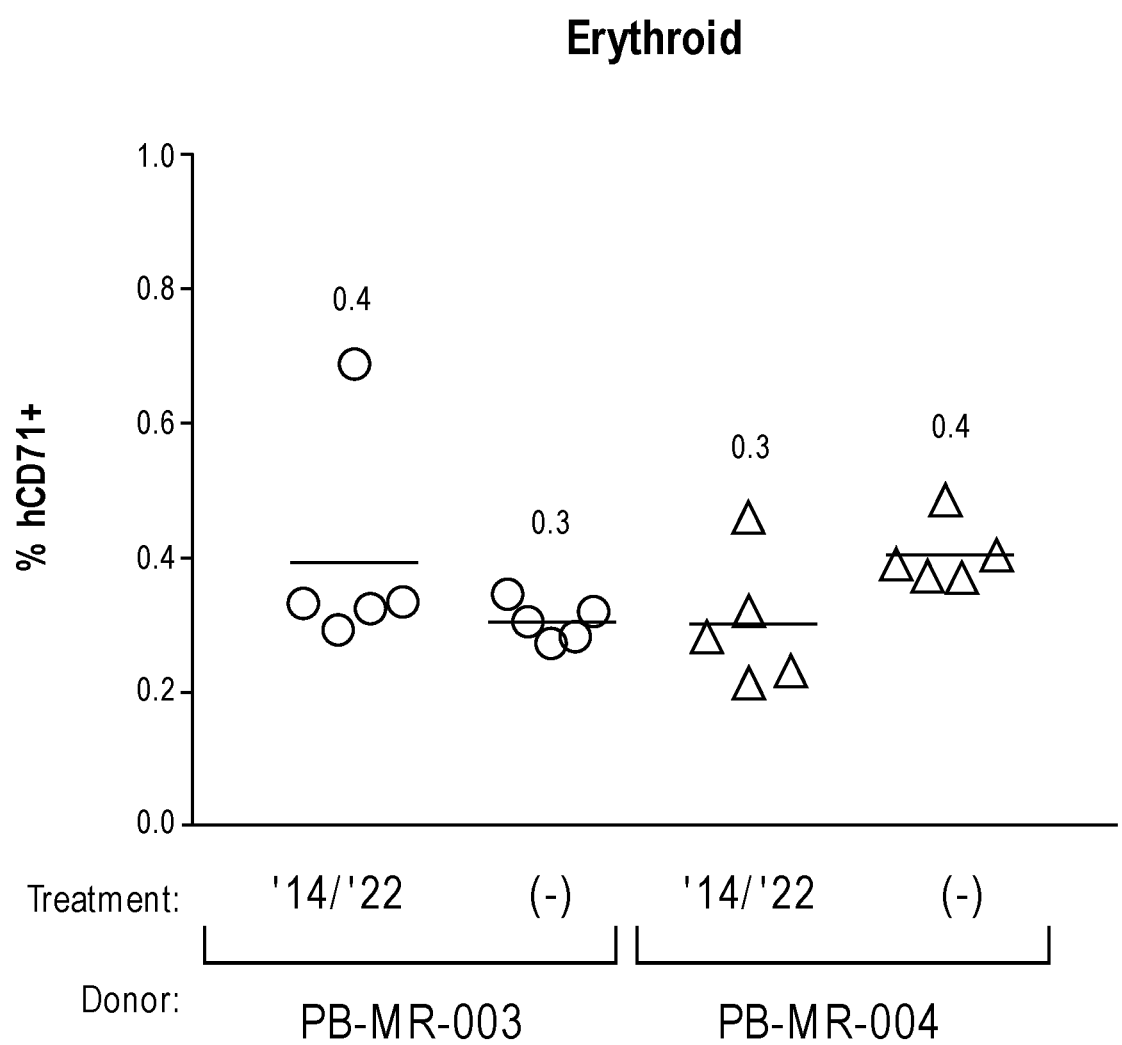
Figure 9D:
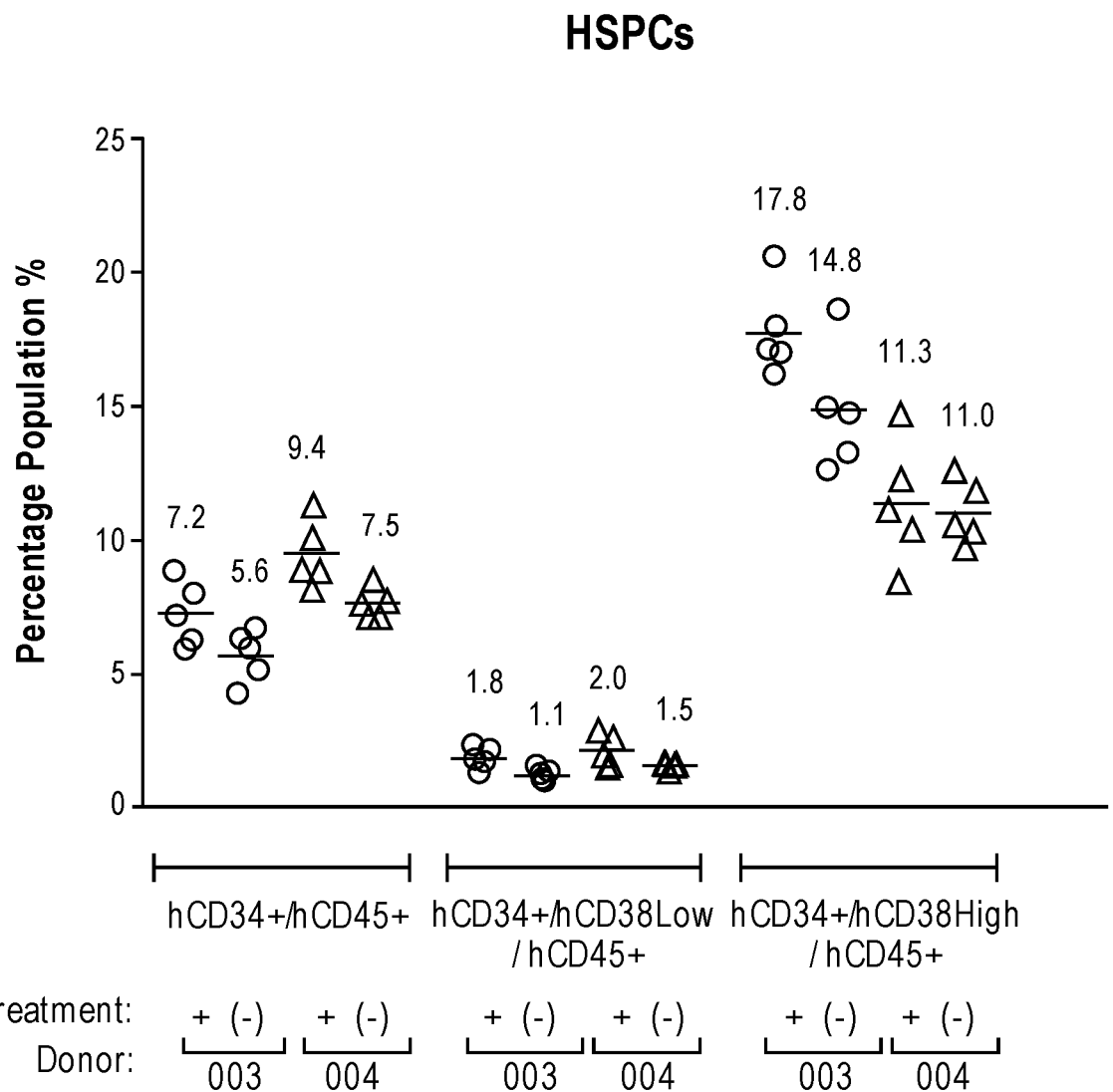

FIG. 7 shows the percentages of human CD45+ cells in peripheral blood collected at 8, and 12 weeks post-transplant and FIG. 8 shows percentages in bone marrow harvested at Week 12. As shown, engraftment levels in this study were comparable human chimerism following engraftment of untransfected control and 63014/65722 transfected HSPC. Only 3 mice out of 60 distributed through the groups did not have CD45+ cells indicating a failure to engraft.

Reconstitution of various hematopoietic cell lineages was tested by FACS analysis of bone marrow cells obtained at week 12 with antibodies recognizing lineage specific cell surface markers using standard procedures. As shown in FIG. 9, comparable representation of all analyzed human hematopoietic lineages in the bone marrow at week 12 post-injection between the BCL11A specific ZFN encoding mRNA treated CD34+ cell progeny and that of the untransfected cells was observed. Bone marrow of the mice sacrificed at Week 12 post-engraftment was isolated and the distribution of various hematopoietic lineages was analyzed by FACS using antibodies recognizing the indicated lineage markers. All numbers are given as the ratio of the cells staining positive for the indicated lineage marker versus the percentage of human CD45 positive cells, except for the cells expressing the erythroid marker Cd71+(Ter119) in FIG. 9C, which are given as the percentage of positively staining cells in the entire population since erythroid cells are not CD45 positive.

Figure 10:
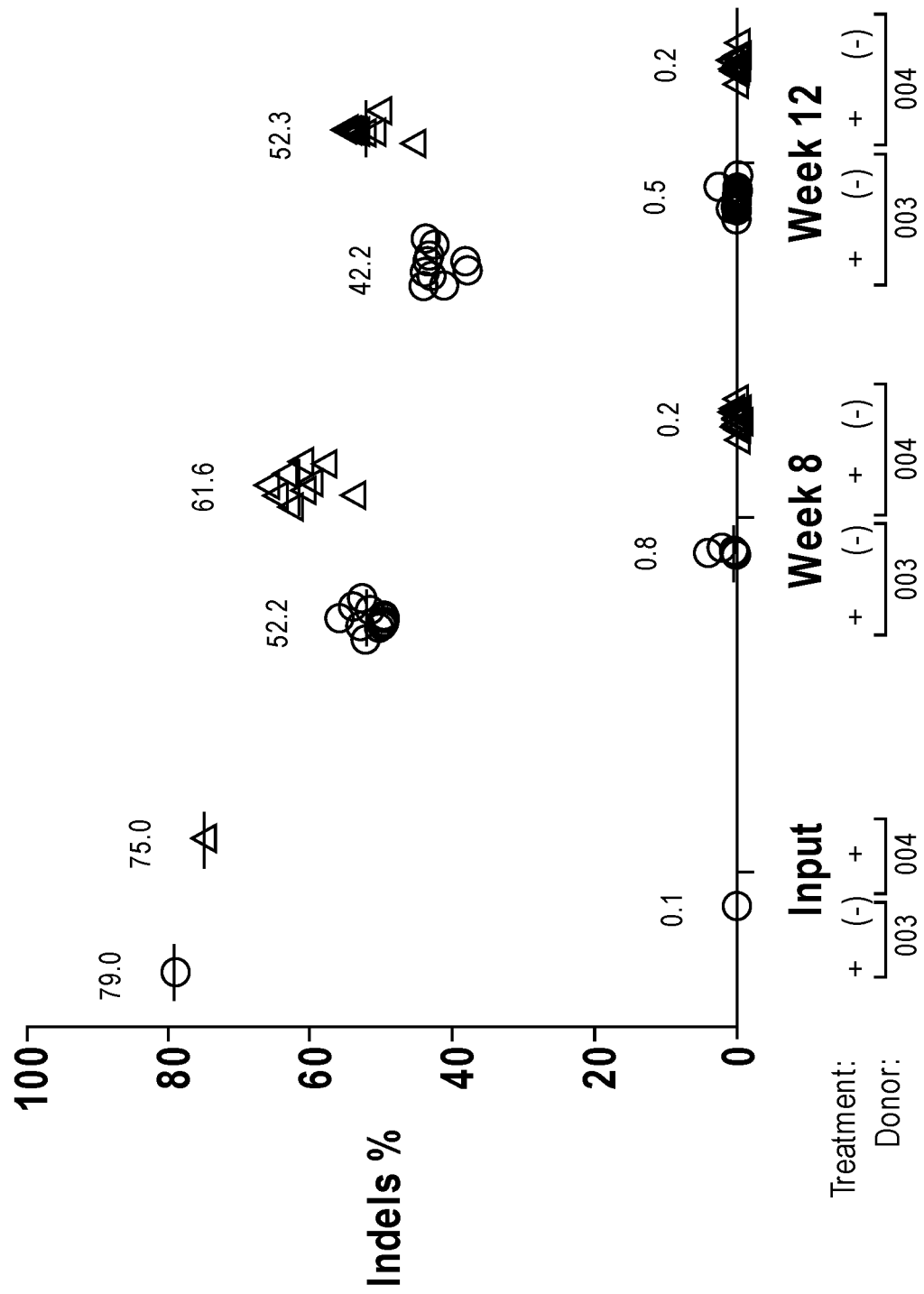
FIG. 10 is a graph depicting the level of gene modification at the BCL11A target in DNA isolated from the peripheral blood of engrafted mice, assayed by deep sequencing. Data are shown for the input cells (2 days after ZFN transfection, ("+")), and then for blood cells 8 or 12 weeks following engraftment, and demonstrated a good retention of gene modification. Untransfected cells are represented by "(−)" in the Treatment line.
Figure 11:
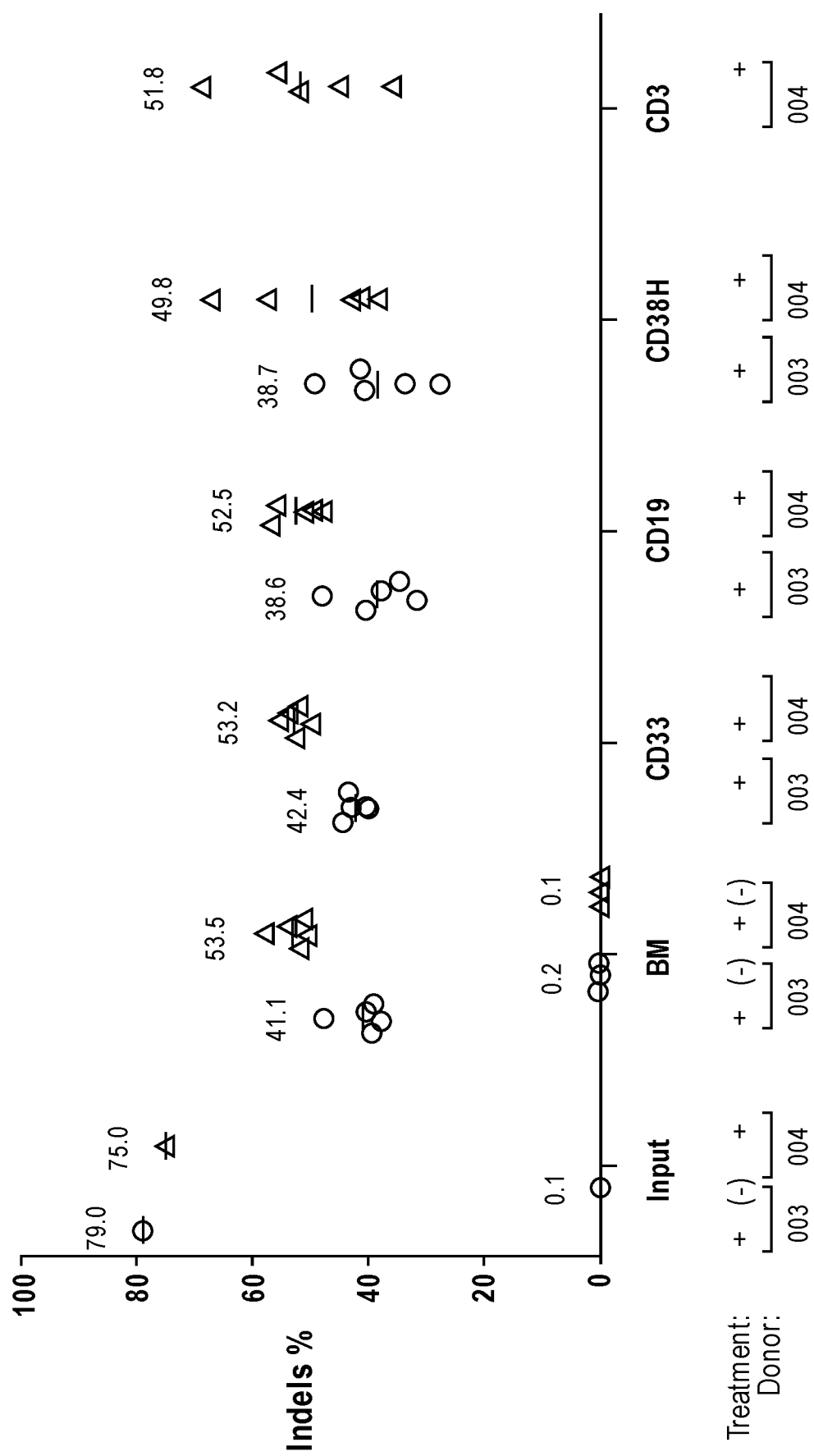
FIG. 11 is a graph depicting the amount of gene modification at the BCL11A target for bone marrow cell samples following engraftment of the ZFN-treated cells ("+"). Untreated cells are represented by "(−)" in the Treatment line. Comparable modification was observed in both BCL11A dependent lineages (B cells, expressing the CD19 marker, primitive progenitors, expressing CD45 and high levels of CD38) and BCL11A independent (myeloid) lineages. Although the input gene modification levels were higher in the PB-MR-003 donor sample than in the PB-MR-004 donor sample, the PB-MR-004 derived cells consistently showed higher modification levels, i.e. better retention of modification, in mice than those derived from PB-MR-003.

The levels of gene modification at the BCL11A erythroid enhancer (% of alleles with insertions and deletions [indels]) were assessed by deep sequencing of the ZFN target region using the MiSeq sequencing platform as described above. The data are shown in FIG. 10 for blood samples from week 8 and week 12, and in FIG. 11 for bone marrow samples from week 12 and sorted lineages derived from the week 12 bone marrow cell samples of the 63014/65722 treated cells. For comparison, the indel percentages measured 2 days after the transfection (as listed in Table 5) are also shown on the graphs of FIGS. 10 and 11.

In addition, good retention of gene modification at the BCL11A erythroid enhancer was found for both 63014/65722-treated HSPC donor sets at the various time points and in the various lineages. Comparable modification was observed in both BCL11A dependent (B cells, 'CD19'; primitive progenitors, 'CD38H') and BCL11A independent (myeloid 'CD33') lineages. Although the input gene modification levels were higher in the PB-MR-003 donor sample than in the PB-MR-004 donor sample, the PB-MR-004 derived cells consistently show higher modification levels, i.e. better retention of modification, in mice than those derived from PB-MR-003.

Overall, the observed retention of gene modification at the BCL11A erythroid enhancer in mice was consistent with that observed in prior mouse experiments using a number of ZFNs targeting a variety of gene targets.

Furthermore, as human erythroid progenitors are not able to differentiate in mice, to determine the amount of BCL11A targeted gene modification that occurred in these cells, bone marrow cells were removed from the mice and differentiated in vitro. In these experiments, bone marrow derived human cells were removed from sacrificed mice at week 12 following engraftment and differentiated in vitro as described above. BCL11A target gene modification was measured by high-throughput Miseq sequencing of DNA isolated from cells at day 14 of the differentiation.

Figure 12:
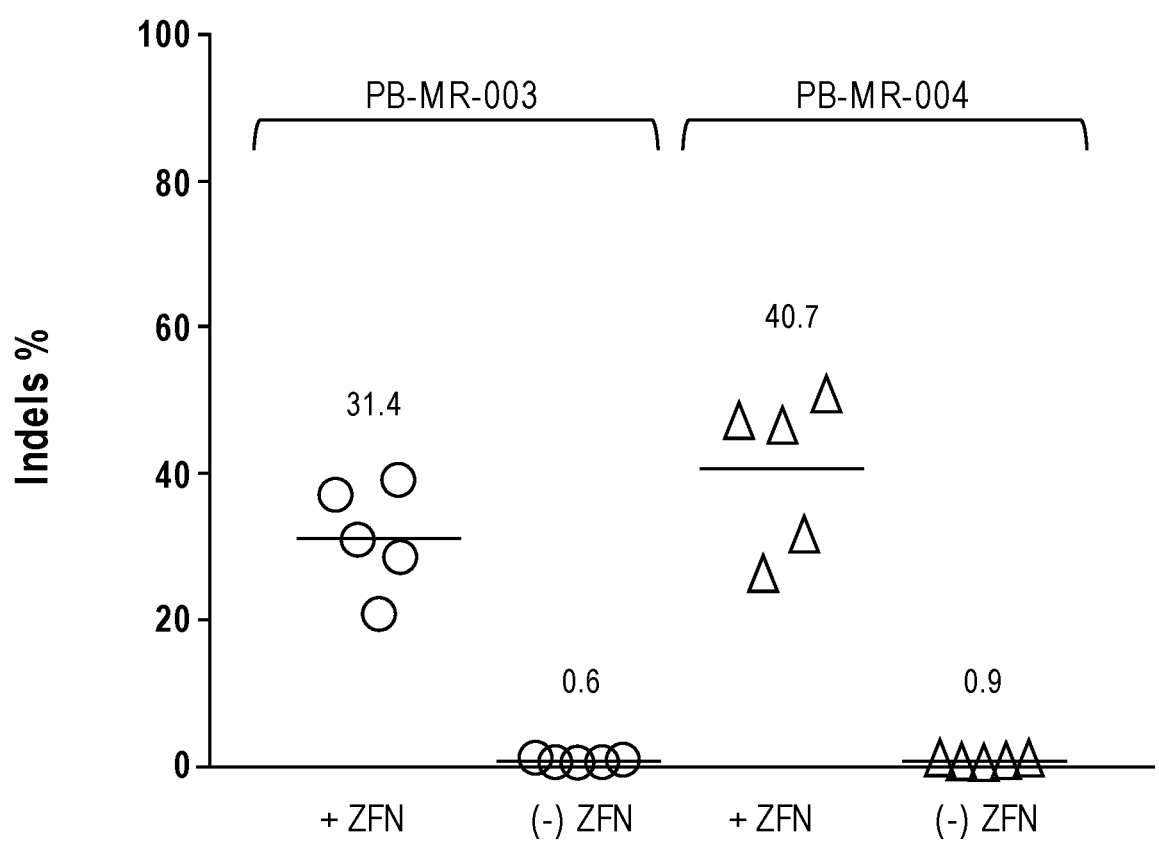
FIG. 12 is a graph depicting the amount of gene modification in erythroid cells derived from week 12 bone marrow cells following in vitro differentiation for 14 days. The data were from mice originally engrafted with the two different donors described above, and demonstrated that the BCL11A modification mediated by ZFN treatment ("+ ZFN") is not markedly altered during the erythroid differentiation. Cells that were not treated with ZFN are indicated by "(−) ZFN".

Modification data (indels) are presented in FIG. 12, which shows the modification levels at day 14 of the erythroid differentiation. Indel percentages at day 14 of the in vitro differentiation vary markedly for each culture that was generated from cells isolated from one mouse, reflecting the oligocellular nature of the expansion obtained under these conditions. The data indicate that BCL11A enhancer modification mediated by the 63014/65722 ZFNs was not markedly altered during the erythroid differentiation. As was observed in the blood and bone marrow samples, erythroid progeny samples of PB-MR-004 derived cells showed higher average levels of modification than erythroid progeny of PB-MR-003 derived cells.

Figure 13A:
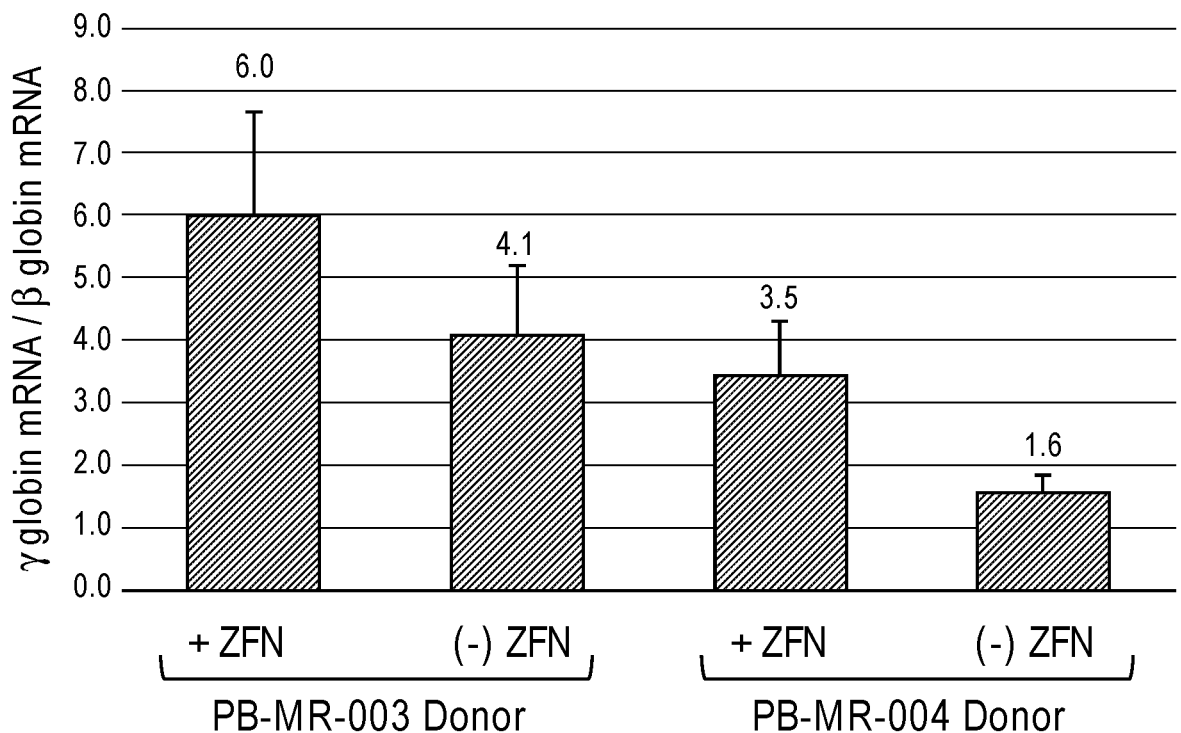
FIGS. 13A and 13B are graphs depicting the relative amount of γ-globin encoding mRNA, where the concentration of γ-globin mRNA is depicted either as a ratio of γ globin/β globin mRNA (FIG. 9A) or as a ratio of γ globin/α globin mRNA (FIG. 9B). Both in the untransfected ("(−) ZFN") and the ZFN treated samples ("+ ZFN") γ-globin to β globin or γ-globin to α-globin mRNA ratios differed widely between the erythroid progenies of individual mice from the same group. However, despite this variability and the variability introduced by the use of two different human donors, the 63014/65722 treated sample averages show an ~1.5-2 fold increase in γ globin mRNA levels compared to their respective untransfected counterparts.
Figure 13B:
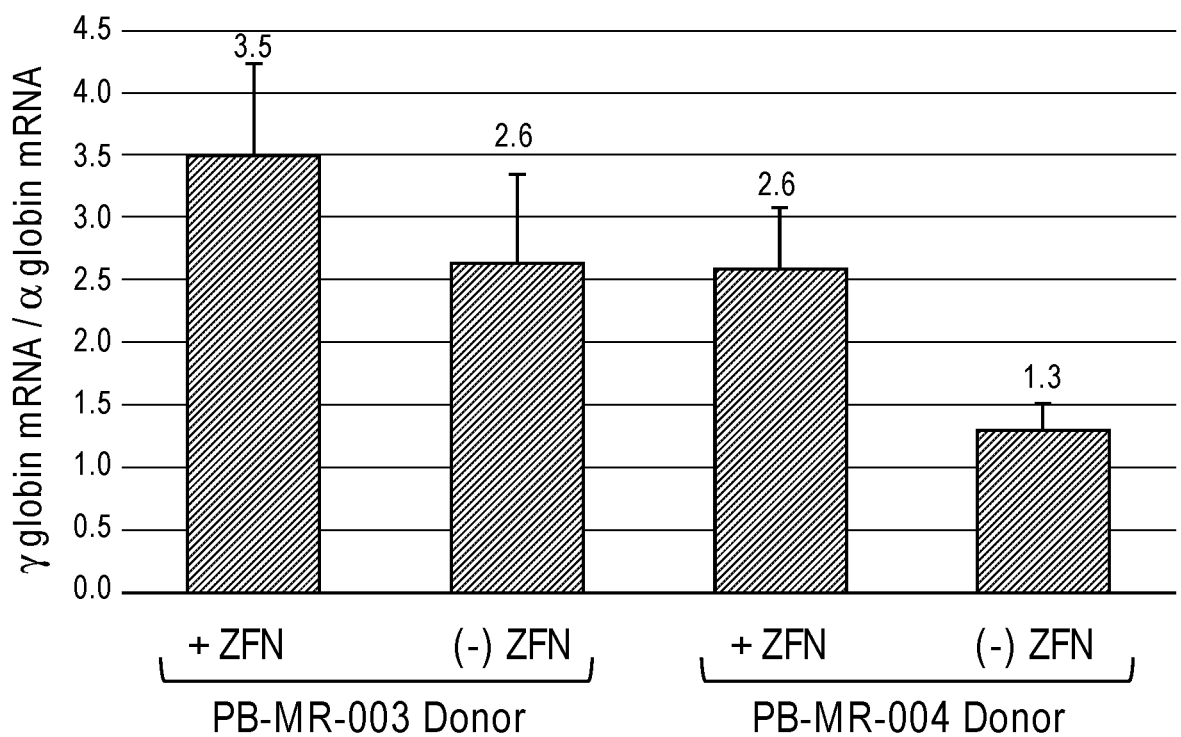

The relative levels of various globin mRNAs were determined by RT-PCR analysis of RNA isolated from cells at day 14 of the in vitro erythroid differentiation, and the data is presented in FIG. 13A where the relative γ-globin to β globin mRNA and γ-globin to α-globin mRNA ratios (FIG. 13B) averaged out for the 5 erythroid cultures from each group. Both in the untransfected and the 63014/65722 treated samples γ-globin to 3 globin or γ-globin to a globin mRNA ratios differ widely between the erythroid progenies of individual mice from the same group. The donor PB-MR-004 derived cultures show on average lower γ-globin ratios than those from donor PB-MR-003, in line with the better maturation observed for PB-MR-004 derived samples. However in spite of this variability, the ZFN treated sample averages show an ~1.5-2 fold increase in γ globin mRNA levels compared to their respective untransfected counterparts.

Figure 14:
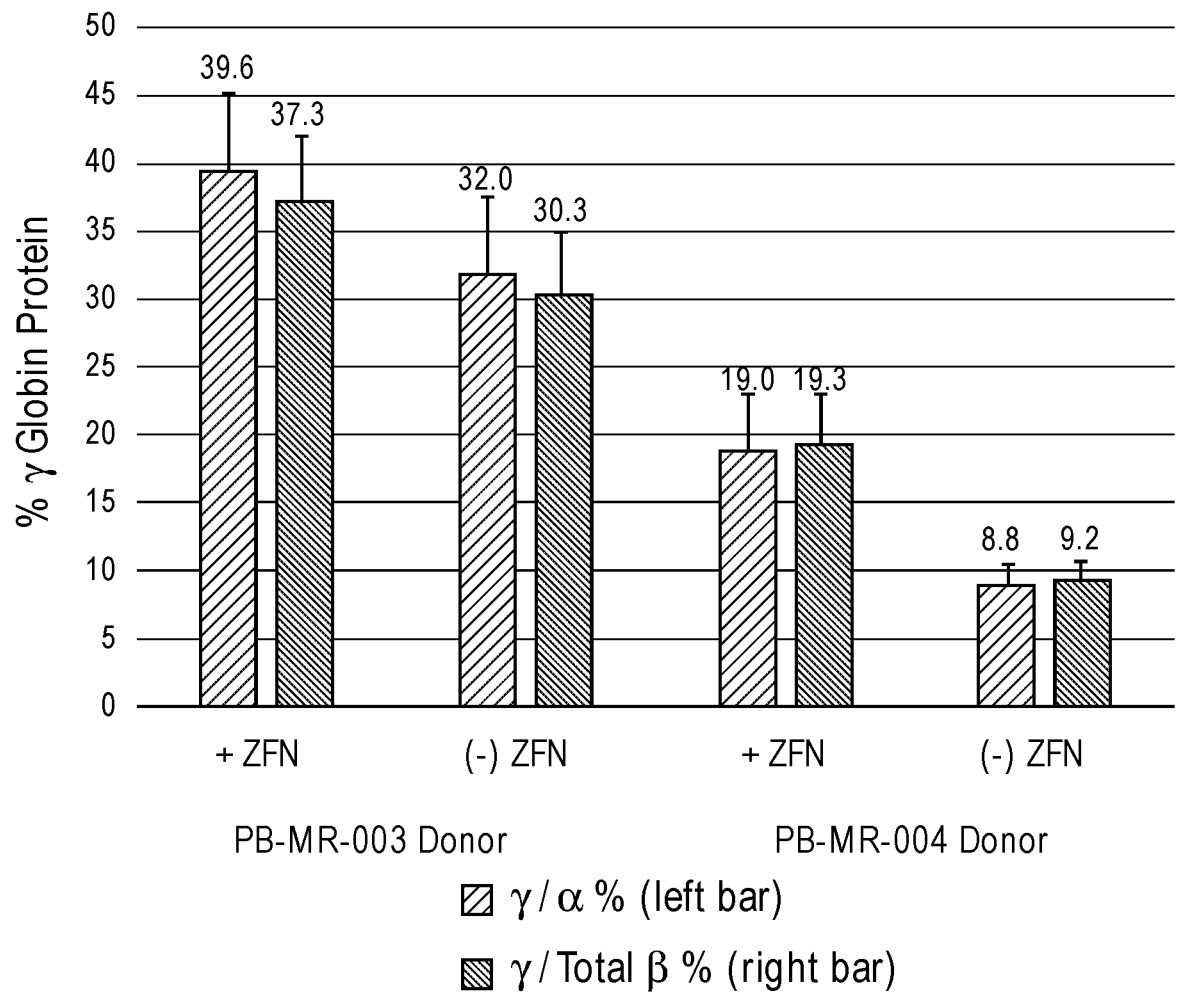
FIG. 14 is a graph depicting the difference in the amount of γ-globin protein (expressed as either a ratio of γ-globin/α-globin or γ-globin/total β-like protein) in bone marrow derived cells from engrafted mice where the bone marrow cells were submitted to an in vitro differentiation protocol. Protein levels were measured 16 days into differentiation. The Gamma (γ) globin (sum of the Agamma and Ggamma peaks) to alpha (α) globin ratios were determined, as well as the Gamma globin (sum of the Agamma and Ggamma peaks)/over beta-like globin ratios (sum of the Agamma, Ggamma, beta and delta-globin peaks). In line with the poor erythroid differentiation of the PB-MR-003 derived samples the gamma-globin levels in the untransfected cells derived from this donor were very high (~30%), and therefore ZFN treatment ("+ ZFN") resulted in only a 1.2-fold increase in gamma-globin levels as compared with untreated cells ("(−) ZFN"). The PB-MR-004 showed more typical untransfected levels (~9%) and exhibited an ~2-fold increase in gamma-globin protein levels after 12 weeks passage through the mouse.

Globin protein levels were assessed by HPLC analysis. FIG. 14 shows globin protein analyses of samples harvested at day 16 of the differentiation. The Gamma globin (sum of the Agamma and Ggamma peaks) to alpha globin ratios were determined, as well as the Gamma globin (sum of the Agamma and Ggamma peaks)/over beta-like globin ratios (sum of the Agamma, Ggamma, beta and delta-globin peaks) and the averages for each group are shown above each bar. In line with the poor erythroid differentiation of the PB-MR-003 derived samples the gamma-globin levels in the untransfected cells derived from this donor were very high (~30%), and therefore ZFN treatment resulted in only a 1.2 fold increase in gamma-globin levels. The PB-MR-004 showed more typical untransfected levels (~9%) and exhibited an ~2-fold increase in gamma-globin protein levels after 12 weeks passage through the mouse.

It is thought patients that have a >8.6% of γ globin naturally are at an advantage as compared to patients with γ globin levels <8.6% (Platt et al. (1994) *N Engl J Med,* 330:1639-44). In fact, achieving a chimeric 10-20% percentage of non-sickle cell RBCs through engraftment of edited cells may lead to clinical improvement (Chang et al. (2017) *Mol Ther Methods Clin Dev* 4:137-148. doi 10.1016/j.omtm.2016.12.009). Thus, despite having to go through an in vitro erythroid differentiation process, the percentage of chimeric cells, and the level of γ-globin protein being detected are indicative of therapeutic efficacy.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A genetically modified cell comprising a genomic modification in the BCL11A locus and further comprising a zinc finger nuclease (ZFN) comprising left and right ZFNs, the left ZFN comprising the amino acid sequence of SEQ ID NO:29 and the right ZFN comprising the amino acid sequence of SEQ ID NO:31.

2. The cell of claim 1, further comprising a polynucleotide according to SEQ ID NO:28 for encoding the left ZFN and a polynucleotide according to SEQ ID NO:30 for encoding the right ZFN.

3. The cell of claim 1, wherein the cell is a CD34+ hematopoietic stem cell.

4. The cell of claim 1, wherein the cell is a human cell.

5. A pharmaceutical composition comprising the cells of claim 1.

6. A method of increasing globin production in a subject, the method comprising:
   administering the pharmaceutical composition of claim 5 to the subject.

7. The method of claim 6, wherein the subject is a human patient and the cells are human stem cells and/or human precursor cells.

8. The method of claim 7, wherein the cells are infused into the patient and the cells engraft, differentiate and mature in the subject.

9. The method of claim 6, wherein the subject has a hemoglobinopathy.

10. The method of claim 6, wherein the hemoglobinopathy is a beta-thalassemia or sickle cell disease.

11. A kit comprising the pharmaceutical composition of claim 5.

* * * * *

SEQUENCE LISTING

```
<160> NUMBER OF SEQ ID NOS: 34

<210> SEQ ID NO 1
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
aaagcaactg ttagcttgca ctagacta                                            28

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
cacaggctcc aggaagggtt tggcctct                                            28

<210> SEQ ID NO 3
<211> LENGTH: 407
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: NON_CONS
<222> LOCATION: (214)..(215)
<223> OTHER INFORMATION: Residues at these positions are separated by
      any linker sequence known in the art

<400> SEQUENCE: 3

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Ile His Gly Val Pro Ala Ala Met Ala Glu Arg Pro Phe Gln Cys
```

```
                35                  40                  45
Arg Ile Cys Met Gln Asn Phe Ser Asp Gln Ser Asn Leu Arg Ala His
 50                  55                  60

Ile Arg Thr His Thr Gly Glu Lys Pro Phe Ala Cys Asp Ile Cys Gly
 65                  70                  75                  80

Arg Lys Phe Ala Arg Asn Phe Ser Leu Thr Met His Thr Lys Ile His
                 85                  90                  95

Thr Gly Ser Gln Lys Pro Phe Gln Cys Arg Ile Cys Met Gln Asn Phe
                100                 105                 110

Ser Ser Thr Gly Asn Leu Thr Asn His Ile Arg Thr His Thr Gly Glu
                115                 120                 125

Lys Pro Phe Ala Cys Asp Ile Cys Gly Arg Lys Phe Ala Thr Ser Gly
                130                 135                 140

Ser Leu Thr Arg His Thr Lys Ile His Thr His Pro Arg Ala Pro Ile
145                 150                 155                 160

Pro Lys Pro Phe Gln Cys Arg Ile Cys Met Gln Asn Phe Ser Asp Gln
                165                 170                 175

Ser Asn Leu Arg Ala His Ile Arg Thr His Thr Gly Glu Lys Pro Phe
                180                 185                 190

Ala Cys Asp Ile Cys Gly Arg Lys Phe Ala Ala Gln Cys Cys Leu Phe
                195                 200                 205

His His Thr Lys Ile His Glu Leu Glu Glu Lys Lys Ser Glu Leu Arg
210                 215                 220

His Lys Leu Lys Tyr Val Pro His Glu Tyr Ile Glu Leu Ile Glu Ile
225                 230                 235                 240

Ala Arg Asn Ser Thr Gln Asp Arg Ile Leu Glu Met Lys Val Met Glu
                245                 250                 255

Phe Phe Met Lys Val Tyr Gly Tyr Arg Gly Lys His Leu Gly Gly Ser
                260                 265                 270

Arg Lys Pro Asp Gly Ala Ile Tyr Thr Val Gly Ser Pro Ile Asp Tyr
                275                 280                 285

Gly Val Ile Val Asp Thr Lys Ala Tyr Ser Gly Gly Tyr Asn Leu Pro
290                 295                 300

Ile Gly Gln Ala Asp Glu Met Glu Arg Tyr Val Glu Glu Asn Gln Thr
305                 310                 315                 320

Arg Asp Lys His Leu Asn Pro Asn Glu Trp Trp Lys Val Tyr Pro Ser
                325                 330                 335

Ser Val Thr Glu Phe Lys Phe Leu Phe Val Ser Gly His Phe Lys Gly
                340                 345                 350

Asn Tyr Lys Ala Gln Leu Thr Arg Leu Asn His Ile Thr Asn Cys Asn
                355                 360                 365

Gly Ala Val Leu Ser Val Glu Glu Leu Leu Ile Gly Gly Glu Met Ile
                370                 375                 380

Lys Ala Gly Thr Leu Thr Leu Glu Glu Val Arg Arg Lys Phe Asn Asn
385                 390                 395                 400

Gly Glu Ile Asn Phe Arg Ser
                405

<210> SEQ ID NO 4
<211> LENGTH: 372
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<221> NAME/KEY: NON_CONS
<222> LOCATION: (181)..(182)
<223> OTHER INFORMATION: Residues at these positions are separated by
      any linker sequence known in the art

<400> SEQUENCE: 4
```

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Ile His Gly Val Pro Ala Ala Met Ala Glu Arg Pro Phe Gln Cys
            35                  40                  45

Arg Ile Cys Met Gln Lys Phe Ala Arg Asn Asp His Arg Thr Thr His
50                  55                  60

Thr Lys Ile His Thr Gly Glu Lys Pro Phe Gln Cys Arg Ile Cys Met
65                  70                  75                  80

Gln Asn Phe Ser Gln Lys Ala His Leu Ile Arg His Ile Arg Thr His
                85                  90                  95

Thr Gly Glu Lys Pro Phe Ala Cys Asp Ile Cys Gly Arg Lys Phe Ala
            100                 105                 110

Gln Lys Gly Thr Leu Gly Glu His Thr Lys Ile His Thr Gly Ser Gln
            115                 120                 125

Lys Pro Phe Gln Cys Arg Ile Cys Met Gln Asn Phe Ser Arg Gly Arg
        130                 135                 140

Asp Leu Ser Arg His Ile Arg Thr His Thr Gly Glu Lys Pro Phe Ala
145                 150                 155                 160

Cys Asp Ile Cys Gly Arg Lys Phe Ala Arg Arg Asp Asn Leu His Ser
                165                 170                 175

His Thr Lys Ile His Glu Leu Glu Glu Lys Lys Ser Glu Leu Arg His
            180                 185                 190

Lys Leu Lys Tyr Val Pro His Glu Tyr Ile Glu Leu Ile Glu Ile Ala
        195                 200                 205

Arg Asn Ser Thr Gln Asp Arg Ile Leu Glu Met Lys Val Met Glu Phe
210                 215                 220

Phe Met Lys Val Tyr Gly Tyr Arg Gly Lys His Leu Gly Gly Ser Arg
225                 230                 235                 240

Lys Pro Asp Gly Ala Ile Tyr Thr Val Gly Ser Pro Ile Asp Tyr Gly
                245                 250                 255

Val Ile Val Asp Thr Lys Ala Tyr Ser Gly Gly Tyr Asn Leu Pro Ile
            260                 265                 270

Gly Gln Ala Asp Glu Met Gln Arg Tyr Val Lys Glu Asn Gln Thr Arg
        275                 280                 285

Asn Lys His Ile Asn Pro Asn Glu Trp Trp Lys Val Tyr Pro Ser Ser
290                 295                 300

Val Thr Glu Phe Lys Phe Leu Phe Val Ser Gly His Phe Ser Gly Asn
305                 310                 315                 320

Tyr Lys Ala Gln Leu Thr Arg Leu Asn Arg Lys Thr Asn Cys Asn Gly
                325                 330                 335

Ala Val Leu Ser Val Glu Glu Leu Leu Ile Gly Gly Glu Met Ile Lys
            340                 345                 350

Ala Gly Thr Leu Thr Leu Glu Glu Val Arg Arg Lys Phe Asn Asn Gly
        355                 360                 365

Glu Ile Asn Phe
        370

```
<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Leu Arg Gly Ser Ile Ser Arg Ala Arg Pro Leu Asn Pro His Pro
1               5                   10                  15

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Leu Arg Gly Ser Gln Leu Val Lys Ser
1               5

<210> SEQ ID NO 7
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Val Pro Ala Ala Met Ala Glu Arg Pro Phe Gln Cys Arg Ile Cys Met
1               5                   10                  15

Arg Asn Phe Ser Asp Gln Ser Asn Leu Arg Ala His Ile Arg Thr His
            20                  25                  30

<210> SEQ ID NO 8
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Thr Gly Glu Lys Pro Phe Ala Cys Asp Ile Cys Gly Arg Lys Phe Ala
1               5                   10                  15

Arg Asn Phe Ser Leu Thr Met His Thr Lys Ile His
            20                  25

<210> SEQ ID NO 9
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Thr Gly Ser Gln Lys Pro Phe Gln Cys Arg Ile Cys Met Arg Asn Phe
1               5                   10                  15

Ser Ser Thr Gly Asn Leu Thr Asn His Ile Arg Thr His
            20                  25
```

```
<210> SEQ ID NO 10
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Thr Gly Glu Lys Pro Phe Ala Cys Asp Ile Cys Gly Arg Lys Phe Ala
1               5                   10                  15

Thr Ser Gly Ser Leu Thr Arg His Thr Lys Ile His
            20                  25

<210> SEQ ID NO 11
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Thr His Pro Arg Ala Pro Ile Pro Lys Pro Phe Gln Cys Arg Ile Cys
1               5                   10                  15

Met Arg Asn Phe Ser Asp Gln Ser Asn Leu Arg Ala His Ile Arg Thr
            20                  25                  30

His

<210> SEQ ID NO 12
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Thr Gly Glu Lys Pro Phe Ala Cys Asp Ile Cys Gly Arg Lys Phe Ala
1               5                   10                  15

Ala Gln Cys Cys Leu Phe His His Thr Lys Ile His Leu Arg Gly Ser
            20                  25                  30

<210> SEQ ID NO 13
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Val Pro Ala Ala Met Ala Glu Arg Pro Phe Gln Cys Arg Ile Cys Met
1               5                   10                  15

Arg Lys Phe Ala Arg Asn Asp His Arg Thr Thr His Thr Lys Ile His
            20                  25                  30

<210> SEQ ID NO 14
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 14

Thr Gly Glu Lys Pro Phe Gln Cys Arg Ile Cys Met Arg Asn Phe Ser
1               5                   10                  15

Gln Lys Ala His Leu Ile Arg His Ile Arg Thr His
            20                  25

<210> SEQ ID NO 15
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Thr Gly Glu Lys Pro Phe Ala Cys Asp Ile Cys Gly Arg Lys Phe Ala
1               5                   10                  15

Gln Lys Gly Thr Leu Gly Glu His Thr Lys Ile His
            20                  25

<210> SEQ ID NO 16
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Thr Gly Ser Gln Lys Pro Phe Gln Cys Arg Ile Cys Met Arg Asn Phe
1               5                   10                  15

Ser Arg Gly Arg Asp Leu Ser Arg His Ile Arg Thr His
            20                  25

<210> SEQ ID NO 17
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Thr Gly Glu Lys Pro Phe Ala Cys Asp Ile Cys Gly Arg Lys Phe Ala
1               5                   10                  15

Arg Arg Asp Asn Leu His Ser His Thr Lys Ile His Leu Arg Gly Ser
            20                  25                  30

<210> SEQ ID NO 18
<211> LENGTH: 196
<212> TYPE: PRT
<213> ORGANISM: Unknown
<220> FEATURE:
<223> OTHER INFORMATION: Description of Unknown:
      Wild type FokI cleavage half domain

<400> SEQUENCE: 18

Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
            20                  25                  30

Arg Asn Ser Thr Gln Asp Arg Ile Leu Glu Met Lys Val Met Glu Phe
        35                  40                  45
```

```
Phe Met Lys Val Tyr Gly Tyr Arg Gly Lys His Leu Gly Gly Ser Arg
    50                  55                  60

Lys Pro Asp Gly Ala Ile Tyr Thr Val Gly Ser Pro Ile Asp Tyr Gly
 65                  70                  75                  80

Val Ile Val Asp Thr Lys Ala Tyr Ser Gly Gly Tyr Asn Leu Pro Ile
                 85                  90                  95

Gly Gln Ala Asp Glu Met Gln Arg Tyr Val Glu Glu Asn Gln Thr Arg
                100                 105                 110

Asn Lys His Ile Asn Pro Asn Glu Trp Trp Lys Val Tyr Pro Ser Ser
            115                 120                 125

Val Thr Glu Phe Lys Phe Leu Phe Val Ser Gly His Phe Lys Gly Asn
130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
        195

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asp Gln Ser Asn Leu Arg Ala
 1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Arg Asn Phe Ser Leu Thr Met
 1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ser Thr Gly Asn Leu Thr Asn
 1               5

<210> SEQ ID NO 22
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 22

Thr Ser Gly Ser Leu Thr Arg
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ala Gln Cys Cys Leu Phe His
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Asn Asp His Arg Thr Thr
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gln Lys Ala His Leu Ile Arg
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gln Lys Gly Thr Leu Gly Glu
1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Arg Arg Asp Asn Leu His Ser
1               5
```

```
<210> SEQ ID NO 28
<211> LENGTH: 1727
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 28
gggagacaag cuuugaauua caagcuugcu uguucuuuuu gcagaagcuc agaauaaacg     60
cucaacuuug gcagaucgaa uucgccaugg acuacaaaga ccaugacggu gauuauaaag    120
aucaugacau cgauuacaag gaugacgaug acaagauggc ccccaagaag aagaggaagg    180
ucggcauuca cggggguaccc gccgcuaugg cugagaggcc cuuccagugu cgaaucugca    240
ugcagaacuu cagugaccag uccaaccugc gcgcccacau ccgcacccac accggcgaga    300
agccuuuugc cugugacauu uguggggagga aauuugcccg caacuucucc cugaccaugc    360
auaccaagau acacacgggc agccaaaagc ccuuccagug ucgaaucugc augcagaacu    420 ucaguccac cggcaaccug accaaccaca uccgcaccca caccggcgag aagccuuuug    480
ccugugacau uuguggggagg aaauuugcca ccuccggcuc ccugacccgc cauaccaaga    540
uacacacgca cccgcgcgcc ccgauccccga agcccuucca gugucgaauc ugcaugcaga    600
acuucaguga ccaguccaac cugcgcgccc acauccgcac ccacaccggc gagaagccuu    660
uugccuguga cauuuguggg aggaaauuug ccgcccagug uugucuguuc caccauacca    720
agauacaccu gcgggggaucc aucagcagag ccagaccacu gaacccgcac ccggagcugg    780
aggagaagaa guccgagcug cggcacaagc ugaaguacgu gccccacgag uacaucgagc    840
ugaucgagau cgccaggaac agcacccagg accgcauccu ggagaugaag gugauggagu    900
ucuucaugaa gguguacggc ucaggggaaa agcaccuggg cggaagcaga aagccugacg    960
gcgccaucua uacaguggc agccccaucg auuacggcgu gaucguggac acaaaggccu   1020
acagcggcgg cuacaaucug ccuaucggcc aggccgacga gauggagaga uacguggagg   1080
agaaccagac ccggggauaag caccucaacc ccaacgagug guggaaggug uacccuagca   1140
gcgugaccga guucaaguuc cuguucguga gcggccacuu caagggcaac uacaaggccc   1200
agcugaccag gcugaaccac aucaccaacu gcaauggcgc cgugcugagc guggaggagc   1260
ugcugaucgg cggcgagaug aucaaagccg gcacccugac acuggaggag gugcggcgca   1320
aguucaacaa cggcgagauc aacuucagau cuugauaacu cgagucuaga agcucgcuuu   1380
cuugcugucc aauuucuauu aaagguuccu uguuccccua agccaacua cuaaacuggg   1440 ggauauuaug aaggggccuug agcaucugga uucugccuaa uaaaaaacau uuauuuucau   1500
ugcugcgcua gaagcucgcu uucuugcugu ccaauuucua uuaaagguuc cuuguuccc   1560 uaaguccaac uacuaaacug ggggauauua ugaagggccu ugagcaucug gauucugccu   1620
aauaaaaaac auuuauuuuc auugcugcgg gacauucuau auuaaaaaaa aaaaaaaaa   1680 aaaaaaaaa aaaaaaaaaa aaaaaaaaaa aaaaaaaaaa aaacuag              1727

<210> SEQ ID NO 29
<211> LENGTH: 422
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29
```

```
Met Asp Tyr Lys Asp His Asp Gly Asp Tyr Lys Asp His Asp Ile Asp
1               5                   10                  15
Tyr Lys Asp Asp Asp Lys Met Ala Pro Lys Lys Arg Lys Val
            20                  25                  30
Gly Ile His Gly Val Pro Ala Ala Met Ala Glu Arg Pro Phe Gln Cys
            35                  40                  45
Arg Ile Cys Met Gln Asn Phe Ser Asp Gln Ser Asn Leu Arg Ala His
    50                  55                  60
Ile Arg Thr His Thr Gly Glu Lys Pro Phe Ala Cys Asp Ile Cys Gly
65                  70                  75                  80
Arg Lys Phe Ala Arg Asn Phe Ser Leu Thr Met His Thr Lys Ile His
                85                  90                  95
Thr Gly Ser Gln Lys Pro Phe Gln Cys Arg Ile Cys Met Gln Asn Phe
            100                 105                 110
Ser Ser Thr Gly Asn Leu Thr Asn His Ile Arg Thr His Thr Gly Glu
            115                 120                 125
Lys Pro Phe Ala Cys Asp Ile Cys Gly Arg Lys Phe Ala Thr Ser Gly
            130                 135                 140
Ser Leu Thr Arg His Thr Lys Ile His Thr His Pro Arg Ala Pro Ile
145                 150                 155                 160
Pro Lys Pro Phe Gln Cys Arg Ile Cys Met Gln Asn Phe Ser Asp Gln
                165                 170                 175
Ser Asn Leu Arg Ala His Ile Arg Thr His Thr Gly Glu Lys Pro Phe
            180                 185                 190
Ala Cys Asp Ile Cys Gly Arg Lys Phe Ala Ala Gln Cys Cys Leu Phe
            195                 200                 205
His His Thr Lys Ile His Leu Arg Gly Ser Ile Ser Arg Ala Arg Pro
            210                 215                 220
Leu Asn Pro His Pro Glu Leu Glu Glu Lys Lys Ser Glu Leu Arg His
225                 230                 235                 240
Lys Leu Lys Tyr Val Pro His Glu Tyr Ile Glu Leu Ile Glu Ile Ala
                245                 250                 255
Arg Asn Ser Thr Gln Asp Arg Ile Leu Glu Met Lys Val Met Glu Phe
            260                 265                 270
Phe Met Lys Val Tyr Gly Tyr Arg Gly Lys His Leu Gly Gly Ser Arg
            275                 280                 285
Lys Pro Asp Gly Ala Ile Tyr Thr Val Gly Ser Pro Ile Asp Tyr Gly
            290                 295                 300
Val Ile Val Asp Thr Lys Ala Tyr Ser Gly Gly Tyr Asn Leu Pro Ile
305                 310                 315                 320
Gly Gln Ala Asp Glu Met Glu Arg Tyr Val Glu Glu Asn Gln Thr Arg
            325                 330                 335
Asp Lys His Leu Asn Pro Asn Glu Trp Trp Lys Val Tyr Pro Ser Ser
            340                 345                 350
Val Thr Glu Phe Lys Phe Leu Phe Val Ser Gly His Phe Lys Gly Asn
            355                 360                 365
Tyr Lys Ala Gln Leu Thr Arg Leu Asn His Ile Thr Asn Cys Asn Gly
            370                 375                 380
Ala Val Leu Ser Val Glu Glu Leu Leu Ile Gly Gly Glu Met Ile Lys
385                 390                 395                 400
Ala Gly Thr Leu Thr Leu Glu Glu Val Arg Arg Lys Phe Asn Asn Gly
            405                 410                 415
Glu Ile Asn Phe Arg Ser
```

<210> SEQ ID NO 30
<211> LENGTH: 1680
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 30

```
gggagacaag cuugaauaca agcuugcuug uucuuuuugc agaagcucag aauaaacgcu    60
caacuuuggc agaucgaauu cgccuagaga ucuggcggcg gagagggcag aggaagucuu   120
cuaaccugcg gugacgugga ggagaauccc ggcccuagga ccauggacua caaagaccau   180
gacggugauu auaaagauca ugacaucgau uacaaggaug acgaugacaa gauggccccc   240
aagaagaaga ggaaggucgg cauucauggg guacccgccg cuauggcuga gaggcccuuc   300
cagugucgaa ucugcaugca gaaguuugcc cgcaacgacc accgcaccac ccauaccaag   360
auacacacgg gcgagaagcc cuuccagugu cgaaucugca ugcagaacuu cagucagaag   420
gcccaccuga uccgccacau ccgcacccac accggcgaga agccuuuugc cugugacauu   480
ugugggagga aauuugccca aagggcaccc ugggcgagc auaccaagau acacacggga   540
ucucagaagc ccuuccagug ucgaaucugc augcagaacu cagucgcgg ccgcgaccug   600
ucccgccaca uccgcaccca caccggcgag aagccuuuug ccugugacau uguggggagg   660
aaauuugccc gccgcgacaa ccugcacucc auaccaaga uacaccgcg gggauccag   720
cuggugaaga gcgagcugga ggagaagaag uccgagcugc ggcacaagcu gaaguacgug   780
cccccacgagu acaucgagcu gaucgagauc gccaggaaca gcaccaggga ccgcauccug   840
gagaugaagg ugauggaguu cuucaugaag guguacggcu acaggggaaa gcaccugggc   900
ggaagcagaa agccgacgg cgccaucuau acaguggca gccccaucga uuacggcgug   960
aucguggaca caaaggccua cagcggcggc uacaaucugc cuaucggcca ggccgacgag  1020
augcagagau acgugaagga gaaccagacc cggaauaagc acaucaaccc caacgagugg  1080
uggaaggugu acccuagcag cgugaccgag uucaaguucc uguucgugag cggccacuuc  1140
agcggcaacu acaaggccca gcugaccagg cugaaccgca aaccaacug caauggcgcc  1200
gugcugagcg uggaggagcu gcugaucggc ggcgagauga ucaaagccgg cacccugaca  1260
cuggaggagg ugcggcgcaa guucaacaac ggcgagauca cuucugaua acucgagucu  1320
agaagcucgc uuucuugcug uccaauuucu auuaaagguu ccuuguuccc cuaaguccaa  1380
cuacuaaacu gggggauauu augaagggcc uugagcaucu ggauucugcc uaauaaaaaa  1440
cauuuauuuu cauugcugcg cuagaagcuc gcuuucuugc uguccaauuu cuauuaaagg  1500
uuccuuuguu cccuaagucc aacuacuaaa cuggggggaua uuaugaaggg ccuugagcau  1560
cuggauucug ccuaauaaaa aacauuuauu ucauugcug cgggacauuc uuaauuaaaa  1620
aaaaaaaaaa aaaaaaaaaa aaaaaaaaaa aaaaaaaaaa aaaaaaaaaa aaaaaacuag  1680
```

<210> SEQ ID NO 31
<211> LENGTH: 381
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 31

Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Arg Lys Val
            20              25              30

Gly Ile His Gly Val Pro Ala Ala Met Ala Glu Arg Pro Phe Gln Cys
            35              40              45

Arg Ile Cys Met Gln Lys Phe Ala Arg Asn Asp His Arg Thr Thr His
    50              55              60

Thr Lys Ile His Thr Gly Glu Lys Pro Phe Gln Cys Arg Ile Cys Met
65              70              75              80

Gln Asn Phe Ser Gln Lys Ala His Leu Ile Arg His Ile Arg Thr His
            85              90              95

Thr Gly Glu Lys Pro Phe Ala Cys Asp Ile Cys Gly Arg Lys Phe Ala
            100             105             110

Gln Lys Gly Thr Leu Gly Glu His Thr Lys Ile His Thr Gly Ser Gln
            115             120             125

Lys Pro Phe Gln Cys Arg Ile Cys Met Gln Asn Phe Ser Arg Gly Arg
    130             135             140

Asp Leu Ser Arg His Ile Arg Thr His Thr Gly Glu Lys Pro Phe Ala
145             150             155             160

Cys Asp Ile Cys Gly Arg Lys Phe Ala Arg Arg Asp Asn Leu His Ser
                165             170             175

His Thr Lys Ile His Leu Arg Gly Ser Gln Leu Val Lys Ser Glu Leu
            180             185             190

Glu Glu Lys Lys Ser Glu Leu Arg His Lys Leu Lys Tyr Val Pro His
            195             200             205

Glu Tyr Ile Glu Leu Ile Glu Ile Ala Arg Asn Ser Thr Gln Asp Arg
    210             215             220

Ile Leu Glu Met Lys Val Met Glu Phe Phe Met Lys Val Tyr Gly Tyr
225             230             235             240

Arg Gly Lys His Leu Gly Gly Ser Arg Lys Pro Asp Gly Ala Ile Tyr
            245             250             255

Thr Val Gly Ser Pro Ile Asp Tyr Gly Val Ile Val Asp Thr Lys Ala
            260             265             270

Tyr Ser Gly Gly Tyr Asn Leu Pro Ile Gly Gln Ala Asp Glu Met Gln
    275             280             285

Arg Tyr Val Lys Glu Asn Gln Thr Arg Asn Lys His Ile Asn Pro Asn
    290             295             300

Glu Trp Trp Lys Val Tyr Pro Ser Ser Val Thr Glu Phe Lys Phe Leu
305             310             315             320

Phe Val Ser Gly His Phe Ser Gly Asn Tyr Lys Ala Gln Leu Thr Arg
            325             330             335

Leu Asn Arg Lys Thr Asn Cys Asn Gly Ala Val Leu Ser Val Glu Glu
            340             345             350

Leu Leu Ile Gly Gly Glu Met Ile Lys Ala Gly Thr Leu Thr Leu Glu
            355             360             365

Glu Val Arg Arg Lys Phe Asn Asn Gly Glu Ile Asn Phe
370             375             380

<210> SEQ ID NO 32
<211> LENGTH: 45
<212> TYPE: DNA
<213> ORGANISM: Artificial Sequence
<220> FEATURE:

```
<223> OTHER INFORMATION: Description of Artificial Sequence: Synthetic
      primer
<220> FEATURE:
<221> NAME/KEY: modified_base
<222> LOCATION: (21)..(24)
<223> OTHER INFORMATION: a, c, t, g, unknown or other

<400> SEQUENCE: 32
acacgacgct cttccgatct nnnnagtcct cttctacccc accca             45

<210> SEQ ID NO 33
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gacgtgtgct cttccgatct ctactcttag acataacaca ccaggg           46

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Arg Gly Arg Asp Leu Ser Arg
1               5
```